(12) United States Patent
Li et al.

(10) Patent No.: US 11,701,369 B2
(45) Date of Patent: Jul. 18, 2023

(54) POLYMERIC BILE ACID DERIVATIVES INHIBIT HEPATITIS B AND D VIRUS AND NTCP TRANSPORT

(71) Applicant: Huahui Health Ltd., Beijing (CN)

(72) Inventors: Wenhui Li, Beijing (CN); Xiangbing Qi, Beijing (CN); Huan Yan, Beijing (CN); Yang Liu, Beijing (CN); Zhiqiang Wang, Beijing (CN); Bo Peng, Beijing (CN); Lei Zhang, Beijing (CN)

(73) Assignee: Huahui Health Ltd., Beijing (CN)

( * ) Notice: Subject to any disclaimer, the term of this patent is extended or adjusted under 35 U.S.C. 154(b) by 0 days.

(21) Appl. No.: 15/513,102

(22) PCT Filed: Sep. 28, 2015

(86) PCT No.: PCT/CN2015/091000
§ 371 (c)(1),
(2) Date: Mar. 21, 2017

(87) PCT Pub. No.: WO2016/045642
PCT Pub. Date: Mar. 31, 2016

(65) Prior Publication Data
US 2017/0266206 A1 Sep. 21, 2017

(30) Foreign Application Priority Data
Sep. 28, 2014 (WO) ................ PCT/CN2014/087655

(51) Int. Cl.
| | |
|---|---|
| *A61K 31/585* | (2006.01) |
| *A61K 31/575* | (2006.01) |
| *C07J 9/00* | (2006.01) |
| *C07J 41/00* | (2006.01) |
| *C07J 71/00* | (2006.01) |
| *C07J 43/00* | (2006.01) |
| *A61K 31/58* | (2006.01) |
| *A61K 45/06* | (2006.01) |

(52) U.S. Cl.
CPC .......... *A61K 31/585* (2013.01); *A61K 31/575* (2013.01); *A61K 31/58* (2013.01); *A61K 45/06* (2013.01); *C07J 9/00* (2013.01); *C07J 9/005* (2013.01); *C07J 41/005* (2013.01); *C07J 41/0055* (2013.01); *C07J 41/0061* (2013.01); *C07J 43/003* (2013.01); *C07J 71/0047* (2013.01)

(58) Field of Classification Search
CPC .... A61K 31/575; A61K 31/58; A61K 31/585; A61K 2300/00; A61K 45/06; A61K 47/60; A61K 47/643; C07J 41/0055; C07J 41/0061; C07J 43/003; C07J 41/0088; C07J 41/005; C07J 71/0047; C07J 9/00; C07J 9/005; A61P 31/14; A61P 31/20; A61P 43/00

USPC ........................................................ 552/502
See application file for complete search history.

(56) References Cited

U.S. PATENT DOCUMENTS

| | | | |
|---|---|---|---|
| 5,430,116 A | 7/1995 | Kramer et al. | |
| 5,559,258 A | 9/1996 | Enhsen et al. | |
| 5,871,905 A | 2/1999 | Thieme et al. | |
| 6,268,392 B1 | 7/2001 | Keller et al. | |
| 6,420,417 B1 * | 7/2002 | Keller ..................... | A61K 31/22 514/431 |
| 7,141,559 B2 * | 11/2006 | Bishop ....................... | C07J 1/00 514/179 |
| 7,521,439 B2 * | 4/2009 | Bishop ....................... | C07J 1/00 514/179 |
| 2017/0266206 A1 * | 9/2017 | Li ........................ | A61K 31/585 |

FOREIGN PATENT DOCUMENTS

| | | |
|---|---|---|
| CN | 101182331 A | 11/2007 |
| CN | 101307076 | 11/2008 |
| CN | 101439187 | 5/2009 |
| JP | 2009519345 A | 5/2009 |
| WO | 9840375 | 9/1998 |
| WO | 2007064691 | 6/2007 |
| WO | 2009146123 | 12/2009 |
| WO | 2011056650 | 5/2011 |
| WO | 2011066260 | 6/2011 |
| WO | 2013159243 | 10/2013 |
| WO | 2014072524 | 5/2014 |

OTHER PUBLICATIONS

Batta et al., "Substrate Specificity of Cholylglycine Hydrolase for the Hydrolysis of Bile Acid Conjugates", The Journal of Biological Chemistry; vol. 259, Dec. 1984, pp. 15035-15039.
Shefer et al., "Metabolism of Iso-Bile Acids in the Rat", The Journal of Biological Chemistry, vol. 257, No. 3, Feb. 10, 1982?? pp. 1401-1406.
Setchell et al., "Hepatic Bile Acid Metabolism During Early Development Revealed from the Analysis of Human Fetal Gallbladder Bile", The Journal of Biological Chemistry, vol. 263, No. 12, Nov. 15, 1988, pp. 1637-1644.
Marschall et al., "The Major Metabolites of Ursodeoxycholic Acid in Human Urine are Conjugated with N-acetylglucosamine", Hepatology, vol. 20, Oct. 1994, pp. 845-853.
Marschall et al., "Human Liver Class I Alcohol Dehydrogenase γγ Isozyme: The Sole Cytosolic 3ß-Hydroxysteroid Dehydrogenase of Iso Bile Acids", Hepotology, vol. 31, Dec. 30, 2003, pp. 990-996.
De Vrueh et al., "Synthesis of a Lipophilie Prodrug of 9-(2-Phosphonylmethoxyethyl)adenine (PMEA) and Its Incorporation into a Hepatocyte-Specific Lipidic Carrier", Pharmaceutical Research, vol. 16, No. 8, Aug. 1999, pp. 1179-1185.

(Continued)

*Primary Examiner* — Yong S. Chong
(74) *Attorney, Agent, or Firm* — Nixon & Vanderhye, P.C.

(57) ABSTRACT

The invention provides for treating HBV or HDV infection or inhibiting human sodium taurocholate co-transporting polypeptide (hNTCP) with a polymeric bile acid or salt thereof, and pharmaceutical compositions comprising a polymeric bile acid or salt thereof, and a second HBV or HDV medicament.

9 Claims, 10 Drawing Sheets

(56) References Cited

OTHER PUBLICATIONS

De Vrueh et al., "Carrier-Mediated Delivery of 9-(2-Phosphonylmethoxyethyl)Adenine_ to Parenchymal Liver Cells: a Novel Therapeutic Approach for Hepatitis B", Antimicrobial Agents and Chemotherapy, Mar. 2000, pp. 477-483.

Bijsterbosch et al., "Carrier-Mediated Delivery Improves the Efficacy of 9-(2-Phosphonylmethoxyethyl)Adenine against Hepatitis B Virus", Molecular Pharmacology, vol. 60, No. 3, Sep. 2001, pp. 521-527.

Criado et al., "Structural Characterization, Kinetic Studies, and in Vitro Biological Activity of New cis-Diamminebis-cholylglycinate(O,O') Pt(II) and cis-Diamminebis-ursodeoxycholate(O,O') Pt(II) Complexes", Bioconjugate Chemistry, Feb. 24, 2000, vol. 11, pp. 167-174.

Romero et al., "Evidence for dual effects of DNA-reactive bile acid derivatives (Barnets) on hepatitis B virus life cycle in an in vitro replicative system", Antiviral Chemistry & Chemotherapy, vol. 13, Dec. 1, 2002, pp. 371-380.

Vicens et al., "Novel cationic and neutral glycocholic acid and polyamine conjugates able to inhibit transporters involved in hepatic and intestinal bile acid uptake", Bioorganic & Medicinal Chemistry, vol. 15, No. 6, Mar. 15, 2007, pp. 2359-2367.

Herraez et al., "In vitro inhibition of OATP-mediated uptake of phalloidin using bile acid derivatives", Toxicology and Applied Pharmacology, vol. 239, Aug. 15, 2009, pp. 13-20.

Blanchet et al., "Use of FDA approved therapeutics with hNTCP metabolic inhibitory properties to impair the HDV lifecycle", Antiviral Research, vol. 106, Jun. 2014, pp. 111-115.

Yan et al., "Sodium taurocholate cotransporting polypeptide is a functional receptor for human hepatitis B and D virus", eLIFE, e00049, Nov. 13, 2012, pp. 1-28.

Yan et al., "Molecular Determinants of Hepatitis B and D Virus Entry Restriction in Mouse Sodium Taurocholate Cotransporting Polypeptide", Journal of Virology, vol. 87, No. 14, Jul. 2013, pp. 7977-7991.

Yan et al., "Viral entry of Hepatitis B and D virues and bile salts transportation share common molecular determinants on sodium taurocholate cotransporting polypeptide", Journal of Virology, vol. 88, No. 6, Mar. 2014, pp. 3273-3284.

Konig et al., "Kinetics of the bile acid transporter and hepatitis B virus receptor Na+/taurocholate cotransporting polypeptide (NTCP) in hepatocytes", Journal of Hepatology; Oct. 2014, vol. 61, pp. 867-875.

Ni et al., Identification of NTCP as an HBV Receptor: The Beginning of the End or the End of the Beginning?, Gastroenterol, Apr. 2014, vol. 146, No. 4, pp. 902-905.

* cited by examiner

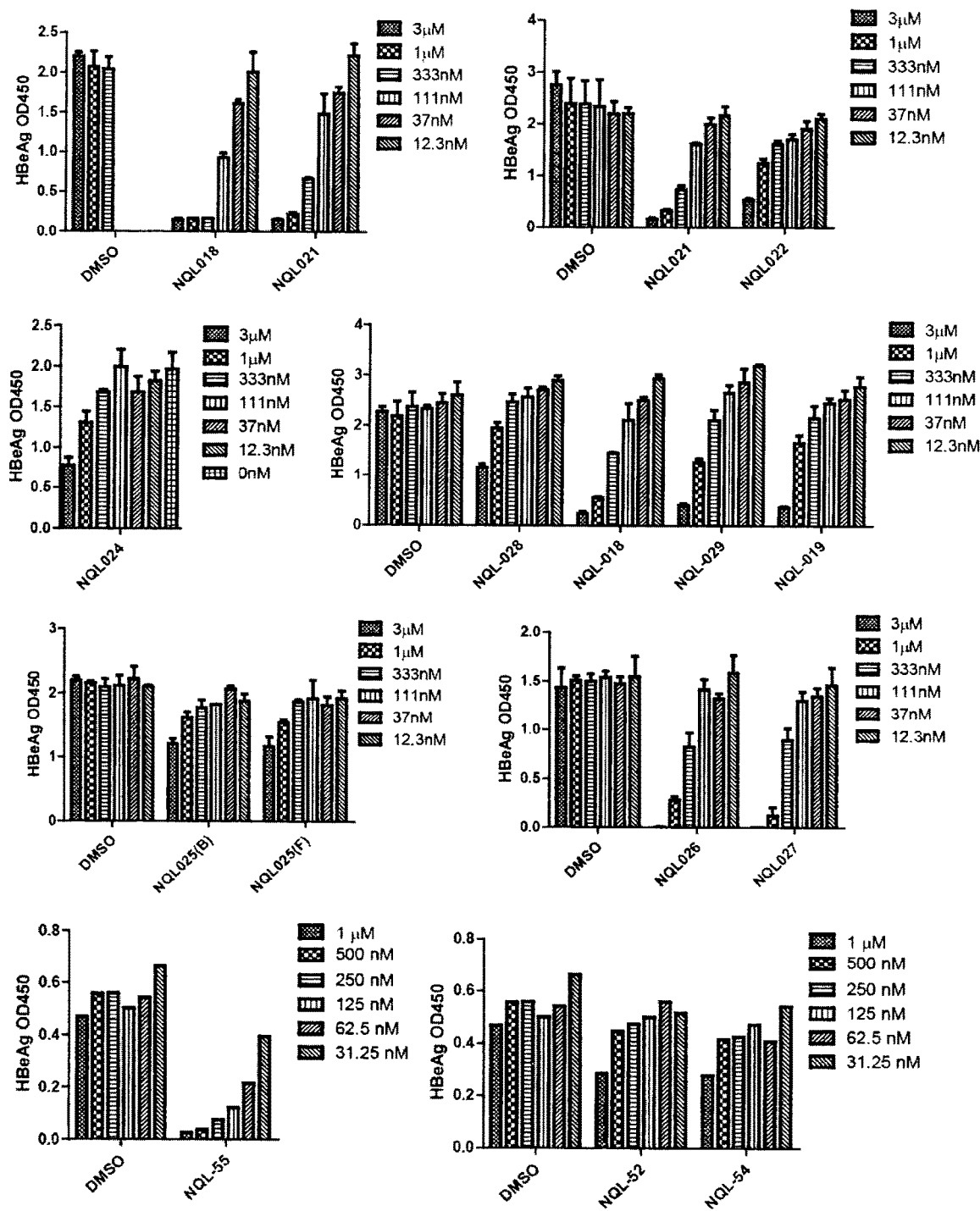
Fig. 12 Structure activity relationship analysis

POLYMERIC BILE ACID DERIVATIVES INHIBIT HEPATITIS B AND D VIRUS AND NTCP TRANSPORT

INTRODUCTION

More than one third of the world population has been infected by Hepatitis B virus (HBV), 240 million people are presently chronically infected, and 15 million are also infected with Hepatitis D virus (HDV). HBV infection and related diseases result in about one million deaths annually.

We previously identified sodium taurocholate cotransporting polypeptide (NTCP), a key bile salt transporter of hepatocytes, as a functional receptor for both HBV and HDV, and we showed that bile acids could inhibit HBV and HDV infection (Yan et al. Elife 1:e00049, 2012; Yan et al. J Virol 87:7977-7991, 2013; Yan et al. J Virol 88:3273-3284, 2014). Other NTCP inhibitors have also since been reported to interfere with HBV and HDV infection, including irbesartan, ezetimibe, ritonavir(6) and CSA (e.g Blanchet et al., Antiviral research 106:111-115, 2014.

We synthesized bile acid derivatives and used our human hepatoma HepG2 cells complemented with human NTCP (HepG2-NTCP) cell culture system to evaluate their inhibitory effect for viral infection and substrate transporting. By carefully quantitative analysis we observed anomalous HBV inhibitory activity in some batches of bile acids, and investigated the source of these activity discrepancies. We determined that some batches had contaminating polymeric bile salt bi-products, and we resolved that these impurities had higher specific activity than the corresponding normal bile salt. We then prepared purified batches of a wide range of polymeric bile salts and confirmed enhanced activity of the polymeric forms across a variety of monomers and linkages. Accordingly, we disclose uses and compositions of polymeric bile acid derivatives (PBADs) to inhibit HBV and HDV infection by targeting hNTCP.

SUMMARY OF THE INVENTION

The invention provides methods and compositions for treating HBV or HDV infection or inhibiting human sodium taurocholate co-transporting polypeptide (hNTCP). In one aspect the method comprises administering to a person in need thereof a polymeric bile acid or salt thereof. The method may comprise the antecedent step of determining that the person is in need thereof, and/or the subsequent step of detecting a resultant therapeutic effect.

In embodiments:

(i) the polymeric bile acid comprises 2, 3 or 4 covalently-linked monomers, each monomer having a structure independently of formula I:

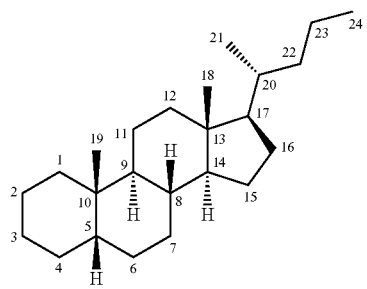

(I)

wherein each C1-C24 is independently optionally substituted with a hydrocarbon or heterohydrocarbon or heteroatom-containing functional group (non-hydrogen substituent), or with an optionally-substituted alkyl or heteroalkyl, alkenyl or heteroalkenyl, alkynyl or heteroalkynyl, alkoxyl or heteroalkoxyl, including cyclic and substituted forms of each, aryl and heteroaryl, wherein hetero-forms comprise 1-4 heteroatoms such as N, O, P and S, or with substituted or unsubstituted (C1-C4)alkyl, (C2-C4)alkenyl, (C6-C8)alkenyl, (C2-C4)alkynyl, (C6-C8)alkynyl, (C1-C4)alkoxyl, (C6-C8)alkoxyl, 3-oxetanyloxy, 3-tetrahydrofuranyloxy, Cl, F, fluoro-substituted (C1-C2)alkyl, (C1-C4)alkyl-SO$_2$—, (C3-C6)cycloalkyl, or a (C5-C6)heterocycle having 1 or 2 heteroatoms each independently selected from N, O, P or S, or with a functional group such as hydroxyl, haloformyl, carbonyl, aldehyde, carboxyl, ester, acetal, carboxamide, hydroperoxyl, epoxide, peroxide, oxime, amine (including primary, secondary and tertiary amines), amide, imine, imide, quaternary ammonium salt, amine oxide, azide, azo, aldimine, isocyanide, isocyanate, isothiocyanate, diazo, azido, aziridine, diaziridine, hydrazine, hydrzone, cyanate, nitrate, nitrile, nitrite, nitride, nitro, nitroso, silane, alkylsilane, siloxane, halosilane, phosphine, phosphorite, phosphate, thiophosphonate, quaternary phosphonium salt, phosphono, phosphides, sulfide, sulfite, sulfonate, thiocyanate, thiosulfate, sulfoxide, sulfimide, sulfone, sulfoximines, sulfonium, and sulfhydryl.

(ii) each substituent is independently: OH, OAc (Ac=COCH$_3$, Acetate), OBz (Bz=COPh, benzoyl), OBn (Bn=benzyl), OTs (Ts=tosyl, p-toluenesulfonyl), OMs (Ms=methanesulfonyl), OSiR$_3$, OTf (Tf=trifluoromethanesulfonyl), OTHP (THP, tetrahydropyran), OCOR, OR, NH$_2$, NHBoc (Boc=tert-butyloxycarbonyl), NHAc (Ac=COCH$_3$, Acetate), NHBz (Bz=COPh, benzoyl), NHTs (Ts=tosyl, p-toluenesulfonyl), NHTf (Tf=Trifluoromethanesulfonyl), NHMs (Ms=methanesulfonyl), NHSiR$_3$, NHR; NBn$_2$ (Bn=benzyl), NTf$_2$ (Tf=trifluoromethanesulfonyl) NHCOR and NR1R2), —N$_2$, —N$_3$; phosphoric acid (—OP(O)(OH)$_2$, sulfuric acids (—OSO$_2$OH) or carboxylic acid (—OCOH), carboxylic ester (—OCOR); phosphorite (—OP(O)$_m$O—) or phosphate (—OP(OR)$_m$O—), sulfonate, sulfate (—OS(O)$_m$O—), sulfite (—OS(OR)$_m$O—), disulfite or pyrosulfate, in which m is equal to 0, 1 and 2; wherein each R, R1 and R2 is independently H, an alkyl, aryl, alkenyl, alkynyl, carbonyl, or ether radical having up to 15 carbon atoms, which is branched or unbranched, a cyclo-(alkyl, aryl, alkenyl, alkynyl, carbonyl, or ether) radical having 3 to 15 carbon atoms or a phenyl or benzyl radical, which are unsubstituted or mono-, bis- or trisubstituted by halide, (C1-C4)-alkyl or (C1-C4)-alkoxyl) or (C1-C6)-alkylamine), ethylene oxide, or an alkyl, aryl, alkenyl or alkynyl radical having up to 15 carbon atoms, which is branched or unbranched, a cycloalkyl radical having 3 to 15 carbon atoms, a phenyl or benzyl radical, which are unsubstituted or mono-, bis-, tri-substituted by halide, (C1-C4)-alkyl, (C1-C4)-alkoxyl or (C1-C6)-alkylamine), or heteroatom (e.g. —SO$_2$OH, F, Cl, Br, S).

(iii) each of C3, C6, C7 and C24 is independently substituted with:
a substituent of claim 2; or
a substituent of claim 3; or
—NR1R2, —OR or —COR, wherein each R, R1 and R2 is independently H or a substituent of claim 2;

(iv) C24 is substituted with:
—CH$_2$OH, —COOM, in which M is an alkali metal, alkaline earth metal or quaternary ammonium ion; or —CONHCH$_2$CH$_2$SO$_3$H, —CONHRSO$_3$H or —COOH, —COOR, —CONH$_2$, —CH$_2$NH$_2$, —CONH or NRR, wherein each R is independently H, an alkyl, aryl, alkenyl or alkynyl radical having up to 15 carbon atoms, which is branched or unbranched, a cycloalkyl radical having 3 to 10 carbon atoms or a phenyl or benzyl radical, which are unsubstituted or mono-, bis- or trisubstituted by halide (e.g. F, Cl, Br), (C1-C4)-alkyl or (C1-C4)-alkoxyl) or (C1-C6)-alkylamine), (v) each of C3, C6 and C7 is independently substituted with:

| | |
|---|---|
| —OH, —OAc (Ac = COCH$_3$, Acetate), | —NH$_2$, —NHBoc (Boc = tert-BUtyloxycarbonyl), |
| —OBz (Bz = COPh, benzoyl), | —NHAc (Ac = COCH$_3$, Acetate), |
| —OBn (Bn = benzyl), | —NHBz (Bz = COPh, benzoyl), |
| —OTs (Ts = Tosyl, p-toluenesulfonyl), | —NHTs (Ts = Tosyl, p-toluenesulfonyl), |
| —OMs (Ms = methanesulfonyl), - | —NHTf (Tf = Trifluoromethanesulfonyl), |
| —OR, —OSiR$_3$, | —NHMs (Ms = methanesulfonyl), |
| —OTr(Tr = Triphenylmethyl), | —NBn$_2$ (Bn = Benzyl) or |
| —OTf (Tf = Trifluoromethanesulfonyl), | —NR1R2, |
| —OTHP (THP = tetrahydropyran), | —N$_3$, |
| -carbonyl | -alkyl | wherein each R, R1 and R2 is independently alkyl, aryl, alkenyl or alkynyl radical having up to 15 carbon atoms, which is branched or unbranched, a cycloalkyl radical having 3 to 15 carbon atoms or a phenyl or benzyl radical, which are unsubstituted or mono-, bis- or trisubstituted by halide (e.g. F, Cl, Br), (C1-C4)-alkyl or (C1-C4)-alkoxyl) or (C1-C6)-alkylamine);

(vi) the monomers a linked by 1 or 2 or 3 linkers, each independently L, wherein L is:

(a) alkyl, aryl, alkenyl or alkynyl radical having up to 15 carbon atoms, which is branched or unbranched, optionally substituted and optionally heteroatom containing;

(b) a cycloalkyl radical having 3 to 15 carbon atoms, or a phenyl or benzyl radical, which are unsubstituted or mono-, bis-, tri-substituted by halide (e.g. F, Cl, Br), (C1-C4)-alkyl, (C1-C4)-alkoxyl or (C1-C6)-alkylamine); or (c) a contiguous chain of between 2 and 200 atoms, preferably between 4 and 100 atoms, more preferably between 4 and 25 atoms, and a MW between 20 and 2K D, preferably between 40 and 1K D, more preferably between 56 and 1K D. L maybe bisymmetrical, or nonsymmetrical, and may link different, isometric or identical M1 and M2, typically has spans between about 3 and 3K A, preferably between about 6 and 2000, more preferably between about 12 and 1000 A, etc.; or (d) alkyl, aryl group and heteroatoms, amino acids or other aminoalkylsulfonic acids bonded with amide or ester bond;

(vii) the polymeric bile acid comprises a TUDCA moiety;

(viii) the polymeric bile acid is disclosed in a Table herein;

(ix) the polymeric bile acid is in a predetermined, unit dosage, effective amount.

(x) the method further comprises administering to the person a second, different HBV or HDV medicament, and/or detecting a resultant inhibition of hNTCP or HBV or HDV infection.

In another aspect the invention provides compositions comprising a polymeric bile acid or salt thereof, coformulated or copackaged or coadministered with a second, different HBV or HDV medicament;

In embodiments, the polymeric bile acid is a generally- or specifically-disclosed compound herein, including a polymeric acid which comprises 2, 3 or 4 covalently-linked monomers, each monomer having a structure independently of formula I (supra); and/or the medicament is lamivudine (Epivir), adefovir (Hepsera), tenofovir (Viread), telbivudine (Tyzeka), entecavir (Baraclude), bosentan, oxysterol, ezetimibe, reserpine, rosuvastatin, or bromsulphthalein.

The invention encompasses all combination of the particular embodiments recited herein.

DESCRIPTION OF PARTICULAR EMBODIMENTS OF THE INVENTION

Figure 1:
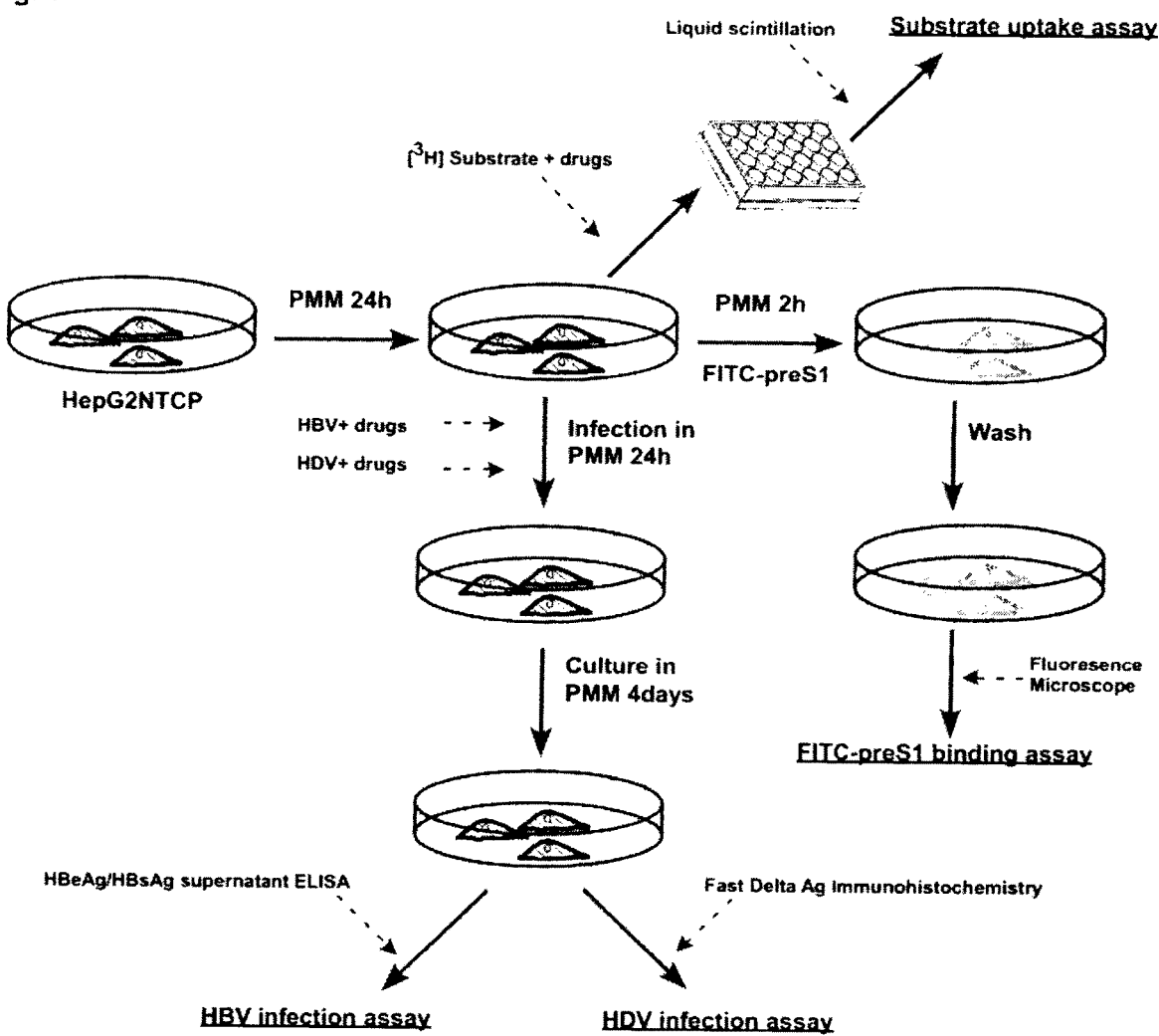
FIG. 1 Schematic illustration of the assays to study drug candidate potency and mechanism.

Applications include treatment of chronic HBV and HDV infection, protection against new HBV infection by vertical transmission and accidental exposure, prevention of HBV recurrence after liver transplantation and pathologies indicating NTCP inhibition, such as protecting hepatocytes from uptake of toxic bile acids or other NTCP transported agents.

The descriptions of particular embodiments and examples are provided by way of illustration and not by way of limitation. Those skilled in the art will readily recognize a variety of noncritical parameters that could be changed or modified to yield essentially similar results.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

Bile acids are steroid acids comprising four rings in a sterane core, and a side chain off the C17 carbon, typically of 5 or 8 carbons and terminating in a carboxyl group. Bile acids encompass natural products, such as found in the bile of mammals, and synthetic derivatives thereof, such as disclosed herein.

The term "heteroatom" as used herein generally means any atom other than carbon or hydrogen. Preferred heteroatoms include oxygen (O), phosphorus (P), sulfur (S), nitrogen (N), silicon (Si) and halogens, and preferred heteroatom functional groups are haloformyl, hydroxyl, aldehyde, amine, quaternary ammonium salt, amine oxide, azo, diazo, azido, aziridine, diaziridine, hydrazine, hydrzone, carboxyl, cyanyl, thiocyanyl, carbonyl, halo, hydroperoxyl, epoxide, peroxide, oxime, imine, imide, amide, aldimine, isocyanide, iscyanate, isothiocyanate, nitrate, nitrile, nitrite, nitride, nitro, nitroso, phosphate, thiophosphonate, phosphono, phosphides, quaternary phosphonium salt, silane, alkylsilane, siloxane, halosilane, sulfide, sulfite, sulfonate, thiosulfate, sulfonyl, sulfoxide, sulfimide, sulfone, sulfoximines, sulfonium, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen and phosphorous heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S~-CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)3, —CH$_2$—CH=N—OCH$_3$, and —CH=CH—N(CH3)-CH$_3$. Up to two heteroatoms may be consecutive, such as, for example, —CH$_2$—NH—OCH$_3$, —CH$_2$—S—S—CH$_2$—CH$_3$, and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, P, Si and S, and wherein the nitrogen and sulfur atoms may optionally be oxidized and the nitrogen and phosphine heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to five rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to six heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR'—SO$_2$NR''', —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R''' each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R'", —NR'—SO$_2$NR"R'", —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alkoxy- and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4) alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t- -, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C1-C6 alkyl, substituted or unsubstituted, optionally heteroatom C2-C6 alkenyl, substituted or unsubstituted, optionally heteroatom C2-C6 alkynyl, or substituted or unsubstituted, optionally heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, quaternary ammonium salt, amine oxide, azo, diazo, azido, aziridine, diaziridine, hydrazine, hydrzone, halogens, carbamoyl, carbonyl, carboxamido, carboxyl, cyanyl, thiocyanyl, ester, halo, haloformyl, hydroperoxyl, hydroxyl, epoxide, peroxide, oxime, imine, imide, amide, aldimine, isocyanide, iscyanate, isothiocyanate, N-tert-butoxycarbonyl, nitrate, nitrile, nitrite, nitro, nitroso, phosphate, thiophosphonate, phosphides, phosphono, quaternary phosphonium salt, silane, alkylsilane, siloxane, halosilane, sulfide, sulfite, sulfonate, thiosulfate, sulfonyl, sulfo, sulfoxide, sulfimide, sulfone, sulfoximines, sulfonium, sulfhydryl, thiol, thiocyanyl, trifluoromethyl or trifluromethyl ether (OCF$_3$).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Some of the subject compounds possess asymmetric carbon atoms (optical centers) or double bonds; the racemates, diastereomers, geometric isomers and specifically designated or depicted chirality is preferred and in many cases critical for optimal activity; however all such isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), Fluorine ($^{18}$F, $^{17}$F) or carbon-14 ($^{14}$C, $^{13}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-diabetes or anti-obesity agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

PBADs, including 3UT(NQL-012), 7UT(NQL-015), DIU (NQL-009) and 3TPT(NQL-018), showed greatly improved potency as the inhibitor of HBV and HDV virus infection. Our data indicate they can inhibit infection of HBV and HDV on HepG2-NTCP cells with an IC50 down to less than 50 nM, which is 100 times lower than their common precursor tauroursodeoxycholic acid (TUDCA). PBADs can also significantly block the substrate uptake of NTCP so they can also serve as NTCP transporting inhibitors.

TABLE A

TUDCA/UDCA monomer:

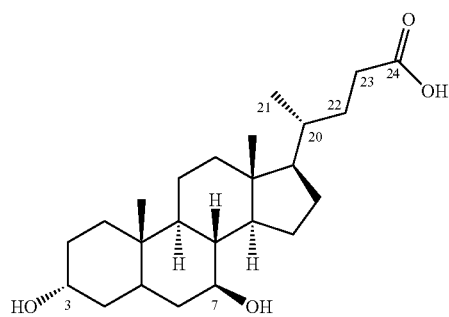

Ursodeoxycholic acid
(UDCA, U)

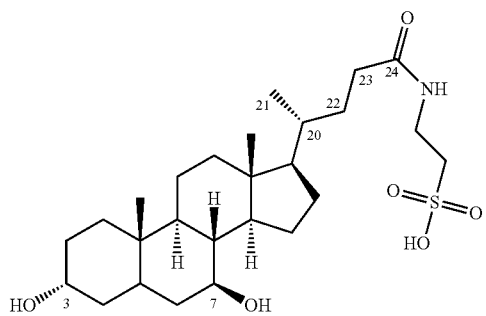

Tauroursodeoxycholic acid
(TUDCA, T)

TABLE A-continued
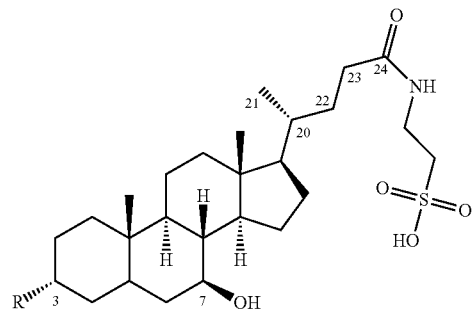
Formula (III)
3-T-R
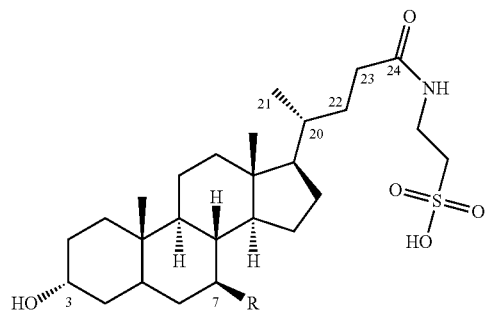
Formula (IV)
7-T-R
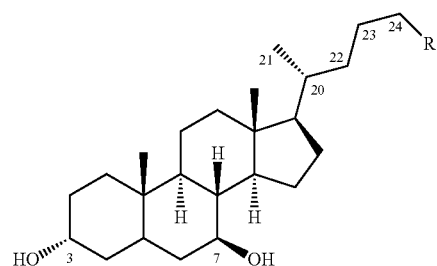
Formula (II)
24-U-R TABLE A-continued
TUDCA/UDCA Dimer:
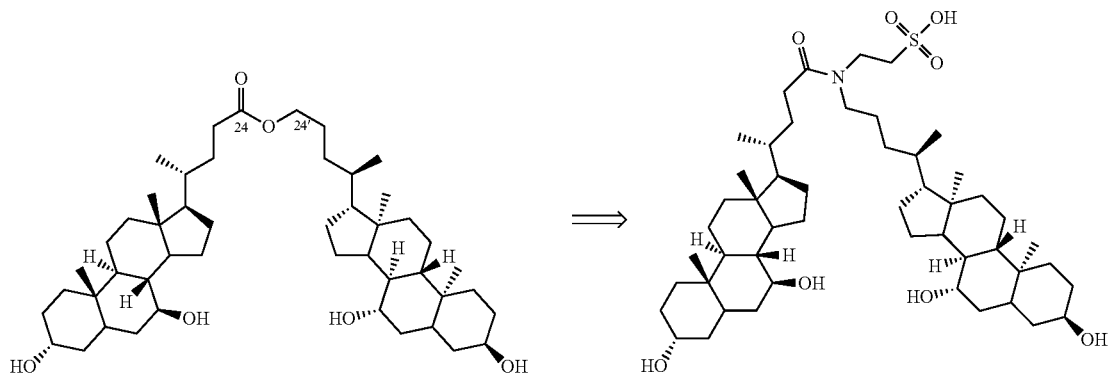
24-DIU
24-Ursodeoxycholyl Ursodeoxycholate
24-UT amide
24-Ursodeoxycholyl Tauroursodeoxycholamide
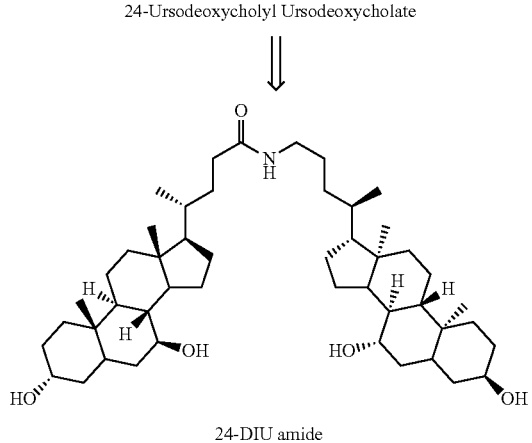
24-DIU amide
24-Ursodeoxycholyl Ursodeoxycholamide
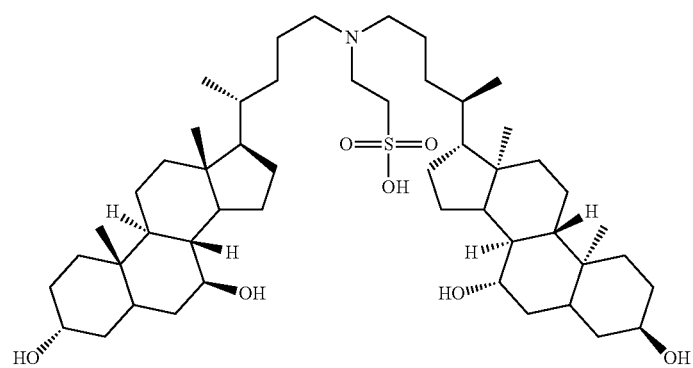
24-UT amine
24-Ursodeoxycholyl Tauroursodeoxycholamine TABLE A-continued
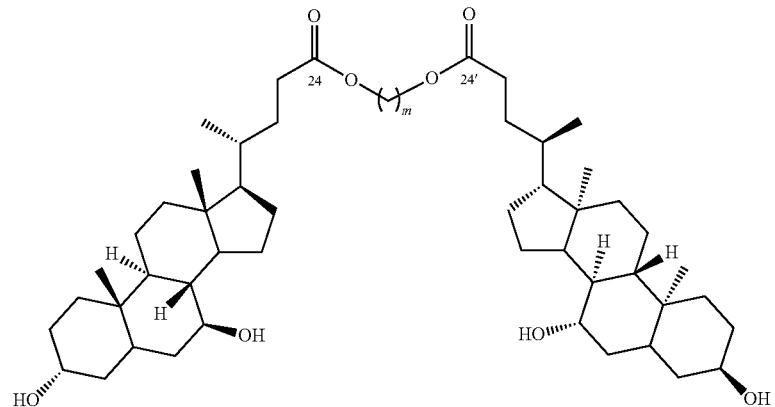
m = 1-7
24-UEU
24-Di-Ursodeoxycholyl-Ester-Ursodeoxycholic acid
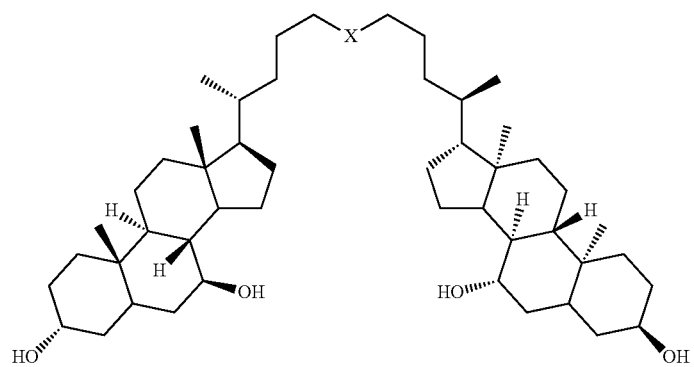
X = NH 24-DIU amine X = O, 24-DIU Ether
24-Ursodeoxycholyl Ursodeoxycholamine
24-Ursodeoxycholyl Ursodeoxycholyl ether
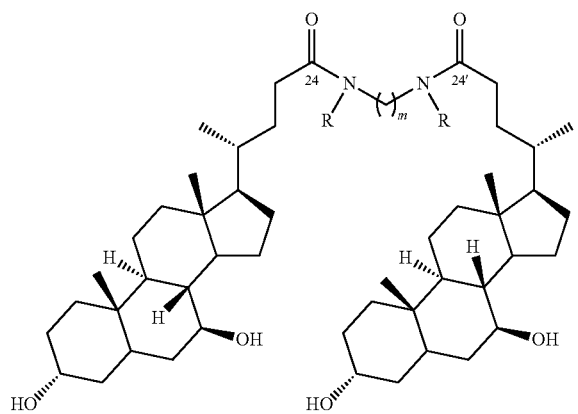
24-UAU
24-Ursodeoxycholyl-Amide-Ursodeoxycholic acid TABLE A-continued
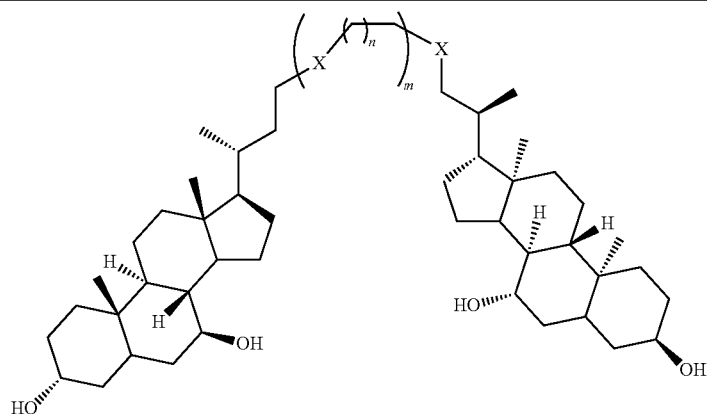
m = 0-7
n = 1-7
X = NH, 24-DIU polyamine
X = O, 24-DIU polyether
Poly-24-Ursodeoxycholyl Ursodeoxycholyl amine
Poly-24-Ursodeoxycholyl Ursodeoxycholyl ether
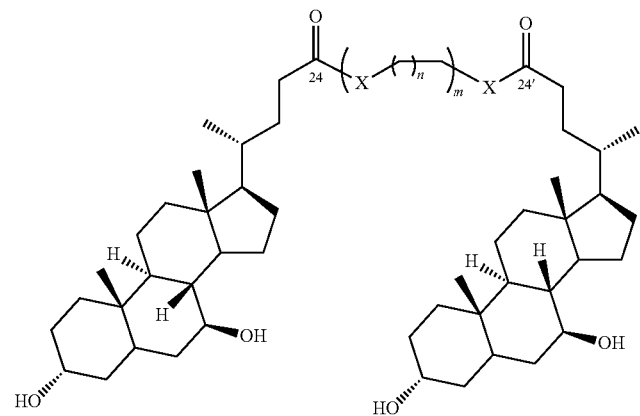
m = 0-7
n = 1-7
X = O, 24-UUPE
X = NR, 24-UUPA
X = NR, 24-Ursodeoxycholyl Ursodeoxycholyl PolyAmide
X = O, 24-Ursodeoxycholyl Ursodeoxycholyl PolyEsterr
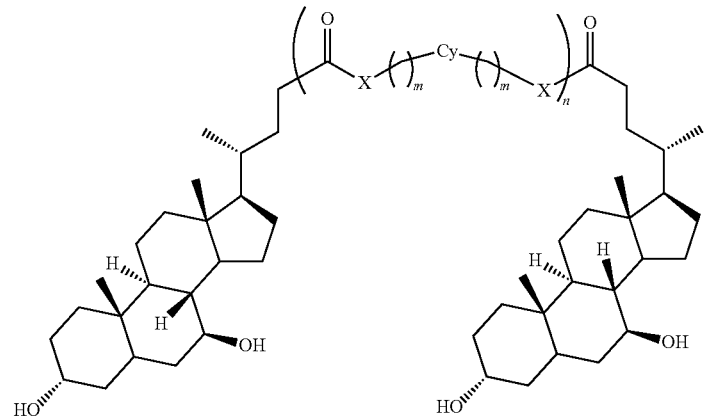
m = 0-7
n = 1-7
X = NR, 24-PHR UU Amide-1
X = O, 24-PHR UU Ester-1

TABLE A-continued

Cy = Saturated or Unsaturated ring system including, any sized Heterocycle or Carbocycles with Cic/Trans; para-, ortho- or meta-substitution

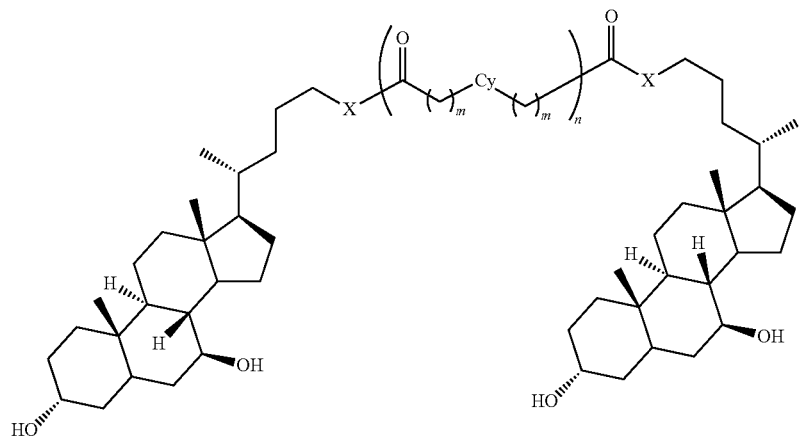

m = 0-7
n = 1-7
X = NR, 24-PHR UU Amide-2
X = O, 24-PHR UU Ester-2
Cy = Saturated or Unsaturated ring system including, any sized Heterocycle or Carbocycles with Cic/Trans; para-, ortho- or meta-substitution

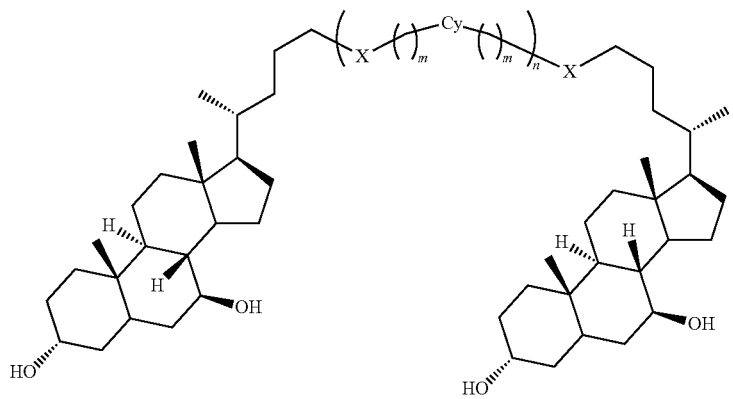

m = 0-7
n = 1-7
X = NR, 24-PPR UU Amine-3
X = O, 24-PPR UU Ether-3
Cy = Saturated or Unsaturated ring system including, any sized Heterocycle or Carbocycles with Cic/Trans; para-, ortho- or meta-substitution

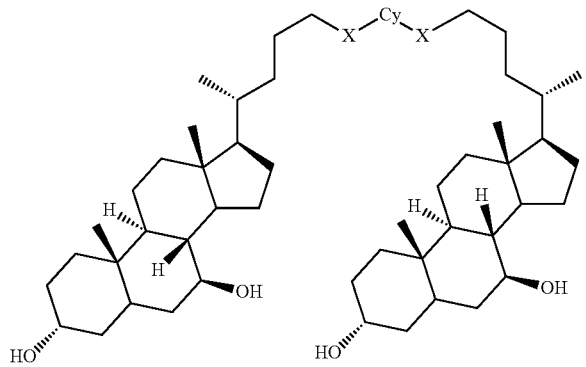

X = NR, 24-PPR UU Amine-4
X = O, 24-PPR UU Ether-4
Cy = Saturated or Unsaturated ring system including, any sized Heterocycle or Carbocycles with Cic/Trans; para-, ortho- or meta-substitution TABLE A-continued
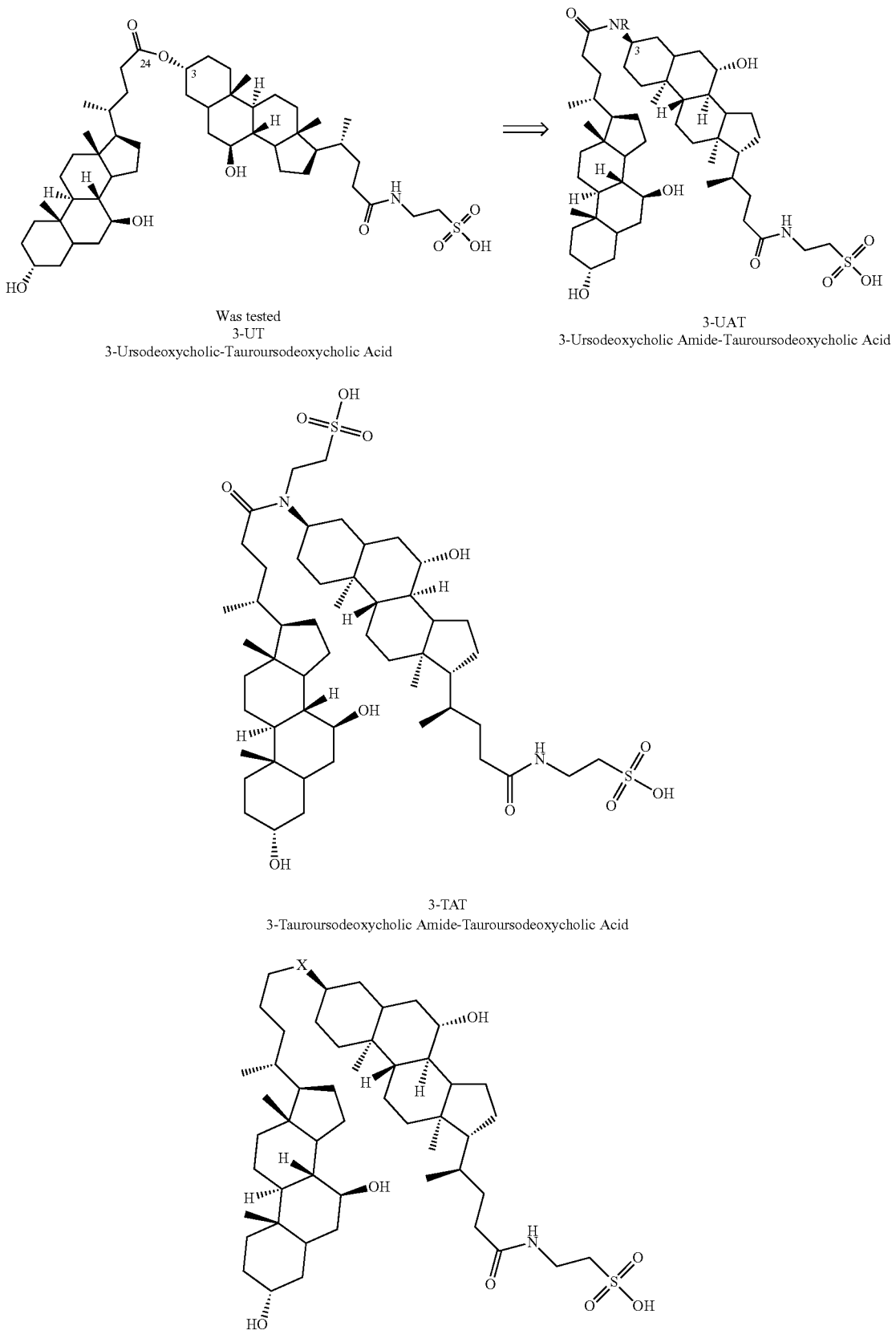
Was tested
3-UT
3-Ursodeoxycholic-Tauroursodeoxycholic Acid
3-UAT
3-Ursodeoxycholic Amide-Tauroursodeoxycholic Acid
3-TAT
3-Tauroursodeoxycholic Amide-Tauroursodeoxycholic Acid TABLE A-continued
X = NR, 3-UT amine
X = O, 3-UT Ether
3-Ursodeoxycholyl Tauroursodeoxycholyl amine
3-Ursodeoxycholyl Tauroursodeoxycholyl ether
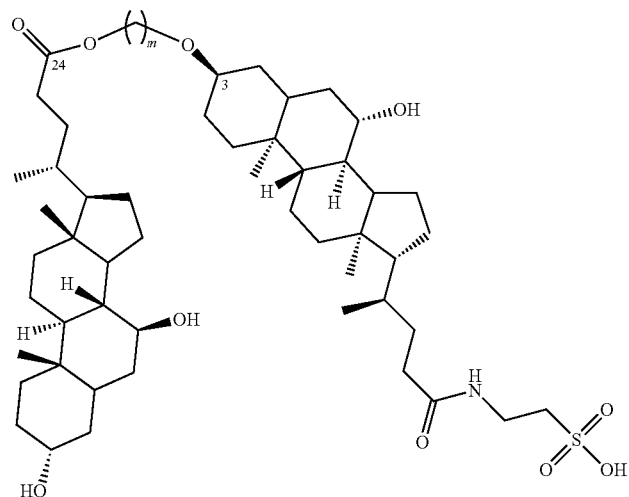
m = 1-7
3-UTE
3-Ursodeoxycholyl Tauroursodeoxycholyl Ester
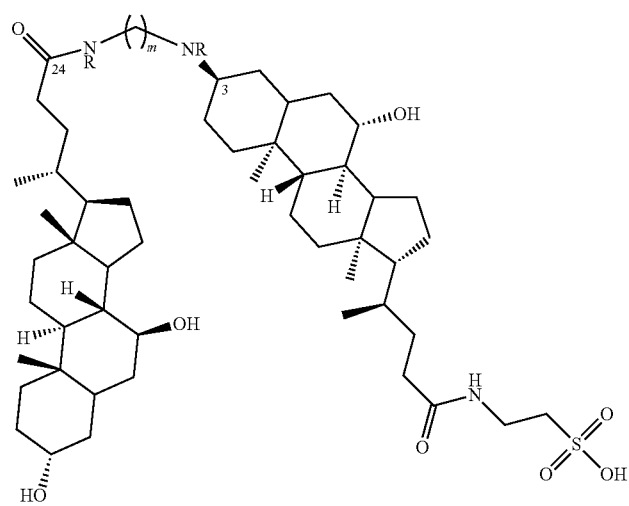
m = 1-7
3-UTA
3-Ursodeoxycholyl Tauroursodeoxycholyl Amide TABLE A-continued
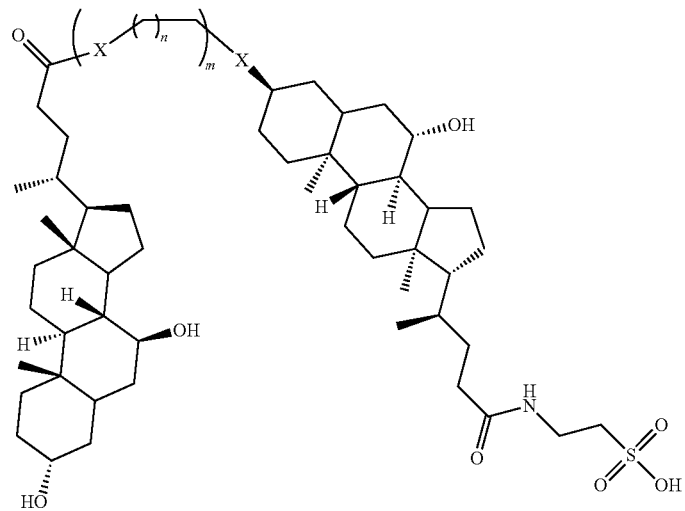
m = 0-7
n = 0-7
X = O, 3-UTPE
X = NR, 3-UTPA
X = NR, 3-Ursodeoxycholyl Tauroursodeoxycholyl PolyAmide
X = O, 3-Ursodeoxycholyl Tauroursodeoxycholyl PolyEsterr
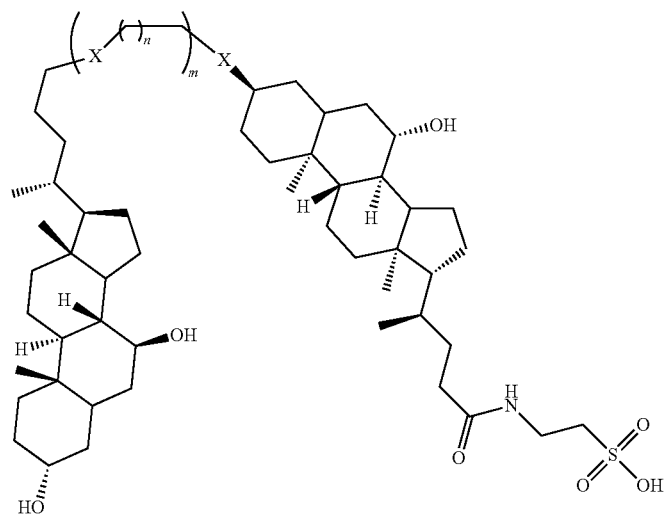
X = O, 3-UTP Ether
X = NR, 3-UTP Amine
X = NR, 3-Ursodeoxycholyl Tauroursodeoxycholyl PolyAmide
X = O, 3-Ursodeoxycholyl Tauroursodeoxycholyl PolyEsterr TABLE A-continued

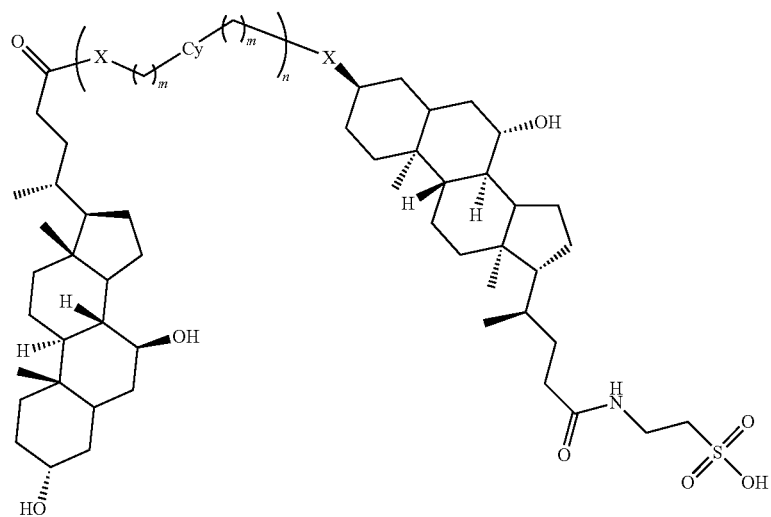

m = 0-7
n = 1-7
X = NR, 3-PPR UT Amide
X = O, 3-PPR UT Ester
Cy = Saturated or Unsaturated ring system including, any sized Heterocycle or
Carbocycles with Cic/Trans; para-, ortho- or meta-substitution

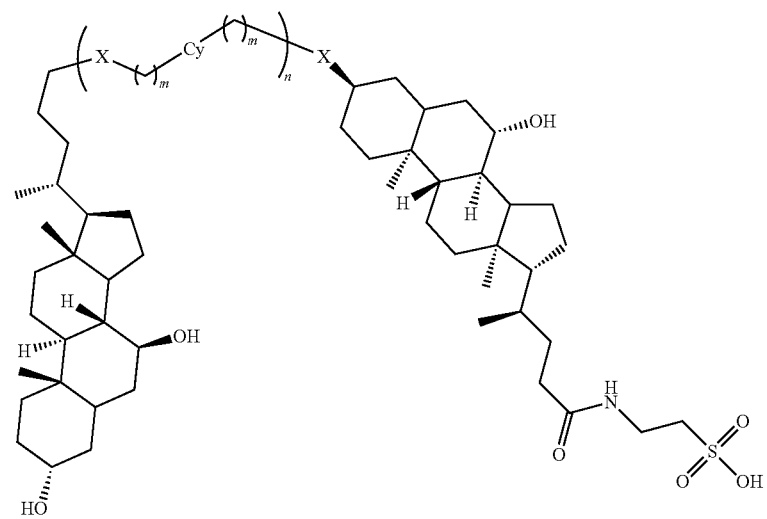

m = 0-7
n = 1-7
X = NR, 3-PPR UT Amine
X = O, 3-PPR UT Ether
Cy = Saturated or Unsaturated ring system including, any sized Heterocycle or
Carbocycles with Cic/Trans; para-, ortho- or meta-substitution

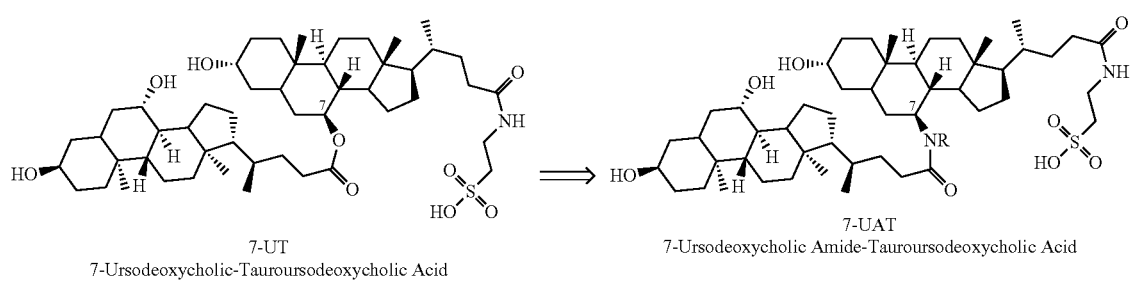

7-UT
7-Ursodeoxycholic-Tauroursodeoxycholic Acid

7-UAT
7-Ursodeoxycholic Amide-Tauroursodeoxycholic Acid

TABLE A-continued
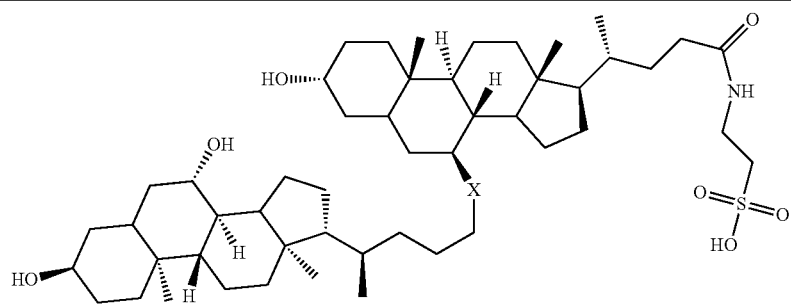
X = NR, 7-UT amine
X = O, 7-UT Ether
7-Ursodeoxycholyl Tauroursodeoxycholyl amine
7-Ursodeoxycholyl Tauroursodeoxycholyl ether
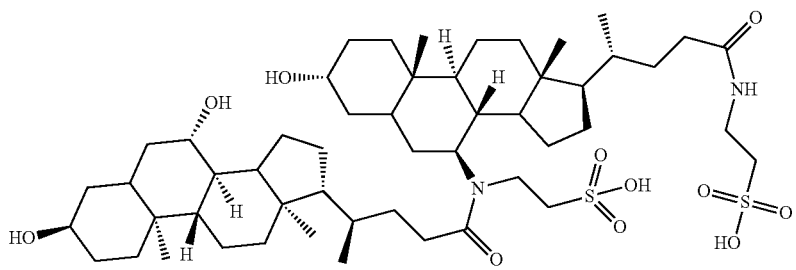
7-TAT
7-Tauroursodeoxycholic Amide-Tauroursodeoxycholic Acid
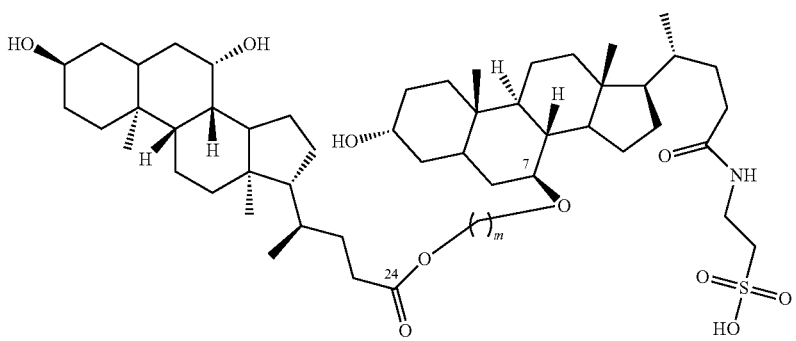
m = 1-7
7-UTE
7-Ursodeoxycholyl Tauroursodeoxycholyl Ester
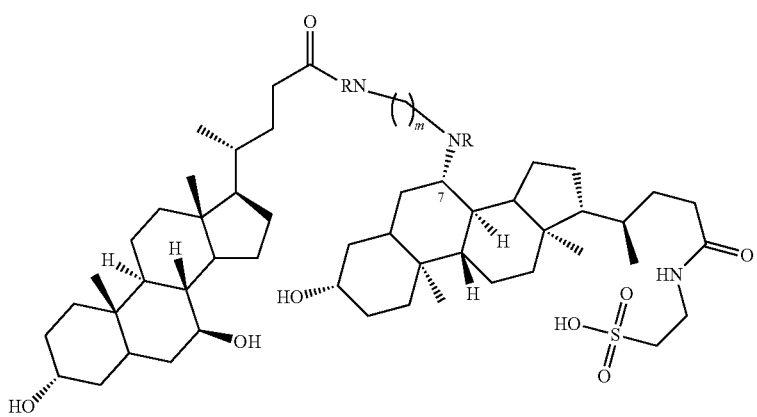
m = 1-7
7-UTA
7-Ursodeoxycholyl Tauroursodeoxycholyl Amide TABLE A-continued

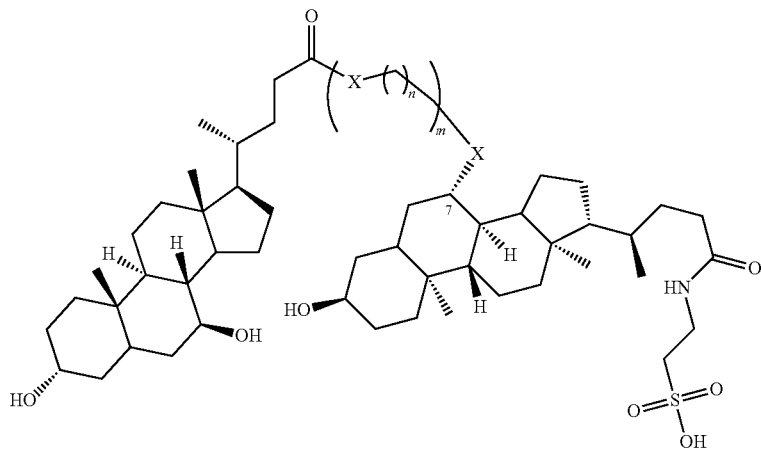

X = O, 7-UTPE
X = NR, 7-UTPA
X = NR, 7-Ursodeoxycholyl Tauroursodeoxycholyl PolyAmide
X = O, 7-Ursodeoxycholyl Tauroursodeoxycholyl PolyEster

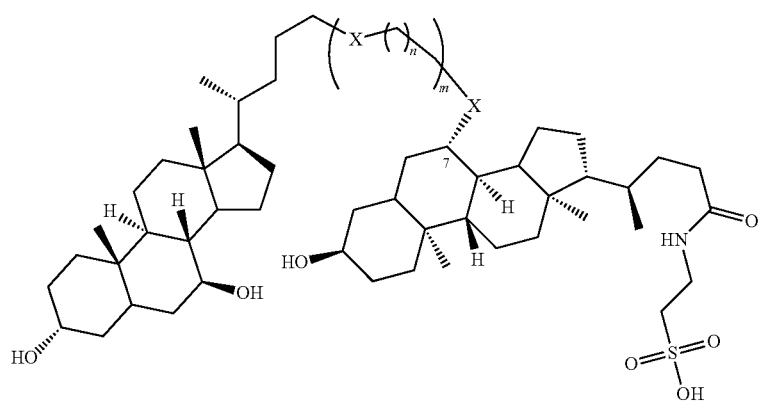

X = O, 7-UTP Ether
X = NR, 7-UTP Amine
X = NR, 7-Ursodeoxycholyl Tauroursodeoxycholyl PolyAmine
X = O, 7-Ursodeoxycholyl Tauroursodeoxycholyl PolyEther

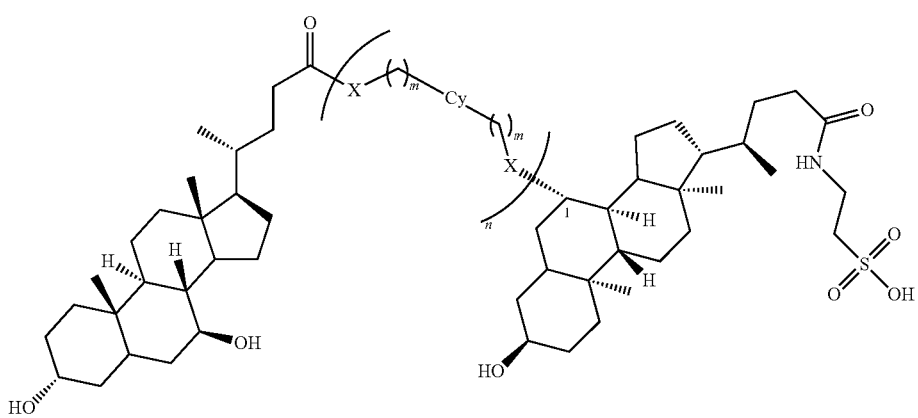

m = 0-7
n = 1-7
X = NR, 7-PHR UT Amide
X = O, 7-PHR UT Ester
Cy = Saturated or Unsaturated ring system including, any sized Heterocycle or Carbocycles with Cic/Trans; para-, ortho- or meta-substitution TABLE A-continued
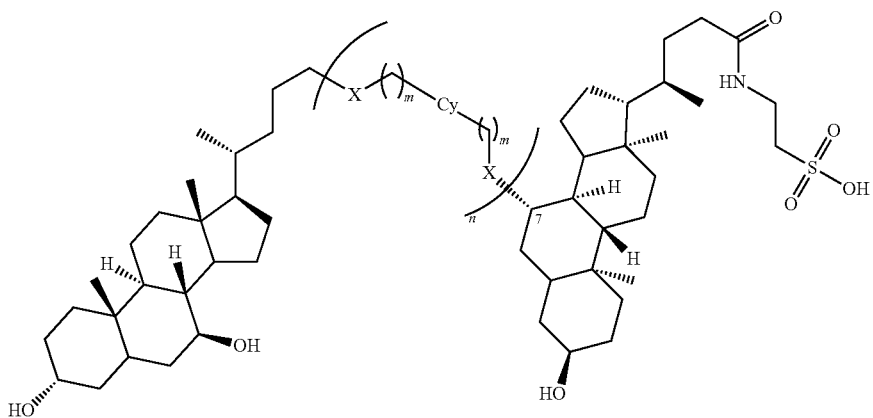
m = 0-7
n = 1-7
X = NR, 7-PPR UT Amine
X = O, 7-PPR UT Ether
Cy = Saturated or Unsaturated ring system including, any sized Heterocycle or Carbocycles with Cic/Trans; para-, ortho- or meta-substitution
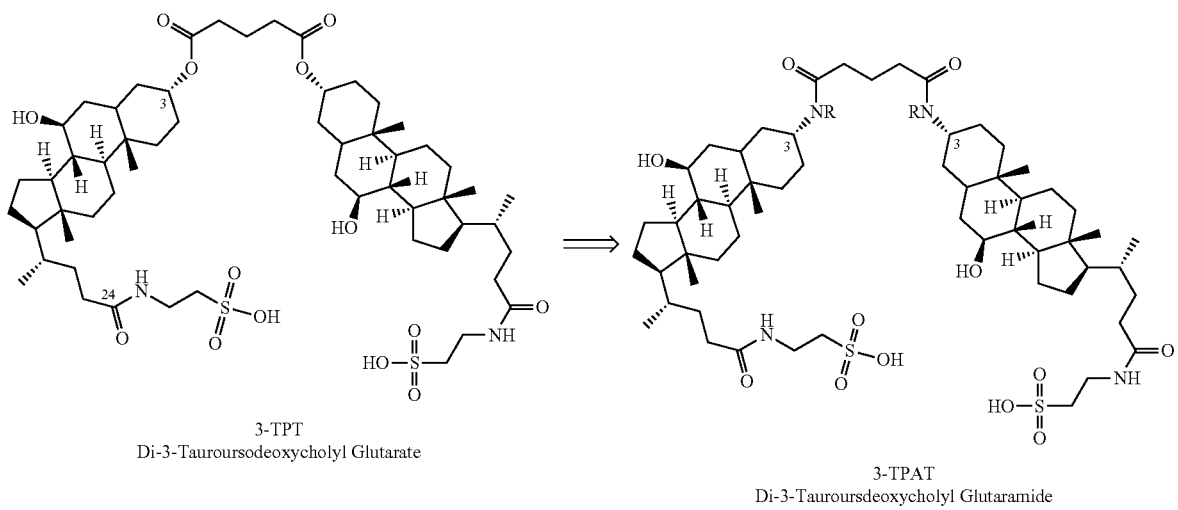
3-TPT
Di-3-Tauroursodeoxycholyl Glutarate
3-TPAT
Di-3-Tauroursdeoxycholyl Glutaramide
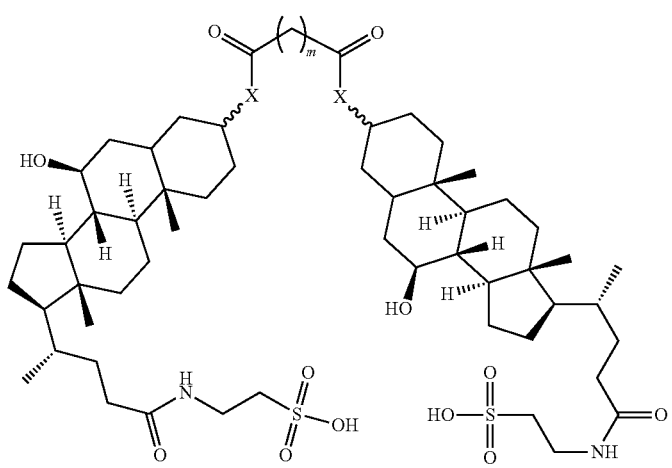
m = 1-7
X = NR, 3-RTT Amide
X = O, 3-RTT Ester TABLE A-continued
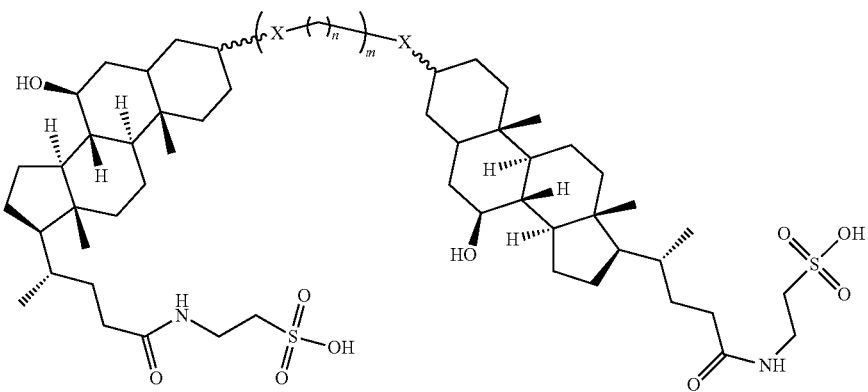
m = 0-5
n = 0-5
X = O, 3-RTTPE
X = NR, 3-RTTPA
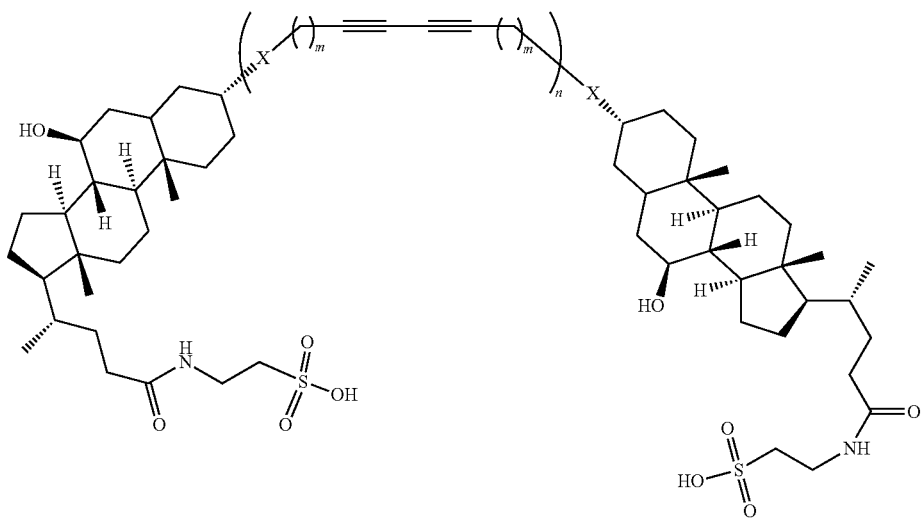
m = 0-7
n = 1-7
X = NR, 3-Polyalkyne Tauroursodeoxycholyl Tauroursodeoxycholyl Amine
X = O, 3-Polyalkyne Tauroursodeoxycholyl Tauroursodeoxycholyl Ester
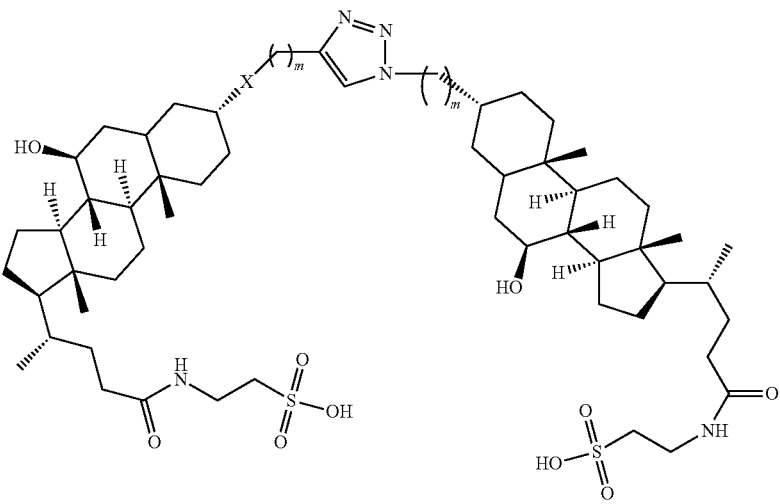

TABLE A-continued m = 0-7
3-Triazole TT Ether
3-Triazole Tauroursodeoxycholyl Tauroursodeoxycholyl Ether

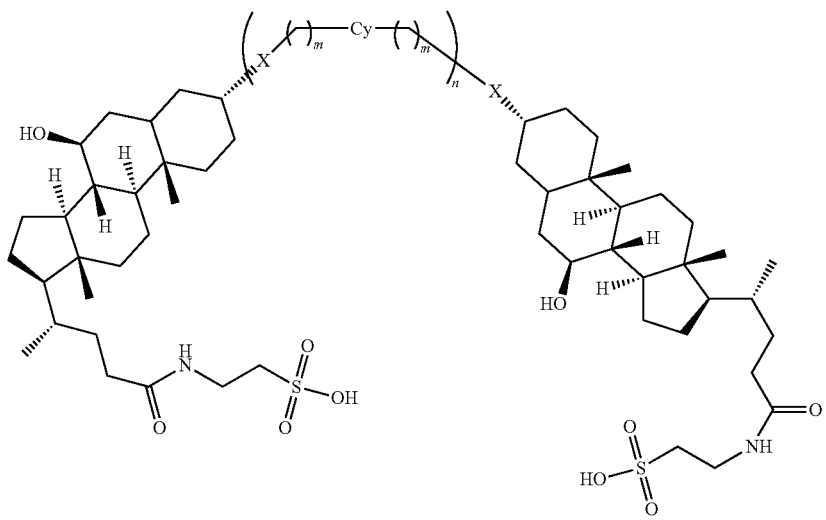

m = 0-7
n = 1-7
X = NR, 3-PHR TT Amine
X = O, 3-PHR TT Ether
Cy = Saturated or Unsaturated ring system including, any sized Heterocycle or Carbocycles with Cic/Trans; para-, ortho- or meta-substitution

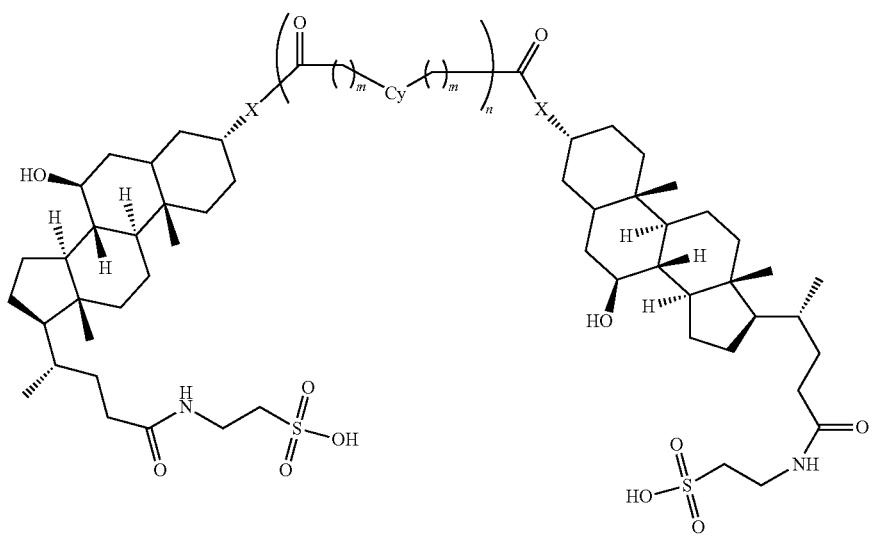

m = 0-7
n = 1-7
X = NR, 3-PHR TT Amide
X = O, 3-PHR TT Ester
Cy = Saturated or Unsaturated ring system including, any sized Heterocycle or Carbocycles with Cic/Trans; para-, ortho- or meta-substitution TABLE A-continued
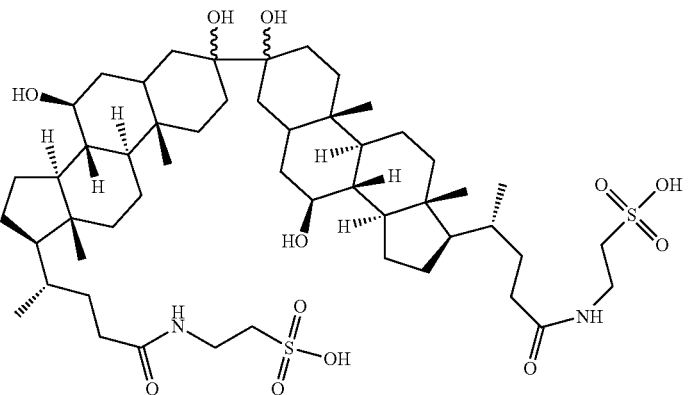
3-Diol TT
3-Diol Tauroursodeoxycholyl Tauroursodeoxycholyl
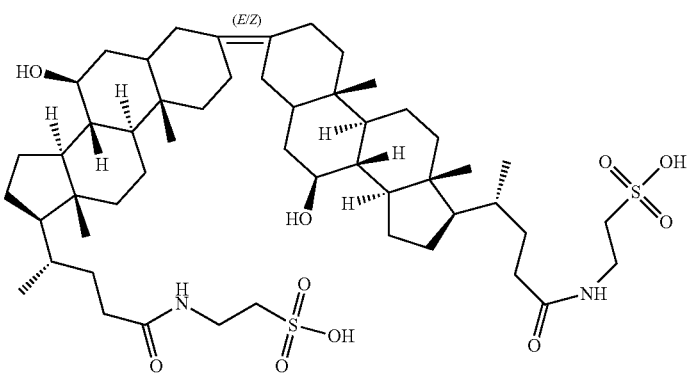
3-Alkene(E/Z) TT
3-Alkene(E/Z) Tauroursodeoxycholyl Tauroursodeoxycholyl
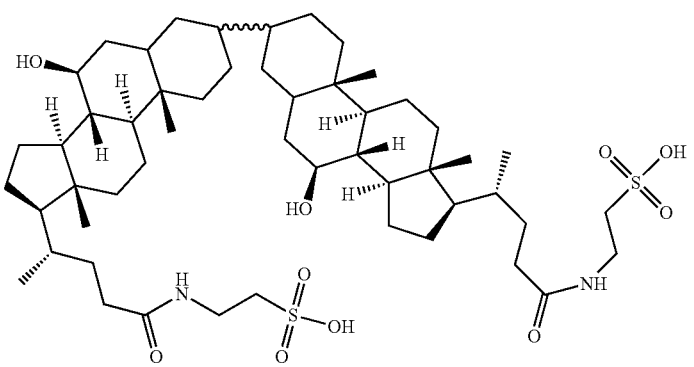
3-TT
3-Tauroursodeoxycholyl Tauroursodeoxycholyl TABLE A-continued

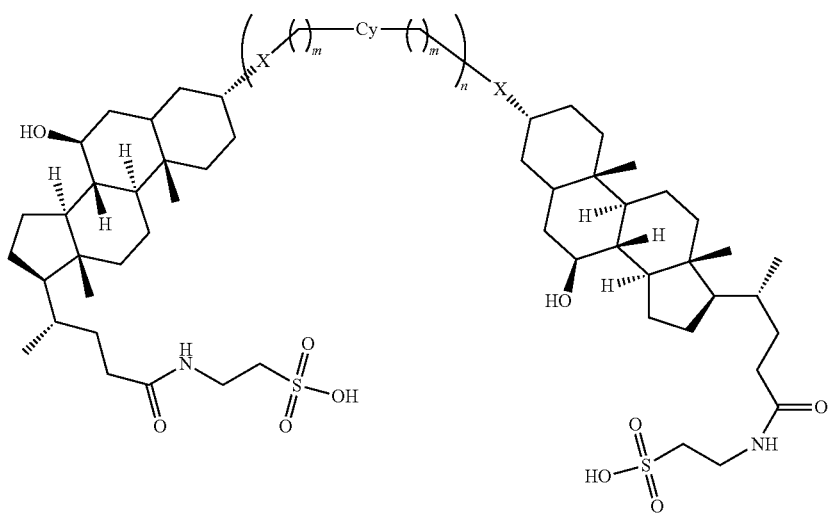

m = 0-7
n = 1-7
X = NR, 3-PHepR TT Amine
X = O, 3-PHepR TT Ether
Cy = Saturated or Unsaturated ring system including, any sized Heterocycle or Carbocycles with Cic/Trans; para-, ortho- or meta-substitution

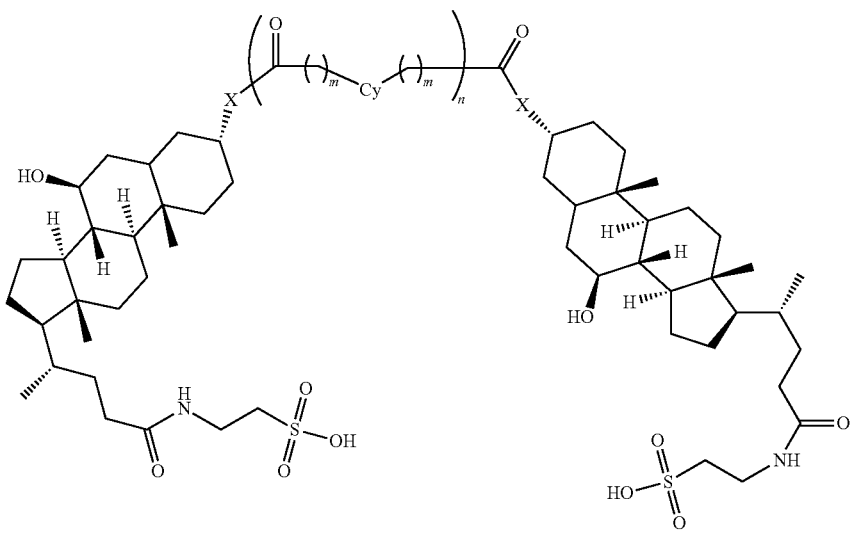

m = 0-7
n = 1-7
X = NR, 3-PHepR TT Amide
X = O, 3-PHepR TT Ester
Cy = Saturated or Unsaturated ring system including, any sized Heterocycle or Carbocycles with Cic/Trans; para-, ortho- or meta-substitution TABLE A-continued
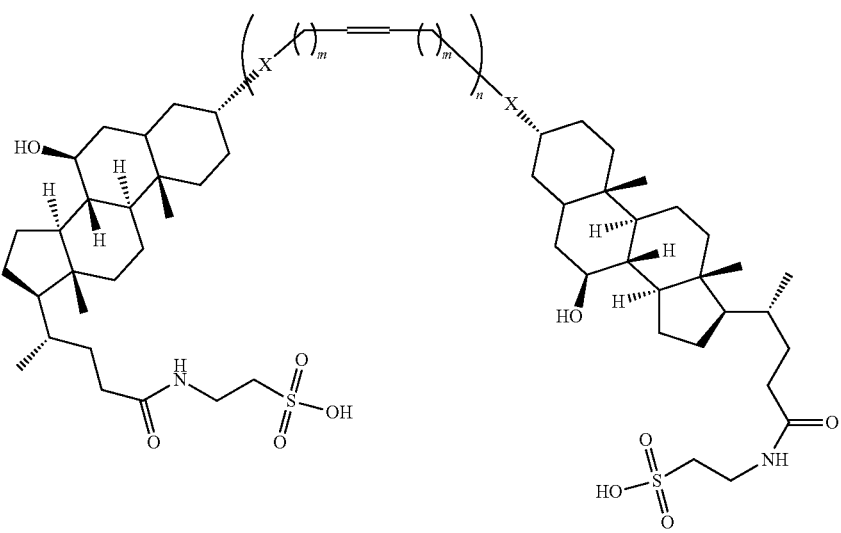
m = 0-7
n = 1-7
X = NR, 3-Polyalkene-Tauroursodeoxycholyl Tauroursodeoxycholyl Amine
X = O, 3-Polyalkene-Tauroursodeoxycholyl Tauroursodeoxycholyl Ether
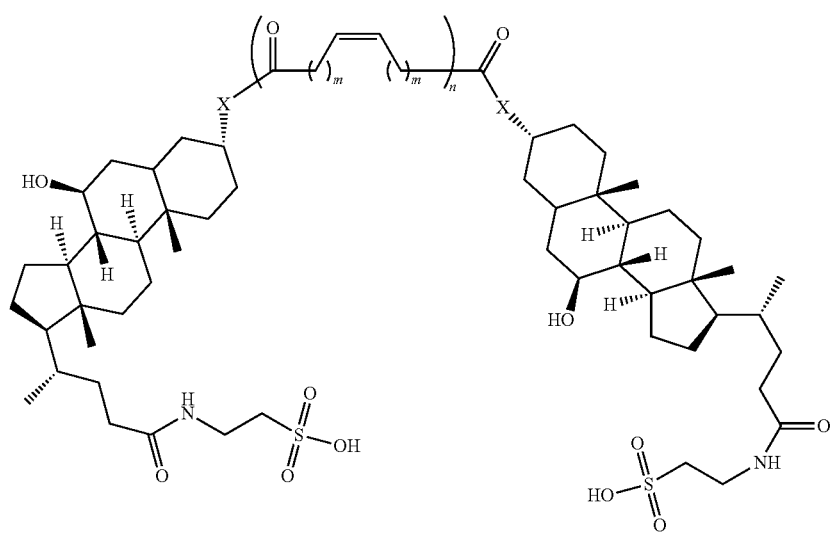
m = 0-7
n = 1-7
X = NR, 3-PTne TT Amide
X = O, 3-PYne TT Ester
X = NR, 3-Polyalkene-Tauroursodeoxycholyl Tauroursodeoxycholyl Amide
X = O, 3-Polyalkene-Tauroursodeoxycholyl Tauroursodeoxycholyl Ester TABLE A-continued
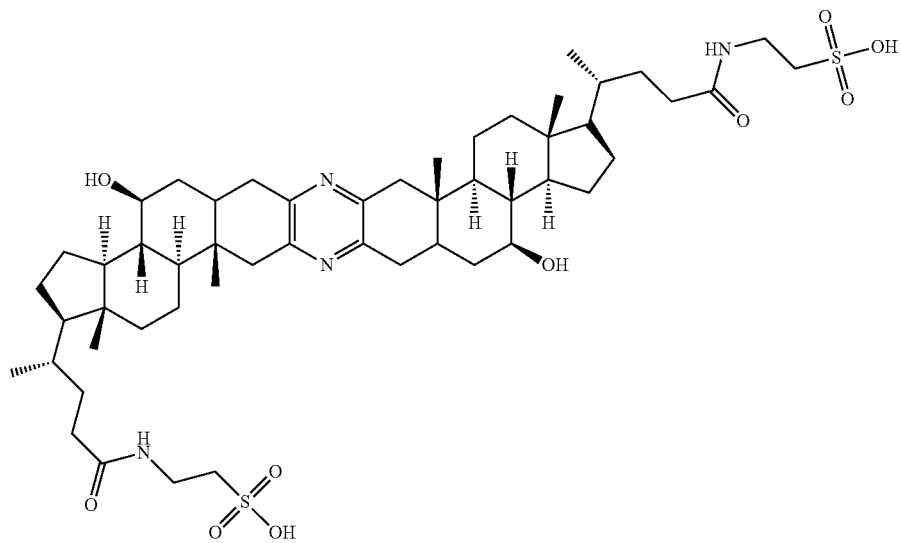
2,3-pyrazine TT
2,3-pyrazine Tauroursodeoxycholyl Tauroursodeoxycholyl
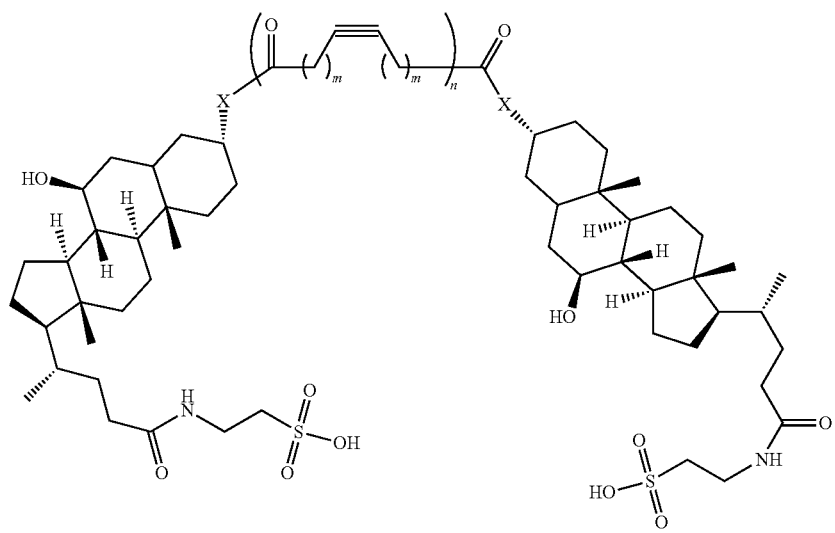
m = 0-7
n = 1-7
X = NR, 3-PAlkyne TT Amide
X = O, 3-PAlkyne TT Ester
X = NR, 3-Polyalkyne-Tauroursodeoxycholyl Tauroursodeoxycholyl Amide
X = O, 3-Polyalkyne-Tauroursodeoxycholyl Tauroursodeoxycholyl Ester TABLE A-continued

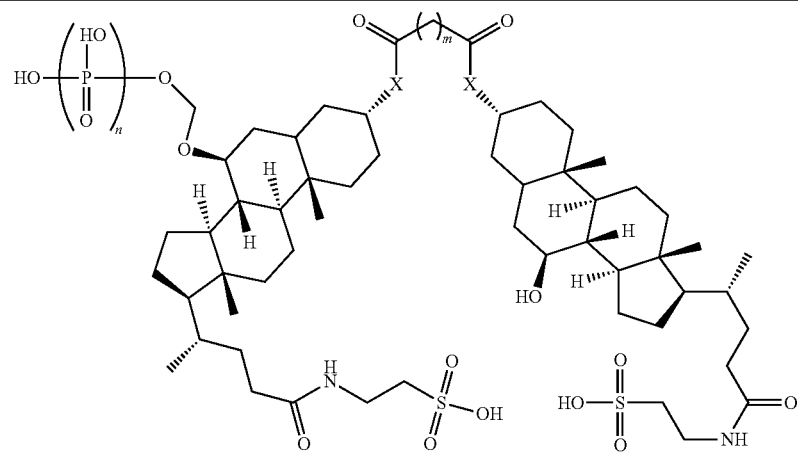

m = 1-7
n = 1-3
X = NR, 3-(7-PPhosphate)TT Amide
X = O, 3-(7-PPhosphate)TT Ester
3-(7-PolyPhosphate)tauroursodeoxycholyl Tauroursodeoxycholyl Amide
3-(7-PolyPhosphate)tauroursodeoxycholyl Tauroursodeoxycholyl Ester

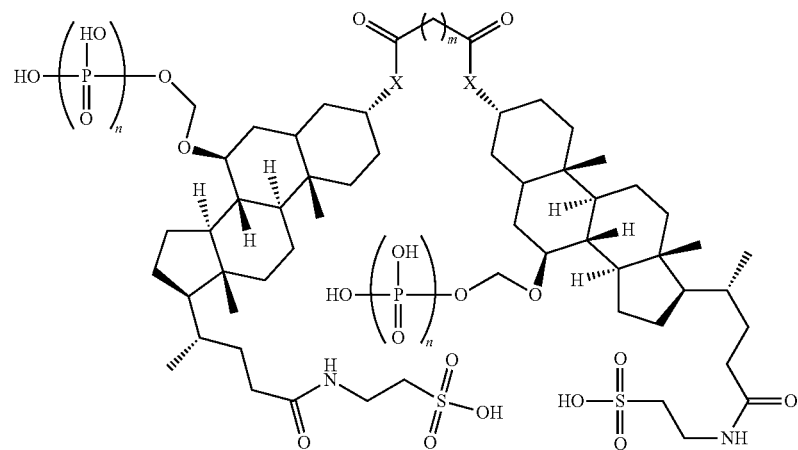

m = 1-7
n = 1-3
X = NR, 3-(7-PDiphosphate)TT Amide
X = O, 3-(7-PDiphosphate)TT Ester
3-(7-PolyDiphosphate)tauroursodeoxycholyl Tauroursodeoxycholyl Amide
3-(7-PolyDiphosphate)tauroursodeoxycholyl Tauroursodeoxycholyl Ester

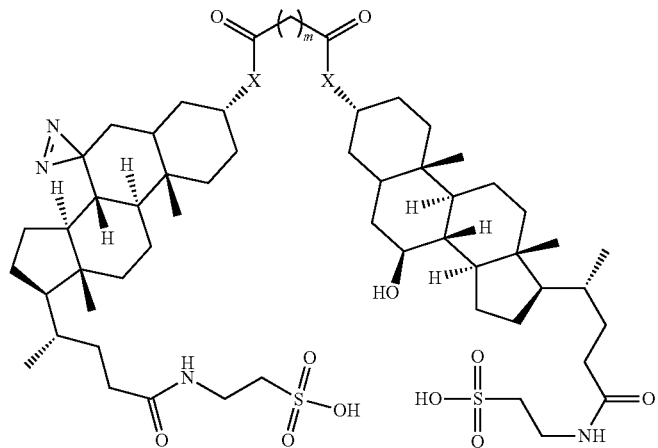

TABLE A-continued m = 1-7
X = NR, 3-(7-Diz)TT Amide
X = O, 3-(7-Diz)TT Ester
3-(7-Diz)tauroursodeoxycholyl Tauroursodeoxycholyl Amide
3-(7-Diz)tauroursodeoxycholyl Tauroursodeoxycholyl Ester

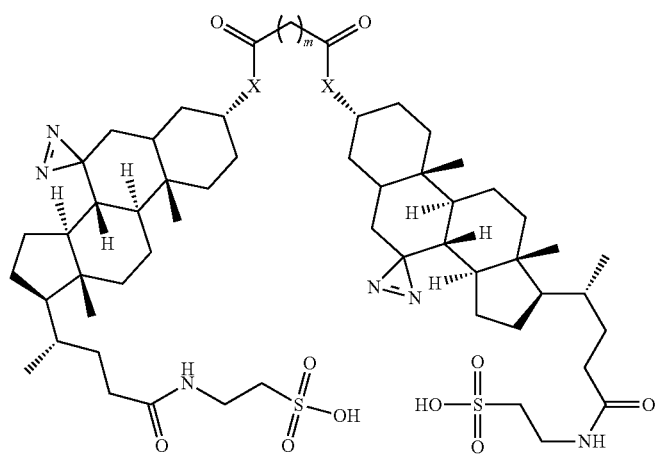

m = 1-7
X = NR, 3-(7-Didiz)TT Amide
X = O, 3-(7-Didiz)TT Ester
3-(7-Didiz)tauroursodeoxycholyl Tauroursodeoxycholyl Amide
3-(7-Didiz)tauroursodeoxycholyl Tauroursodeoxycholyl Ester

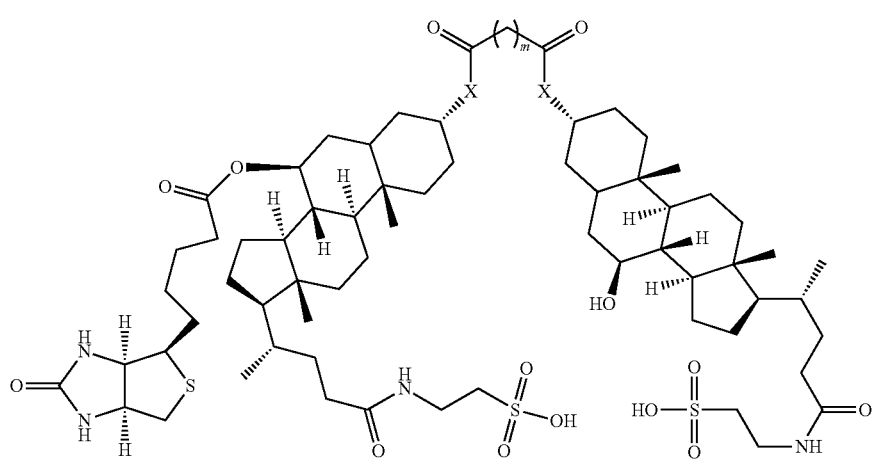

m = 1-7
X = NR, 3-(7-Bio)TT Amine
X = O, 3-(7-Bio)TT Ester
3-(7-Bio-7'-Diz)tauroursodeoxycholyl Tauroursodeoxycholyl Amide
3-(7-Bio-7'-Diz)tauroursodeoxycholyl Tauroursodeoxycholyl Ester

TABLE A-continued
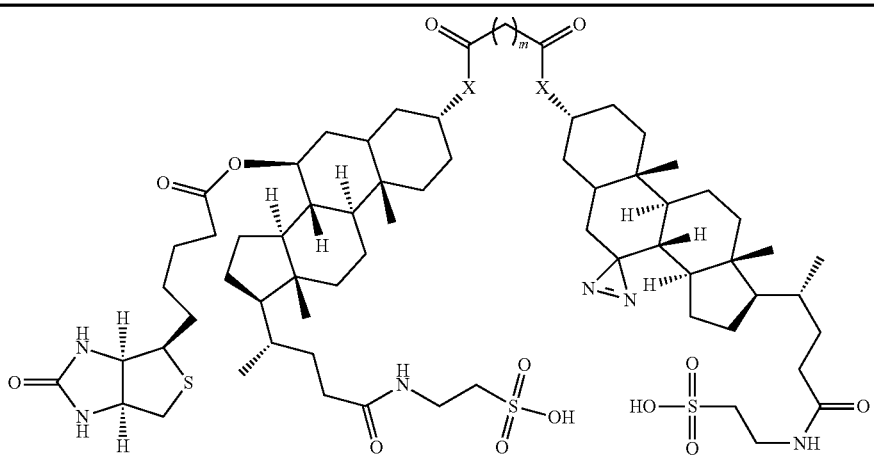
m = 1-7
X = NR, 3-(7-Bio-7'-Diz)TT Amine
X = O, 3-(7-Bio-7'-Diz)TT Ester
3-(7-Bio-7'-Diz)tauroursodeoxycholyl Tauroursodeoxycholyl Amide
3-(7-Bio-7'-Diz)tauroursodeoxycholyl Tauroursodeoxycholyl Ester
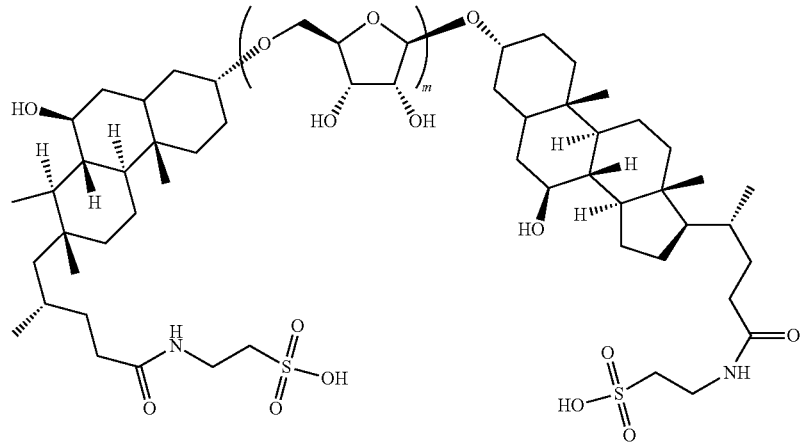
m = 1-7
3-PRibose TT Ether
3-PolyRibose-Tauroursodeoxycholyl Tauroursodeoxycholyl Ether
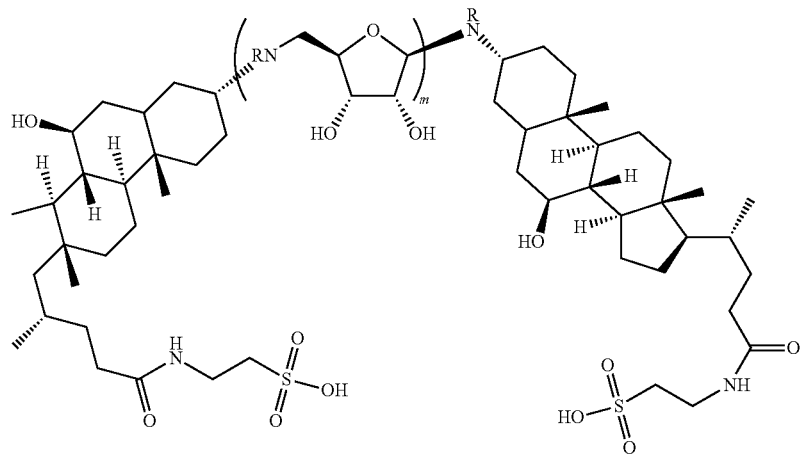
m = 1-7
3-PRibose TT Amine
3-PolyRibose-Tauroursodeoxycholyl Tauroursodeoxycholyl Amine TABLE A-continued

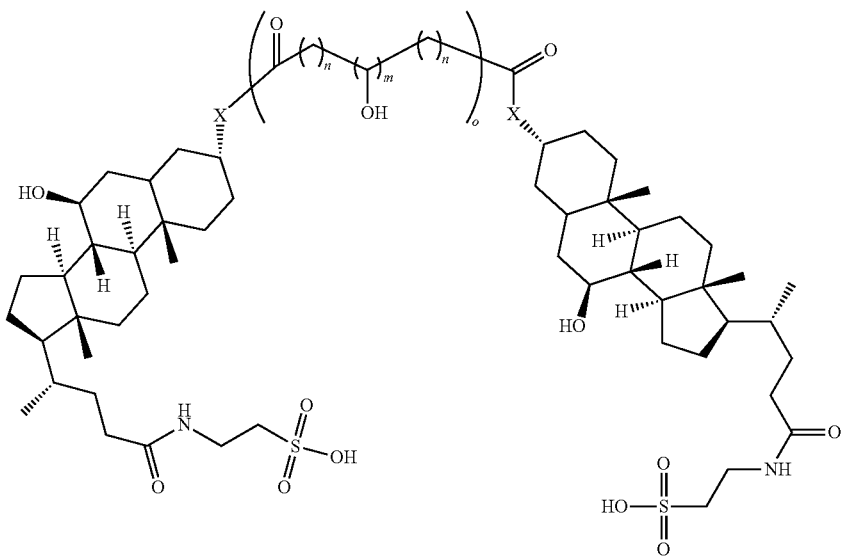

m = 1-7
n = 0-7
o = 1-7
X = NR, 3-Polyol TT Amide
X = O, 3-Polyol TT Ester
X = NR, 3-Polyol-Tauroursodeoxycholyl Tauroursodeoxycholyl Amide
X = O, 3-Polyol-Tauroursodeoxycholyl Tauroursodeoxycholyl Ester

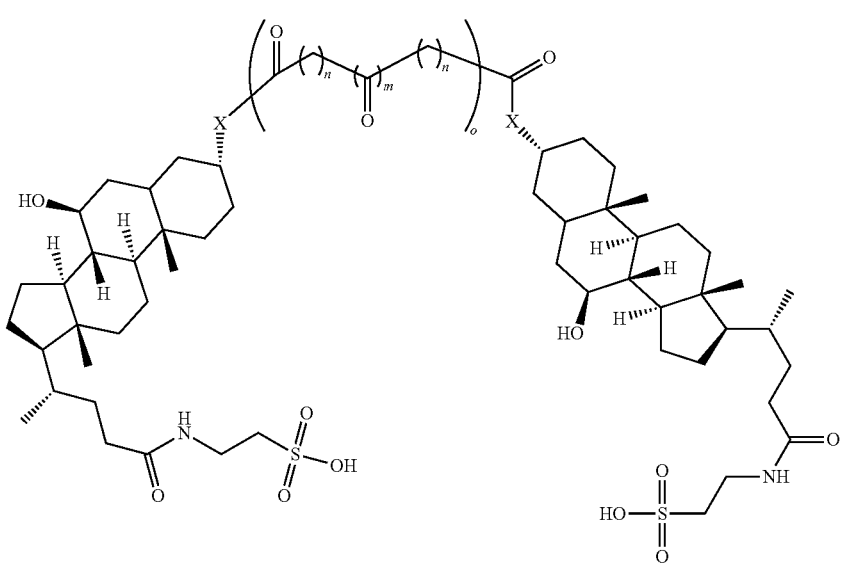

m = 1-7
n = 0-7
o = 1-7
X = NR, 3-Polyone TT Amide
X = O, 3-Polyone TT Ester
X = NR, 3-Polyone-Tauroursodeoxycholyl Tauroursodeoxycholyl Amide
X = O, 3-Polyone-Tauroursodeoxycholyl Tauroursodeoxycholyl Ester TABLE A-continued
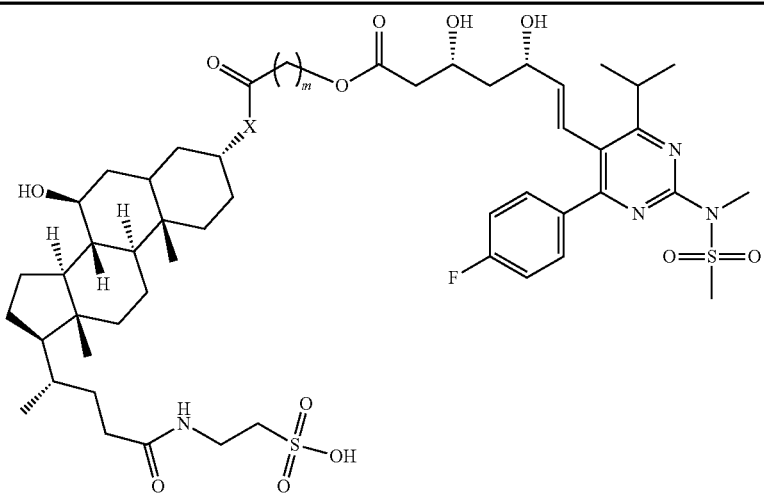
m = 1-7
X = NR, 3-T Rosuvastatin Amide
X = O, 3-T Rosuvastatin Ester
X = NR, 3-Tauroursodeoxycholyl Rosuvastatin Amide
X = O, 3-Tauroursodeoxycholyl Rosuvastatin Ester
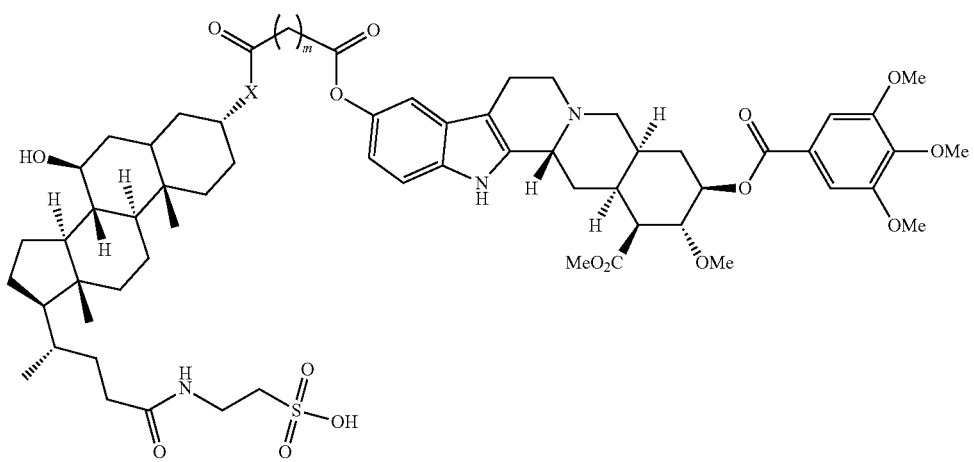
m = 1-7
X = NR, 3-T Reserpine Amide
X = O, 3-T Reserpine Ester
X = NR, 3-Tauroursodeoxycholyl Reserpine Amide
X = O, 3-Tauroursodeoxycholyl Reserpine Ester
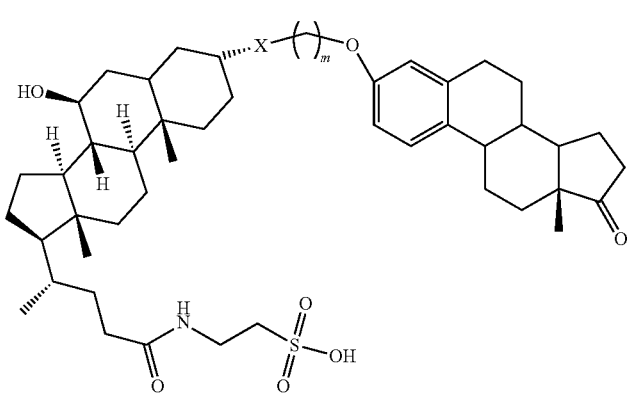
m = 1-5
X = NR, 3-TToestrone Amine
X = O, 3-TToestrone Ether TABLE A-continued X = NR, 3-TauroUrsodeoxycholyl Toestrone Amine
X = O, 3-TauroUrsodeoxycholyl Toestrone Ether

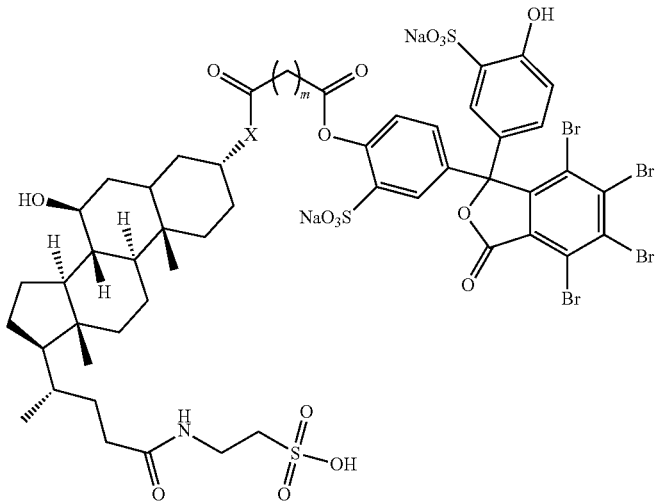

m = 1-7
X = NR, 3-T Bromsulphthalein Amide
X = O, 3-T Bromsulphthalein Ester
X = NR, 3-Tauroursodeoxycholyl Bromsulphthalein Amide
X = O, 3-Tauroursodeoxycholyl Bromsulphthalein Ester

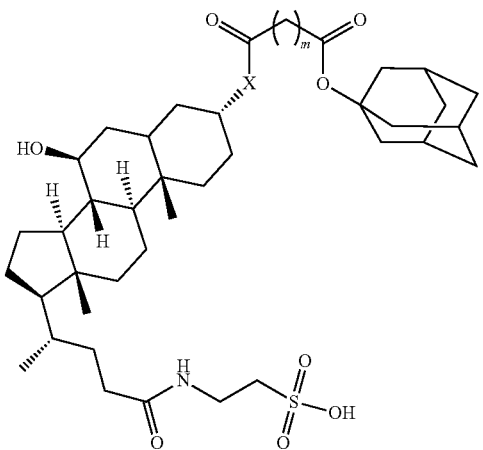

m = 1-7
X = NR, 3-T Adamantanol Amide
X = O, 3-T Adamantanol Ester
X = NR, 3-Tauroursodeoxycholyl Adamantanol Amide
X = O, 3-Tauroursodeoxycholyl Adamantanol Ester

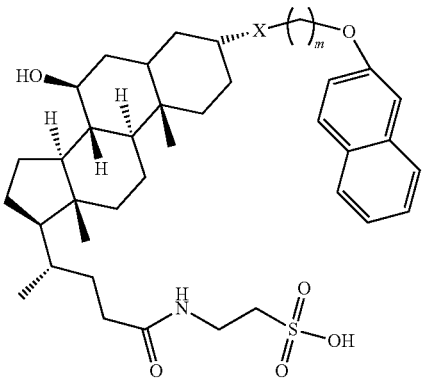

m = 1-5
X = NR, 3-T Naphthalene Amine
X = O, 3-T Naphthalene Ether
X = NR, 3-TauroUrsodeoxycholyl Naphthalene Amine
X = O, 3-TauroUrsodeoxycholyl Naphthalene Ether

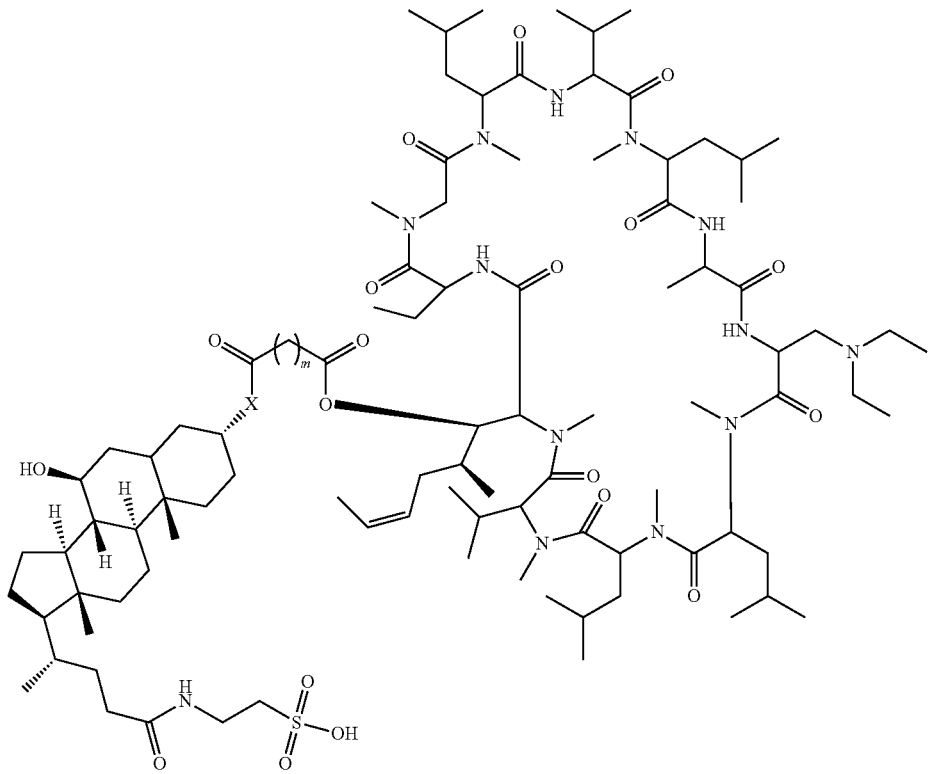

m = 1-7
X = NR, 3-T CsA Amide
X = O, 3-T Csa Ester
X = NR, 3-Tauroursodeoxycholyl CsA Amide
X = O, 3-Tauroursodeoxycholyl CsA Ester

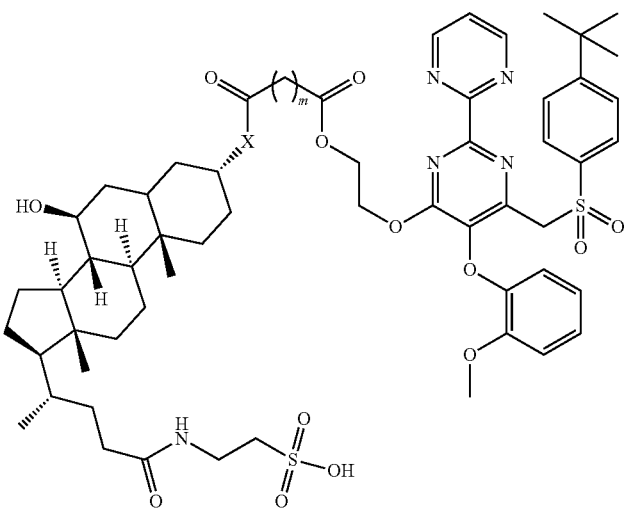

m = 1-7
X = NR, 3-T Bosentan Amide
X = O, 3-T Bosentan Ester
X = NR, 3-Tauroursodeoxycholyl Bosentan Amide
X = O, 3-Tauroursodeoxycholyl Bosentan Ester TABLE A-continued
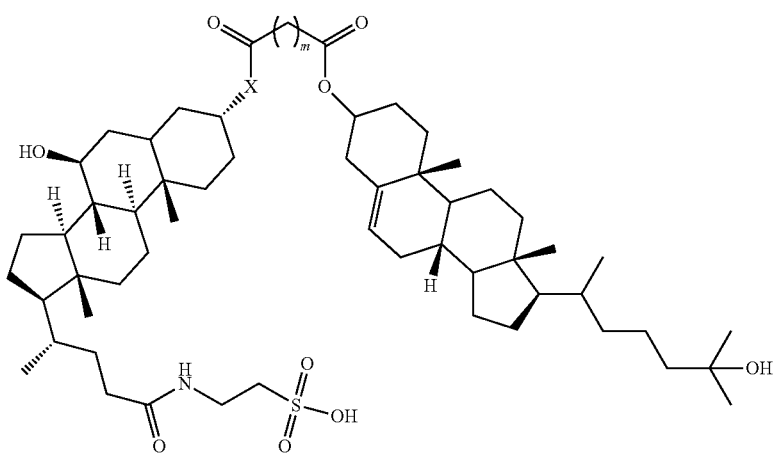
m = 1-7
X = NR, 3-T Oxysterol Amide
X = O, 3-T Oxysterol Ester
X = NR, 3-Tauroursodeoxycholyl Oxysterol Amide
X = O, 3-Tauroursodeoxycholyl Oxysterol Ester
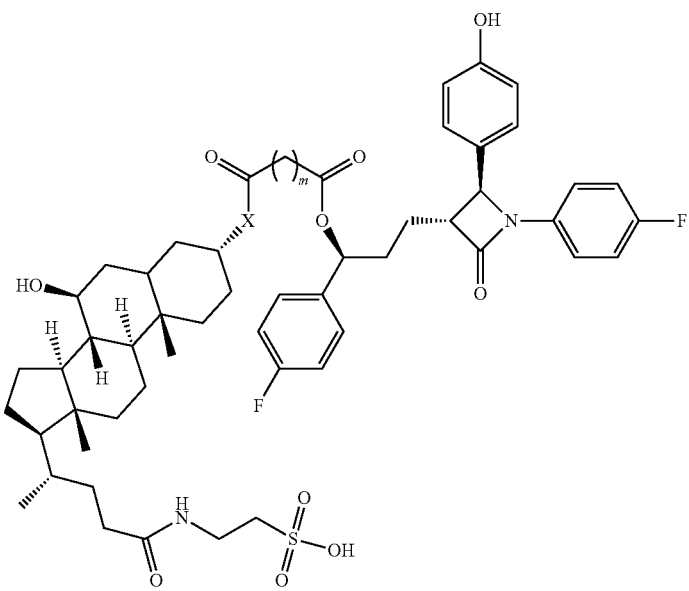
m = 1-7
X = NR, 3-T Ezetimibe Amide
X = O, 3-T Ezetimibe Ester
X = NR, 3-Tauroursodeoxycholyl Ezetimibe Amide
X = O, 3-Tauroursodeoxycholyl Ezetimibe Ester TABLE A-continued

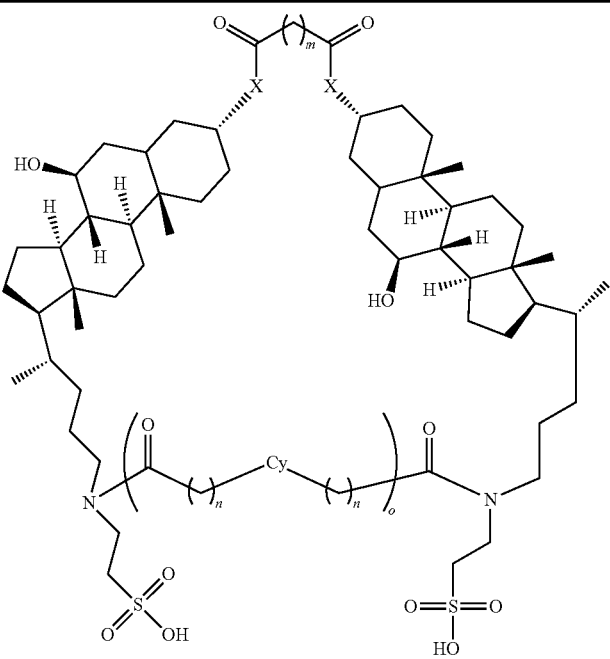

m = 1-7
n = 0-7
o = 1-7
X = NR, 3-(24-Polycyclic Lactam)TauroUrsodeoxycholyl
Tauroursodeoxycholyl Amide
X = O, 3-(24-Polycyclic Lactam)TauroUrsodeoxycholyl
Tauroursodeoxycholyl Ester
Cy = Saturated or Unsaturated ring system including, any sized Heterocycle or
Carbocycles with Cic/Trans; para-, ortho- or meta-substitution

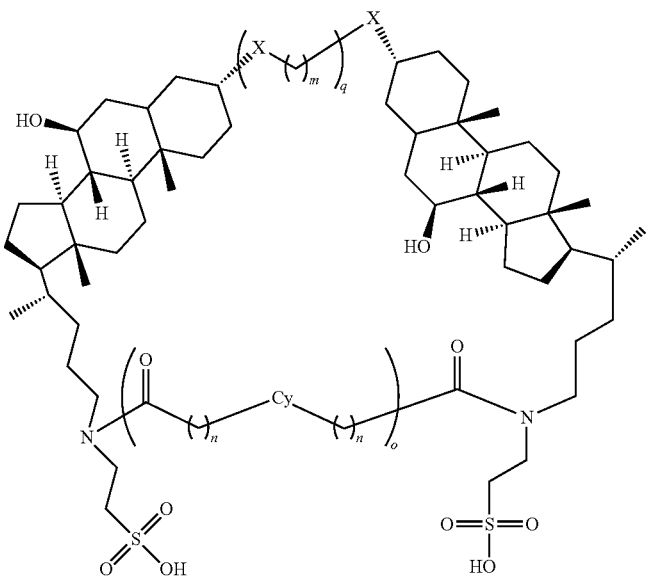

m = 1-7
n = 0-7
o = 1-7
q = 1-7
X = NR, 3-(24-PPRLactam)TT Amine
X = O, 3-(24-PPRLactam)TT Ether
Cy = Saturated or Unsaturated ring system including, any sized Heterocycle or
Carbocycles with Cic/Trans; para-, ortho- or meta-substitution TABLE A-continued

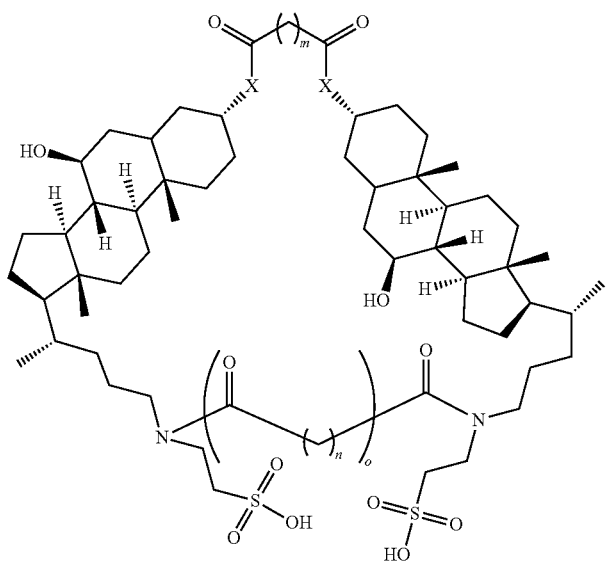

n = 0-7
o = 1-7
m = 1-7
X = NR, 3-(24-PLactam)TT Amide
X = O, 3-(24-PLactam)TT Ester
X = NR, 3-(24-PolyLactam)TauroUrsodeoxycholyl Tauroursodeoxycholyl Amide
X = O, 3-(24-PolyLactam)TauroUrsodeoxycholyl Tauroursodeoxycholyl Ester

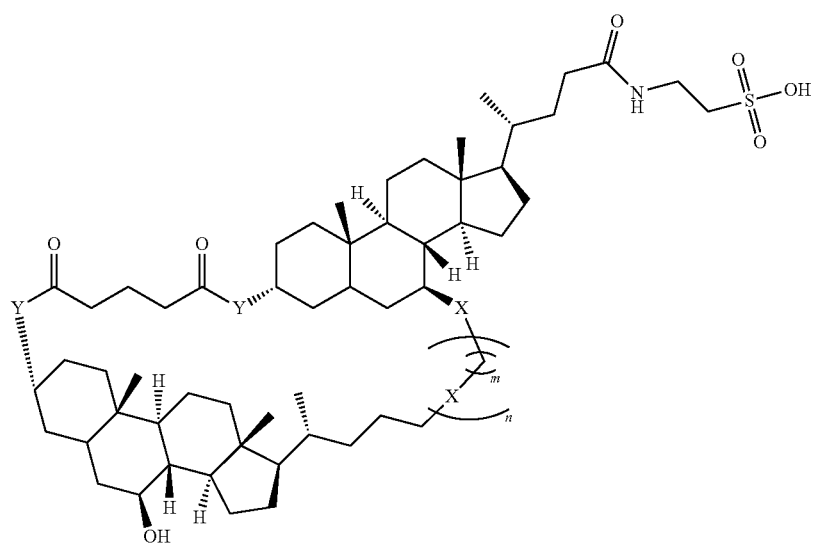

m = 1-7
n = 1-7
X = O, Y = NR, 3-(7,24'-PolyEther)UT Amide
X = NR, Y = O, 3-(7,24'-PolyAmine)UT Ester
X = O, Y = O, 3-(7,24'-PolyEther)UT Ester
X = NR, Y = NR, 3-(7,24'-PolyAmine)UT Amide
X = O, Y = NR, 3-(7,24'-PolyEther)Ursodeoxycholyl Tauroursodeoxycholyl Amide
X = O, Y = NR, 3-(7,24'-PolyAmine)Ursodeoxycholyl Tauroursodeoxycholyl Ester
X = O, Y = NR, 3-(7,24'-PolyEther)Ursodeoxycholyl Tauroursodeoxycholyl Ester
X = O, Y = NR, 3-(7,24'-PolyAmine)Ursodeoxycholyl Tauroursodeoxycholyl Amide TABLE A-continued

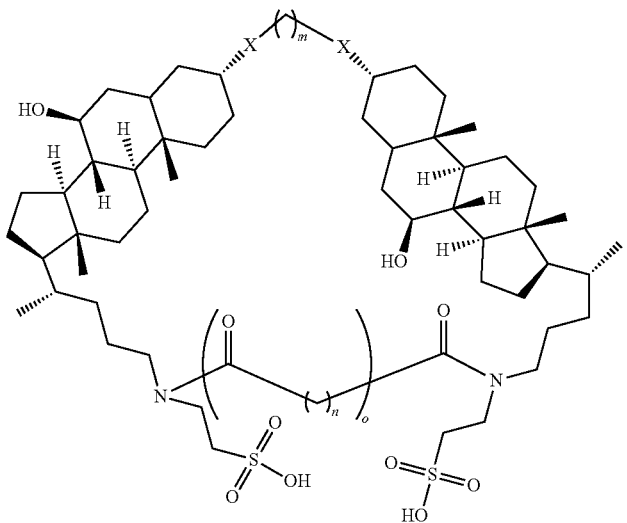

n = 0-7
o = 1-7
m = 1-7

X = NR, 3-(24-PolyLactam)TauroUrsodeoxycholyl Tauroursodeoxycholyl Amine
X = O, 3-(24-PolyLactam)TauroUrsodeoxycholyl Tauroursodeoxycholyl Ether

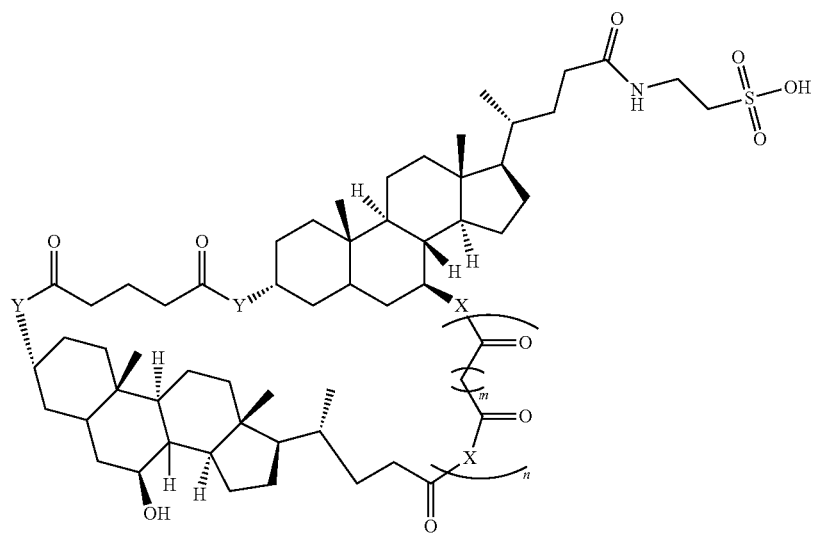

m = 1-7
n = 1-7

X = O, Y = NR, 3-(7,24'-PolyEster)Ursodeoxycholyl Tauroursodeoxycholyl Amide
X = O, Y = NR, 3-(7,24'-PolyAmine)Ursodeoxycholyl Tauroursodeoxycholyl Ester
X = O, Y = NR, 3-(7,24'-PolyEster)Ursodeoxycholyl Tauroursodeoxycholyl Ester
X = O, Y = NR, 3-(7,24'-PolyAmine)Ursodeoxycholyl Tauroursodeoxycholyl Amide TABLE A-continued

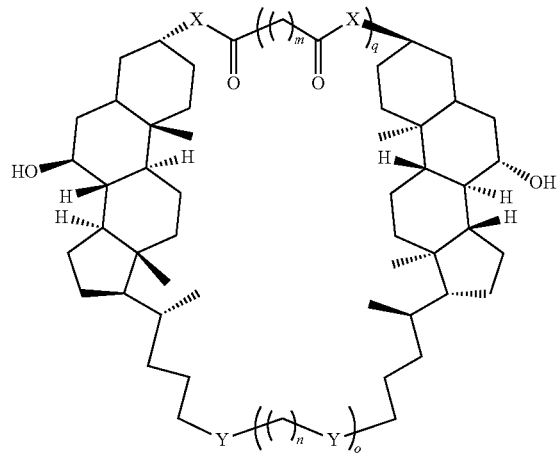

m = 1-7
n = 1-7
o = 1-7
q = 1-7

X = NR, Y = NR, 3-(24-Polyamine) Ursodeoxycholyl Ursodeoxycholyl Amide
X = O, Y = NR, 3-(24-Polyamine) Ursodeoxycholyl ursodeoxycholyl Ester
X = NR, Y = O, 3-(24-Polyether) Ursodeoxycholyl Ursodeoxycholyl Amide
X = O, Y = O, 3-(24-Polyether) Ursodeoxycholyl ursodeoxycholyl Ester

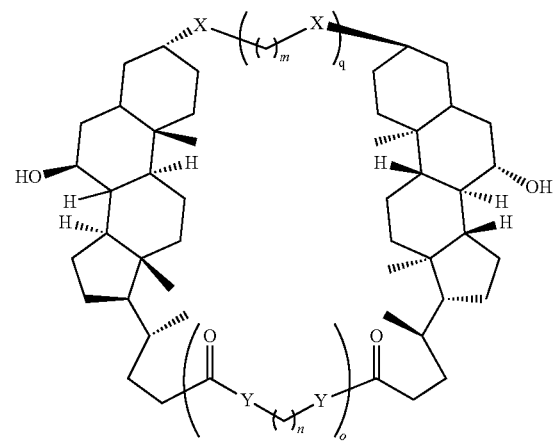

m = 1-7
n = 1-7
o = 1-7
q = 1-7

X = NR, Y = NR, 3-(24-PolyLactam) Ursodeoxycholyl Ursodeoxycholyl Amine
X = O, Y = NR, 3-(24-PolyLactam) Ursodeoxycholyl ursodeoxycholyl Ether
X = NR, Y = O, 3-(24-PolyLactone) Ursodeoxycholyl Ursodeoxycholyl Amine
X = O, Y = O, 3-(24-PolyLactone) Ursodeoxycholyl ursodeoxycholyl Ether TABLE A-continued
7-TPT:
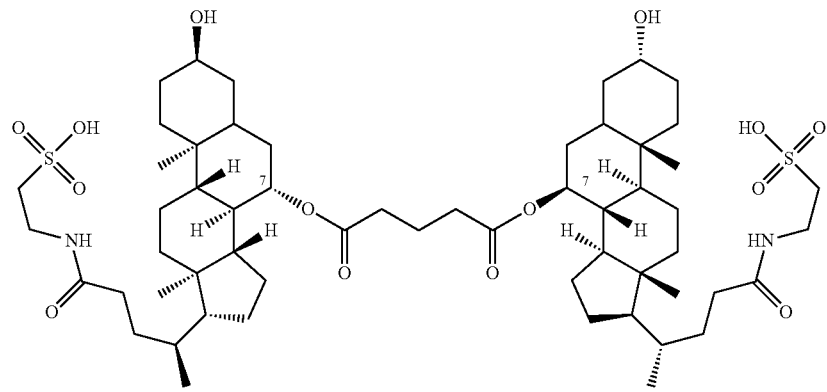
7-TPT
Di-7-Tauroursodeoxycholyl Glutarate
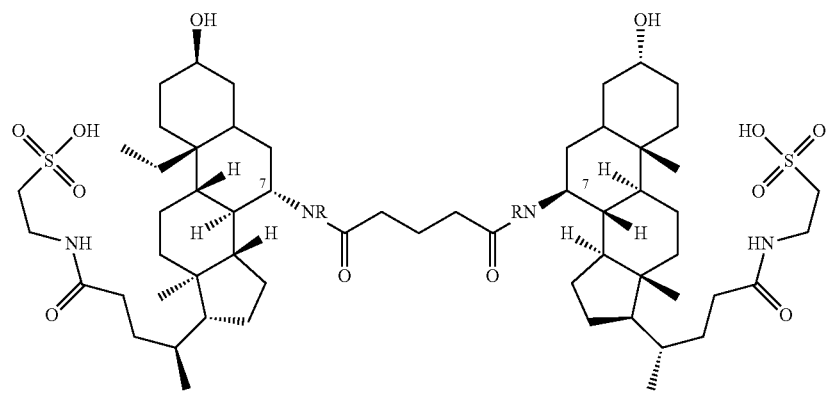
7-TPAT
Di-7-Tauroursodeoxycholyl Glutaramide
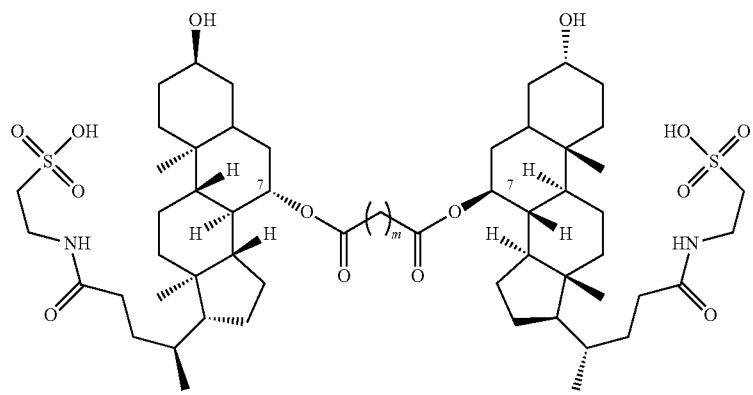
m = 1-7
7-TT Ester
7-Tauroursodeoxycholyl Tauroursodeoxycholyl Ester TABLE A-continued

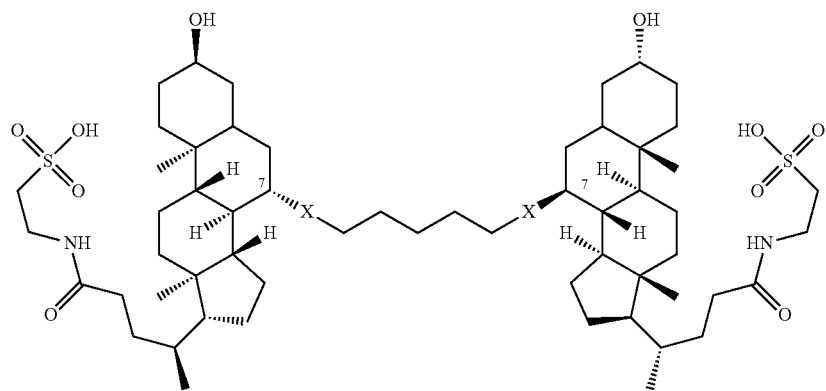

X = O, 7-TT Diether
X = NR, 7-TT Diamine
X = NR, 7-TauroUrsodeoxycholyl Tauroursodeoxycholyl Diamine
X = O, 7-TauroUrsodeoxycholyl Tauroursodeoxycholyl Diether

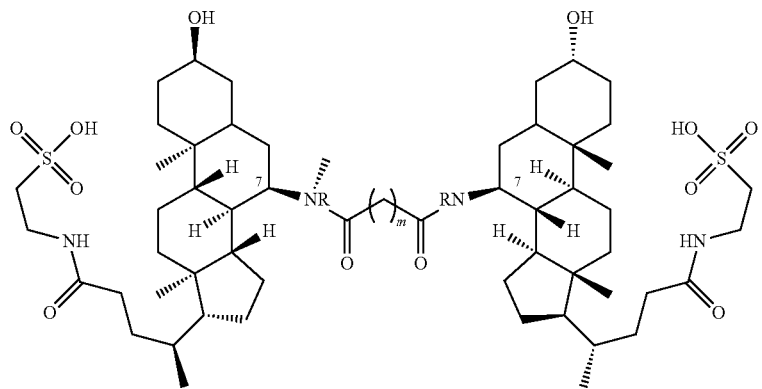

m = 1-7
7-TT Amide
7-Tauroursodeoxycholyl Tauroursodeoxycholyl Amide

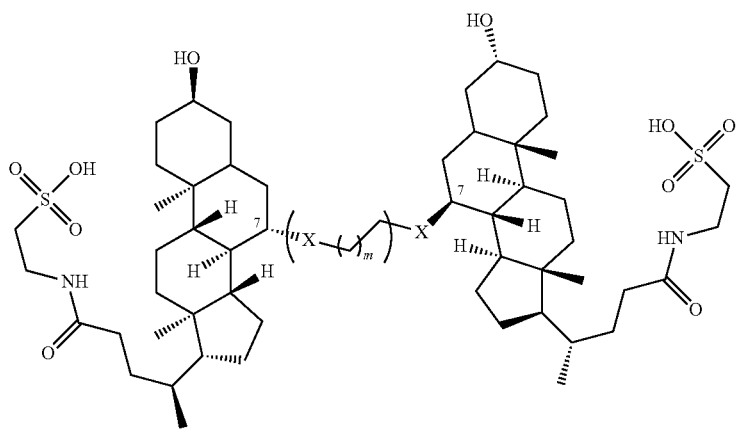

7-TPT
X = NR, 3-TTPA;
X = O, 3-TTPE
X = NR, 7-TauroUrsodeoxycholyl Tauroursodeoxycholyl PolyAmine
X = O, 7-TauroUrsodeoxycholyl Tauroursodeoxycholyl PolyEther TABLE A-continued

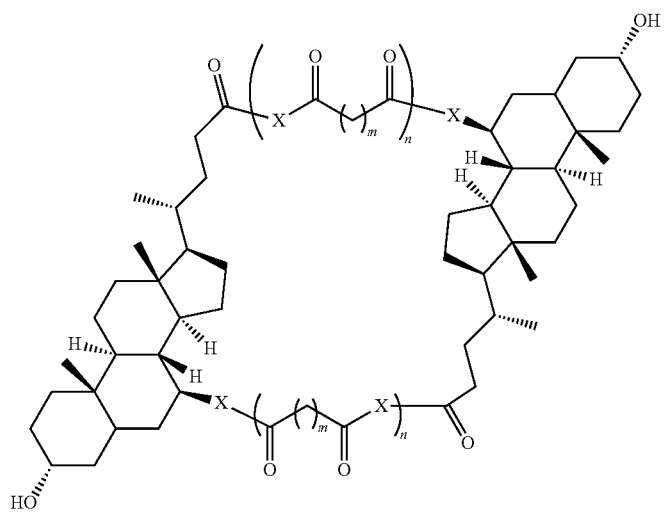

m = 0-7 n = 0-7

X = NR, 7-PL UU Amide

X = O, 7-PL UU Ester

X = O, 7,24'-PolyLactone Ursodeoxycholyl Ursodeoxycholyl Amide

X = NR, 7,24'-PolyLactam Ursodeoxycholyl Ursodeoxycholyl Ester

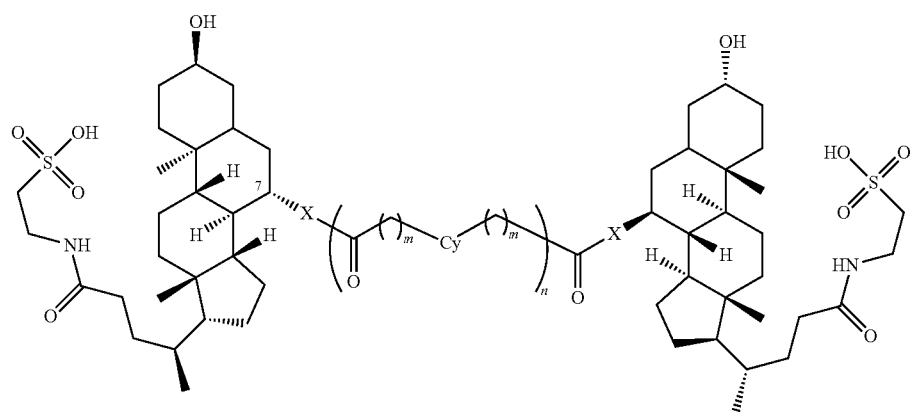

m = 0-7 n = 0-7

X = NR, 7-Polycyclic Tauroursodeoxycholyl Tauroursodeoxycholyl Amide

X = O, 7-Polycyclic Tauroursodeoxycholyl Tauroursodeoxycholyl Ester

Cy = Saturated or Unsaturated ring system including, any sized Heterocycle or Carbocycles with Cic/Trans; para-, ortho- or meta-substitution TABLE A-continued

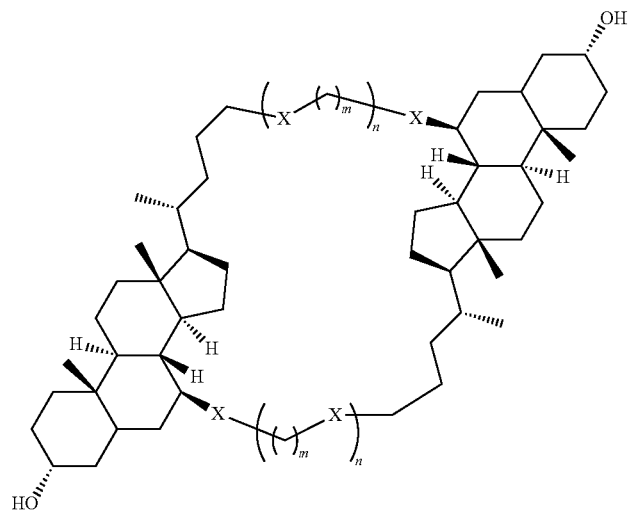

m = 0-7
n = 0-7
X = NR, 7-PE UU
X = O, 7-PA UU
X = O, 7,24'-PolyEther Ursodeoxychotyl Ursodeoxycholyl
X = NR, 7,24'-PolyAmine Ursodeoxycholyl Ursodeoxycholyl

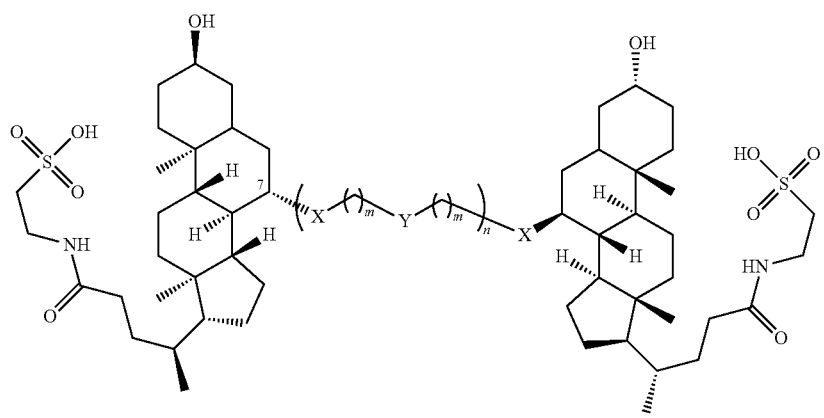

m = 0-7
n = 1-7
X = NR, 7-Polycyclic-Tauroursodeoxycholyl Tauroursodeoxycholyl Amine
X = O, 7-Polycyclic-Tauroursodeoxycholyl Tauroursodeoxycholyl Ether
Cy = Saturated or Unsaturated ring system including, any sized Heterocycle or Carbocycles with Cic/Trans; para-, ortho- or meta-substitution

TABLE B

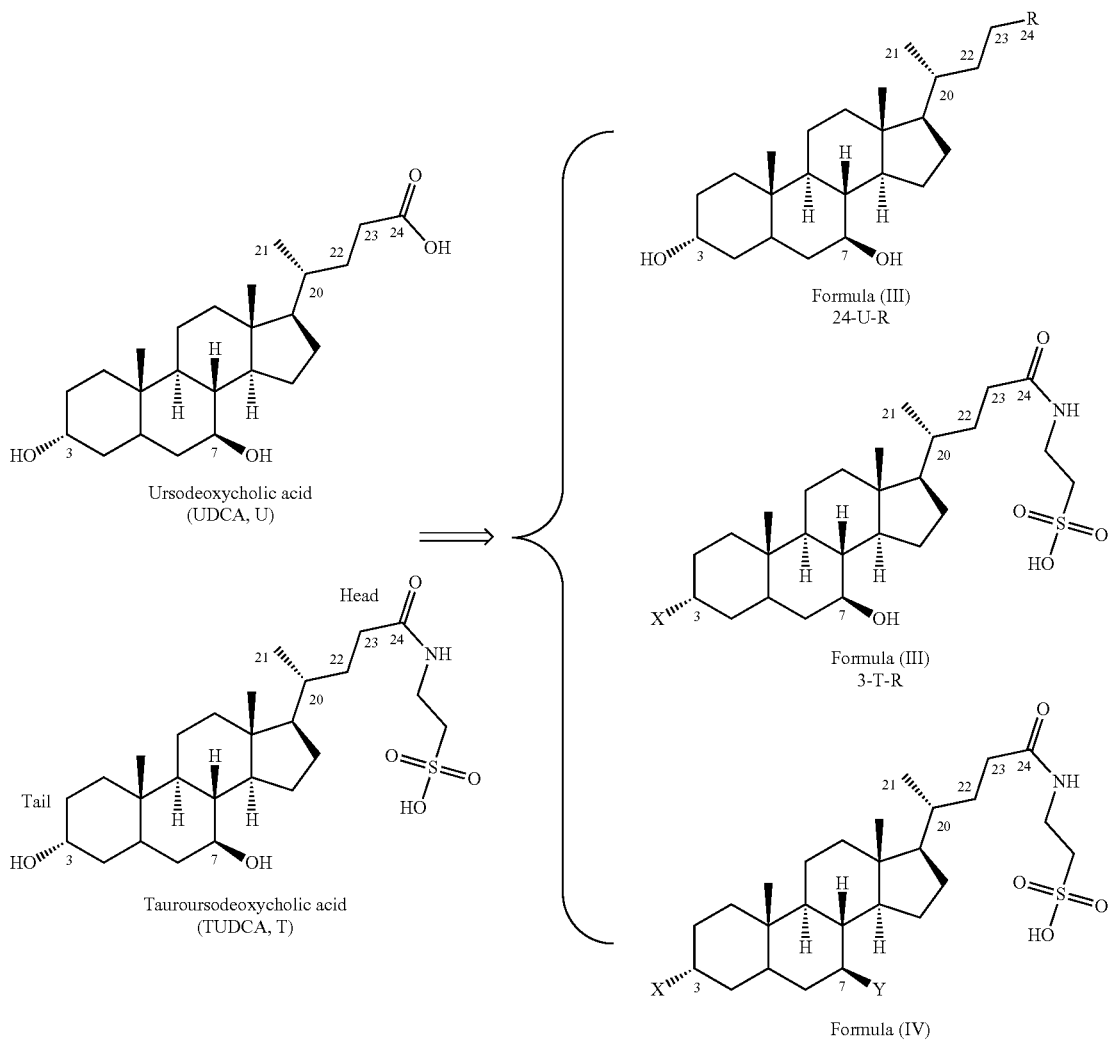

| | |
|---|---|
| —OH, —OAc (Ac = COCH₃, Acetate), | —NH₂, —NHBoc (Boc = tert-Butyloxycarbonyl), |
| —OBz (Bz = COPh, benzoyl), | |
| —OBn (Bn = benzyl), | —NHAc (Ac = COCH₃, Acetate), |
| —OTs (Ts = Tosyl, p-toluenesulfonyl), | —NHBz (Bz = COPh, benzoyl), |
| —OMs (Ms = methanesulfonyl), - | —NHTs (Ts = Tosyl, p-toluenesulfonyl), |
| —OTBS (TBS = tert-Butyldimethylsilyl), | —NHTf (Tf = Trifluoromethanesulfonyl), |
| —OTr(Tr = Triphenylmethyl), | —NHMs (Ms = methanesulfonyl), |
| —OTf (Tf = Trifluoromethanesulfonyl), | —NBn₂ (Bn = Benzyl), |
| —OTHP (THP = Tetrahydropyran), | —N₃. |
| -Carbonyl | -Alkyl |

Formula (II)
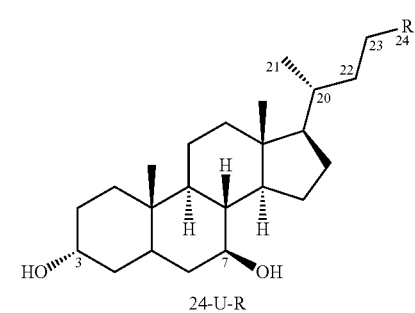
24-U-R
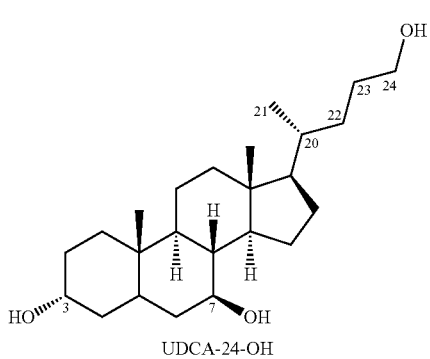
UDCA-24-OH
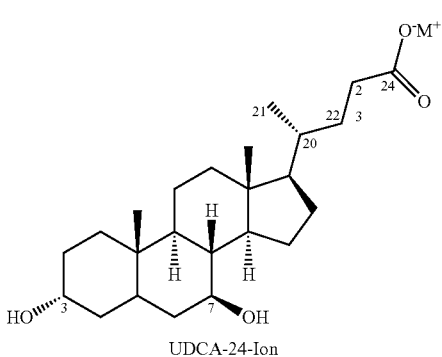
UDCA-24-Ion
$M^+ = Li^+, Na^+, K^+, Bu_4N^+$
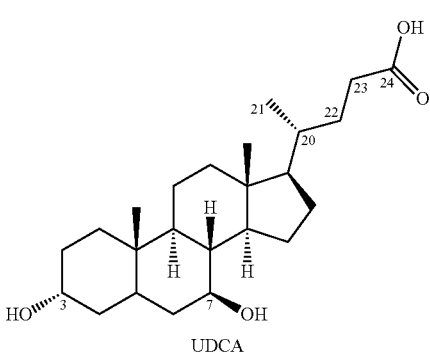
UDCA
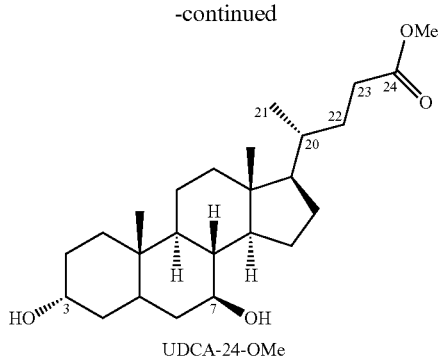
UDCA-24-OMe
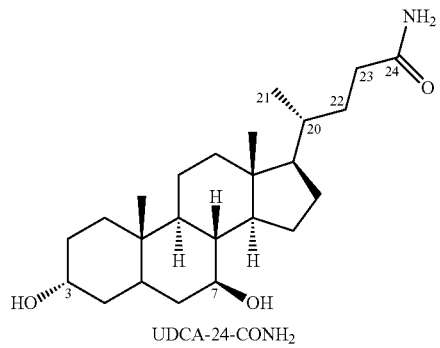
UDCA-24-CONH$_2$
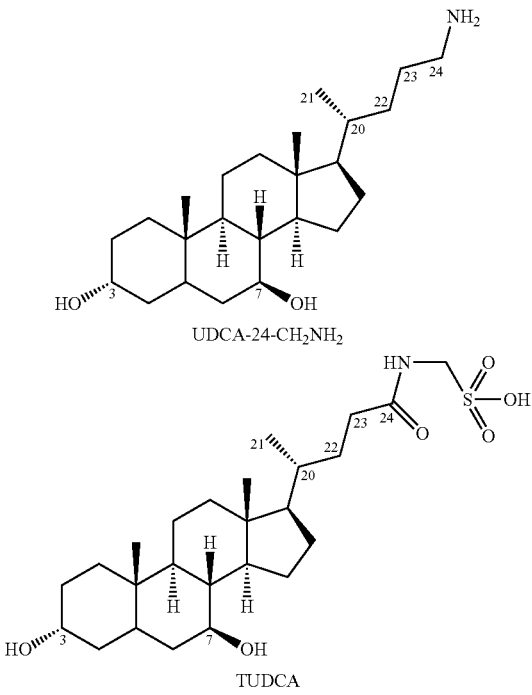
UDCA-24-CH$_2$NH$_2$
TUDCA
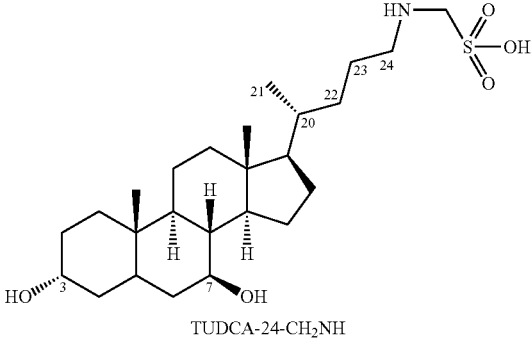
TUDCA-24-CH$_2$NH

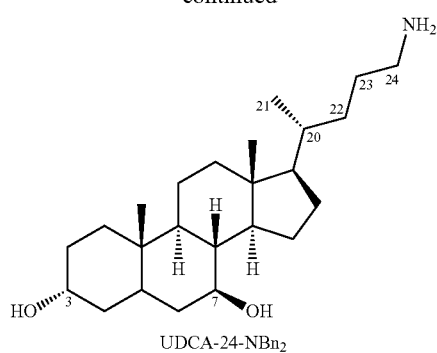
UDCA-24-NBn₂
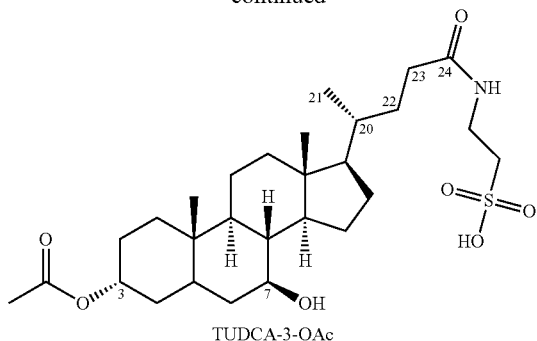
TUDCA-3-OAc
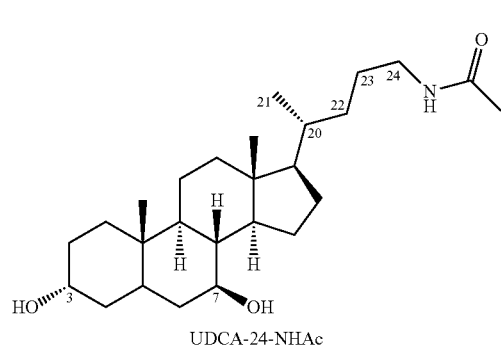
UDCA-24-NHAc
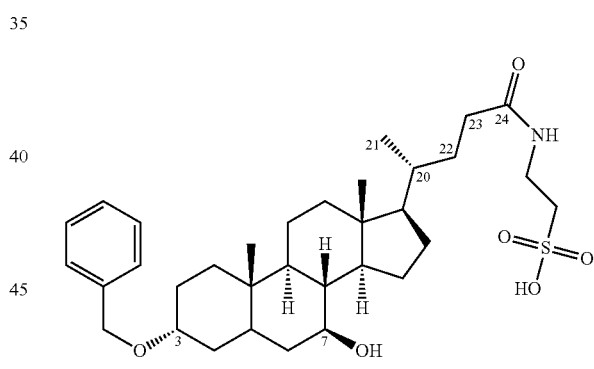
TUDCA-3-OBz
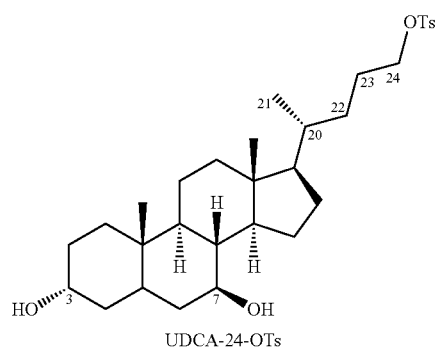
UDCA-24-OTs
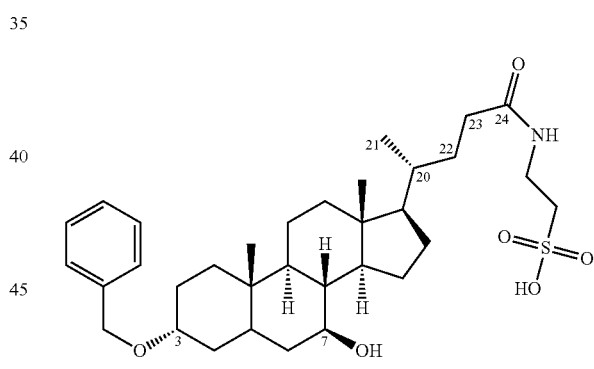
TUDCA-3-OBn
Formula III
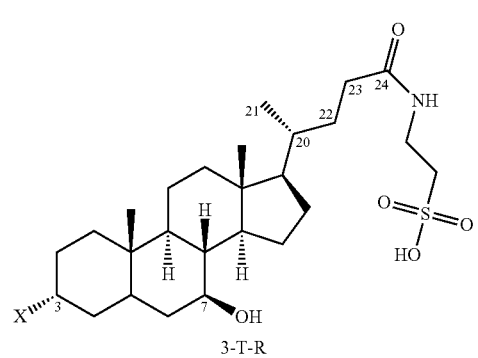
3-T-R
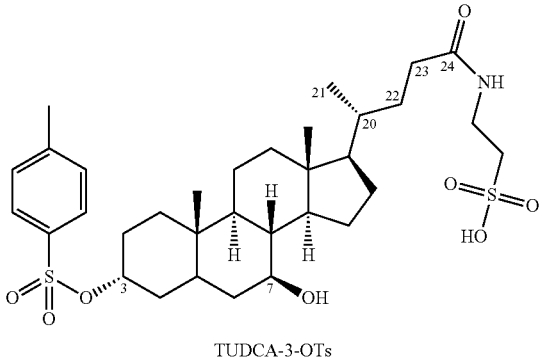
TUDCA-3-OTs

89
-continued
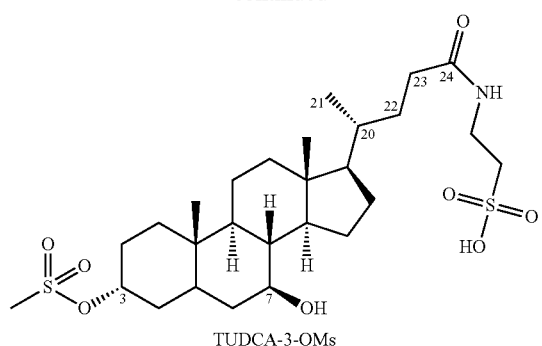
TUDCA-3-OMs
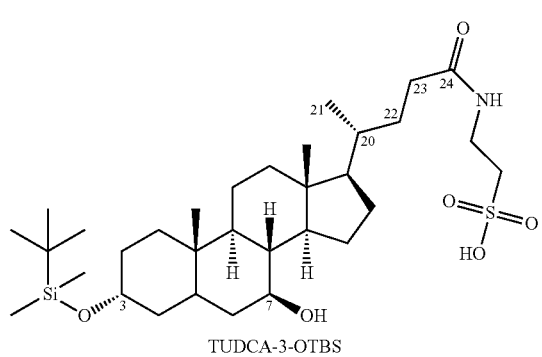
TUDCA-3-OTBS
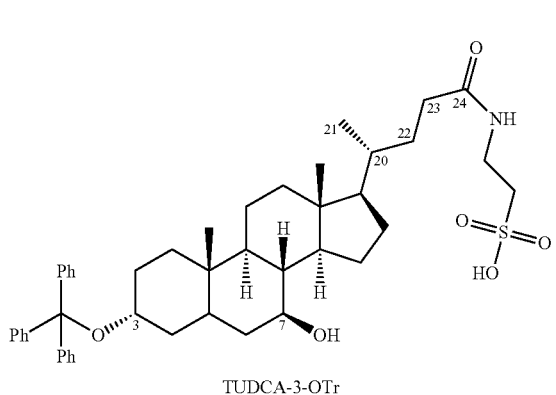
TUDCA-3-OTr
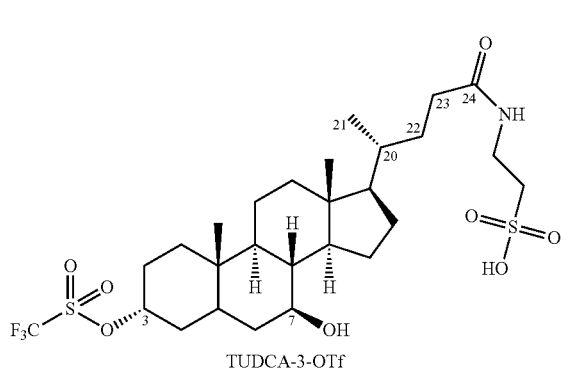
TUDCA-3-OTf
90
-continued
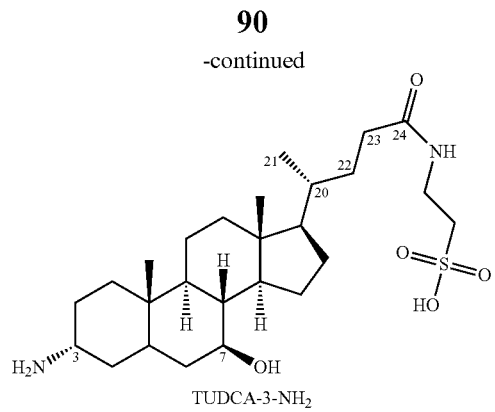
TUDCA-3-NH₂
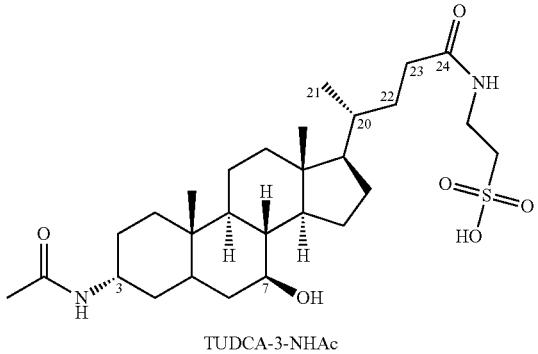
TUDCA-3-NHAc
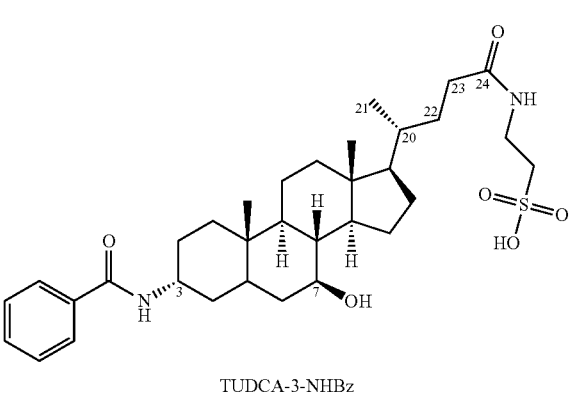
TUDCA-3-NHBz
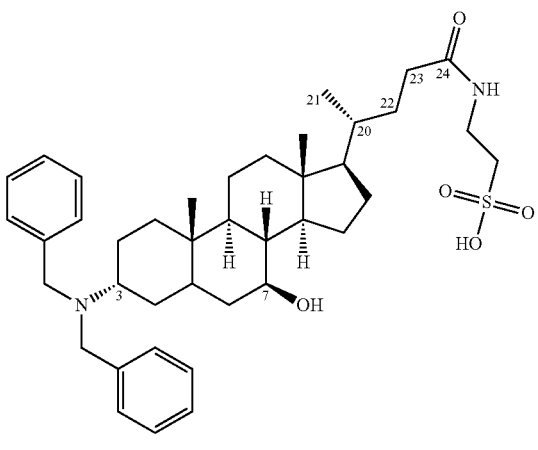
TUDCA-3-NBn₂

-continued
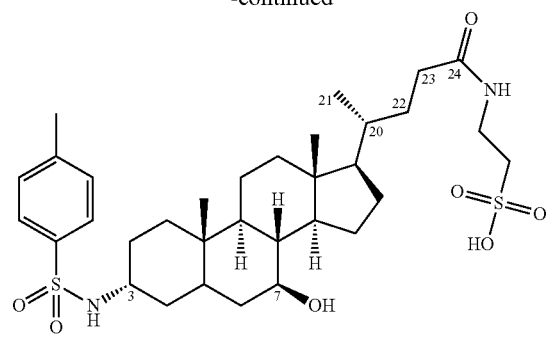
TUDCA-3-NHTs
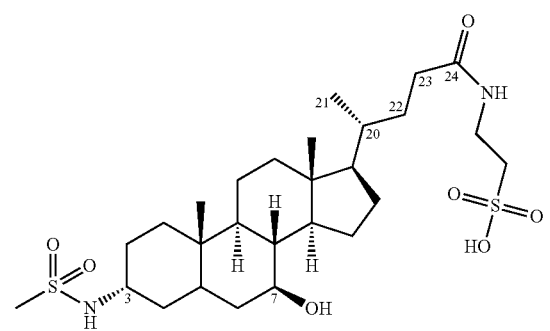
TUDCA-3-NHMs
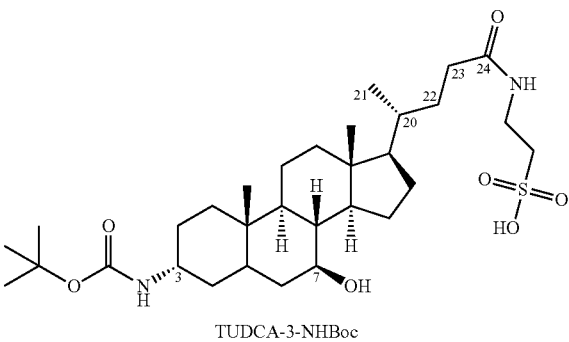
TUDCA-3-NHBoc
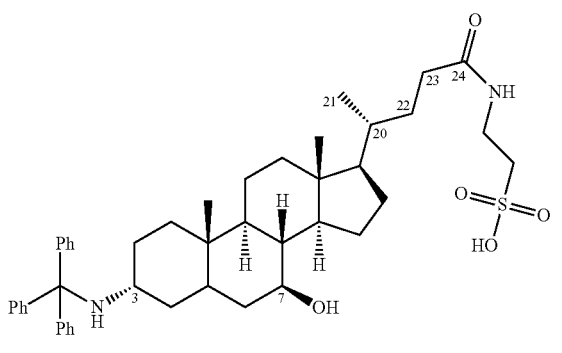
TUDCA-3-NHTr
-continued
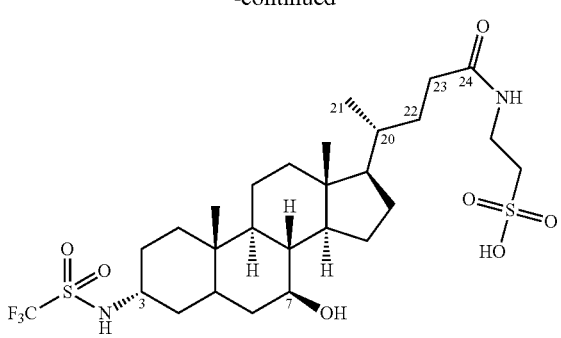
TUDCA-3-NHTf
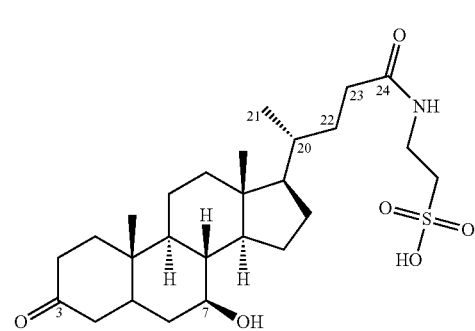
TUDCA-3-ketone
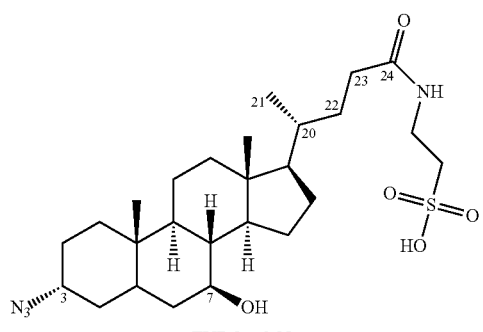
TUDCA-3-N$_3$
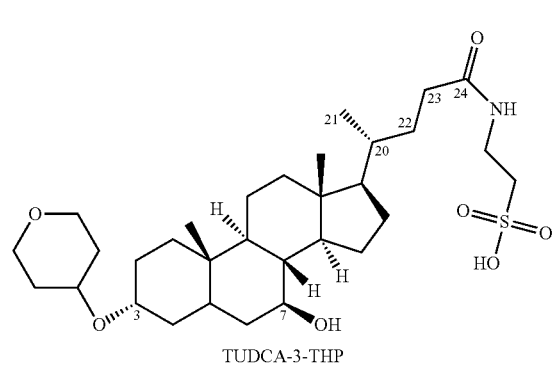
TUDCA-3-THP Formula (IV)
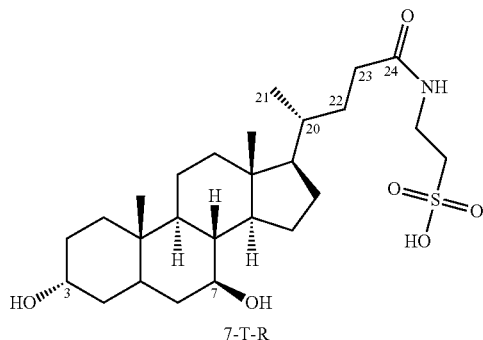
7-T-R
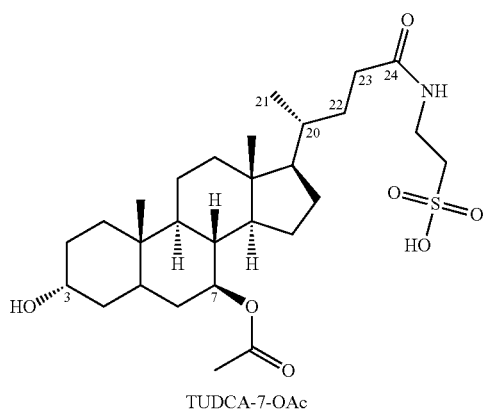
TUDCA-7-OAc
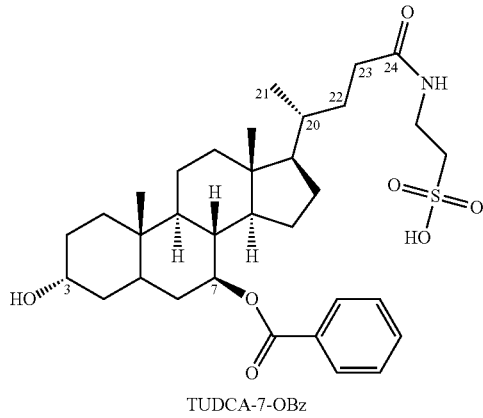
TUDCA-7-OBz
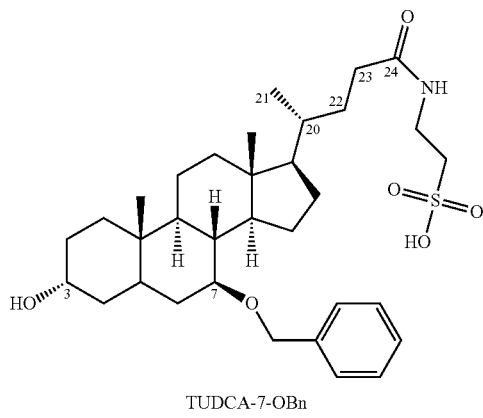
TUDCA-7-OBn
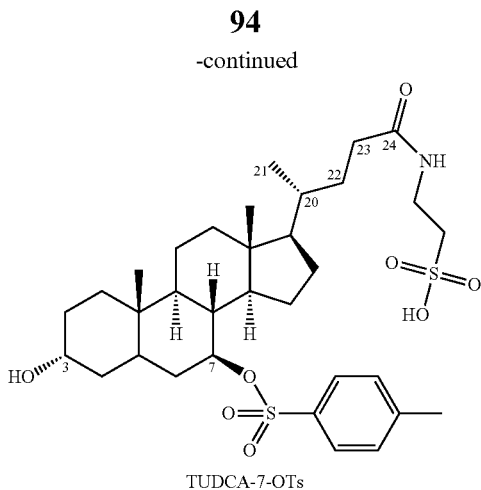
TUDCA-7-OTs
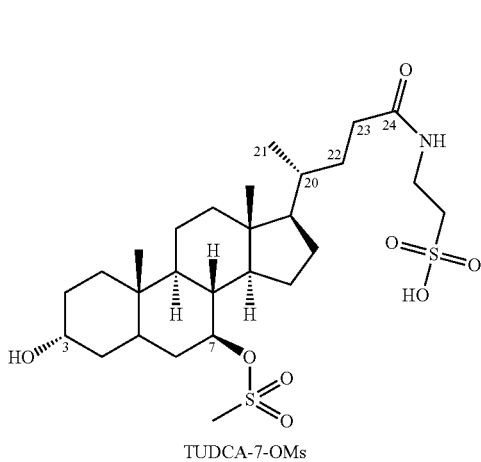
TUDCA-7-OMs
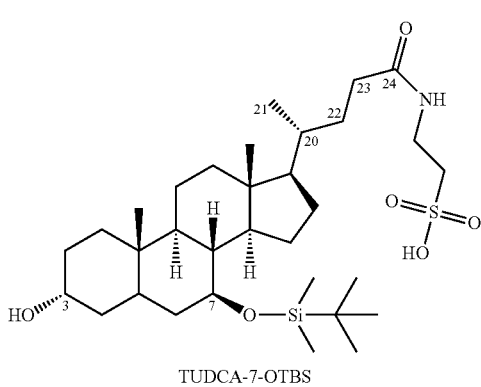
TUDCA-7-OTBS
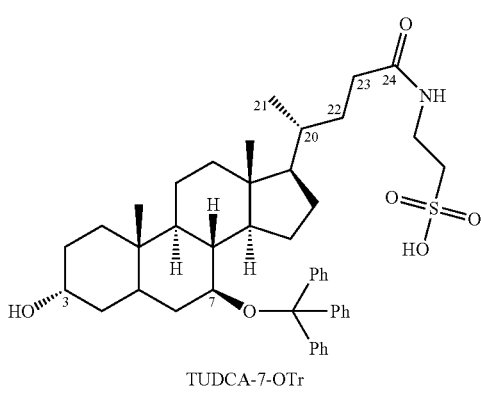
TUDCA-7-OTr -continued
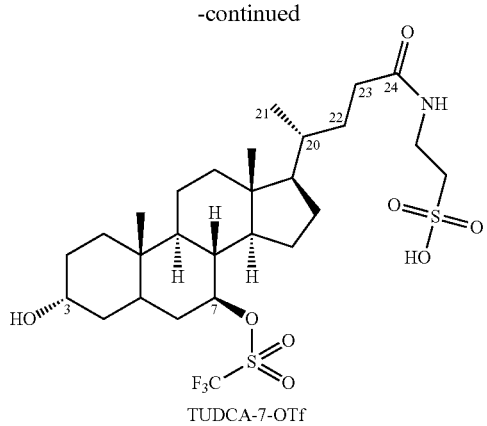
TUDCA-7-OTf
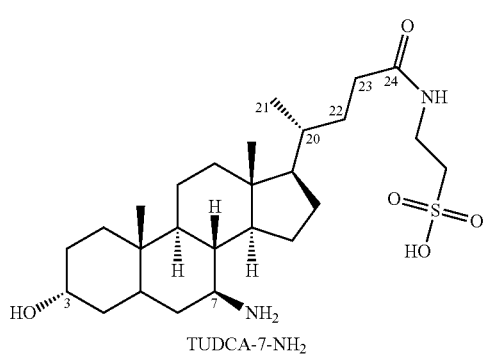
TUDCA-7-NH₂
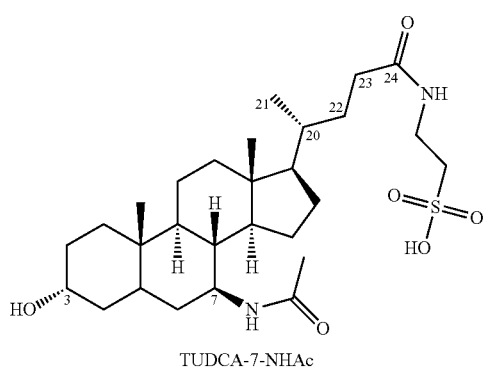
TUDCA-7-NHAc
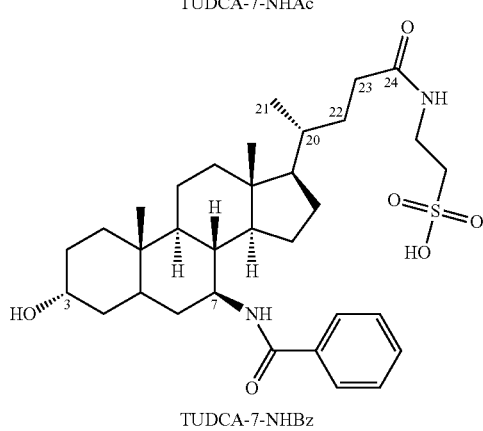
TUDCA-7-NHBz
-continued
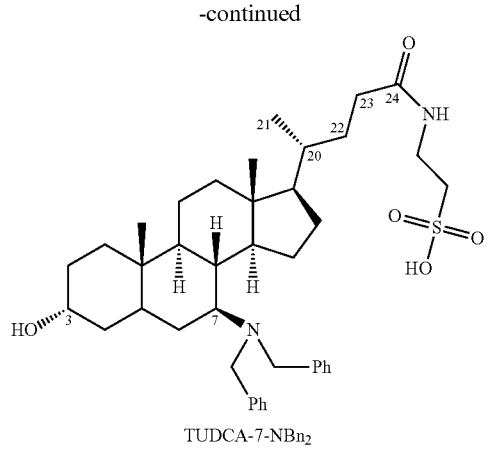
TUDCA-7-NBn₂
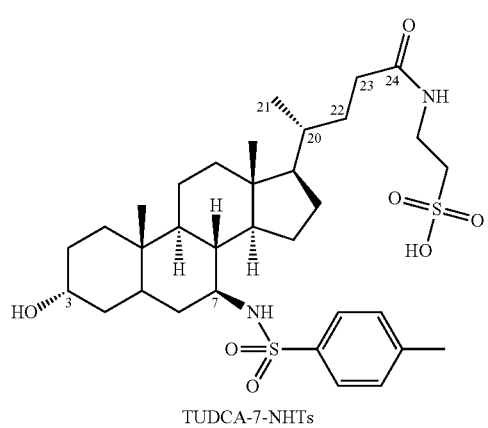
TUDCA-7-NHTs
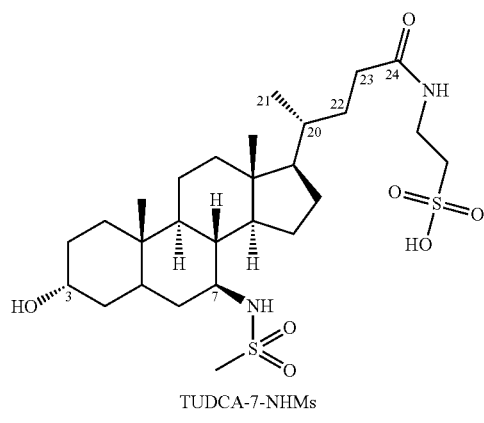
TUDCA-7-NHMs
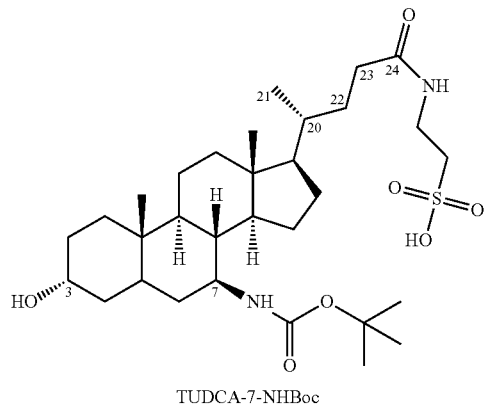
TUDCA-7-NHBoc

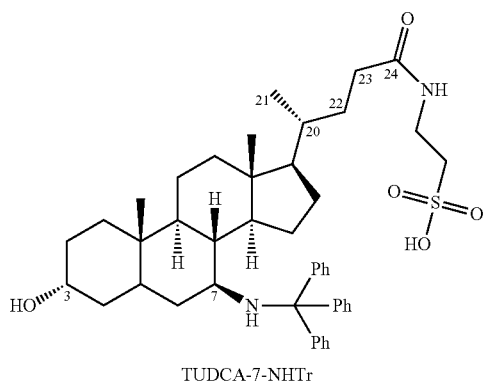

TUDCA-7-NHTr

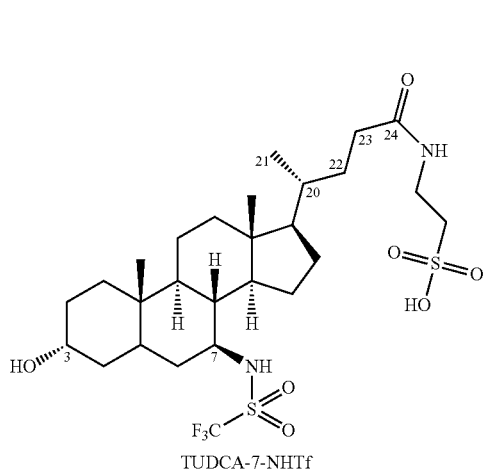

TUDCA-7-NHTf

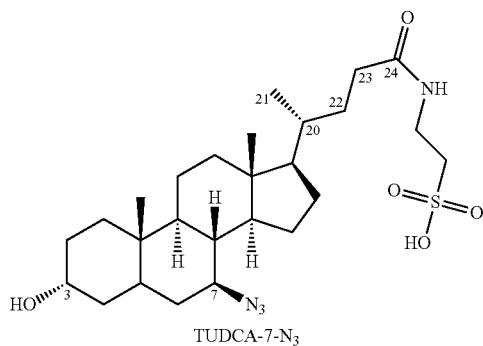

TUDCA-7-N₃

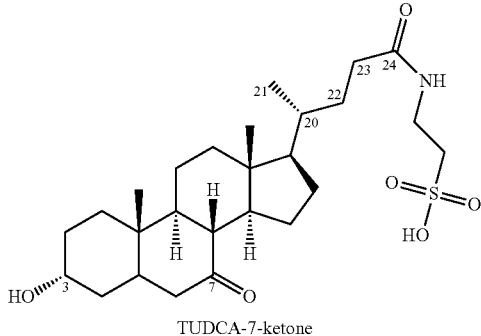

TUDCA-7-ketone

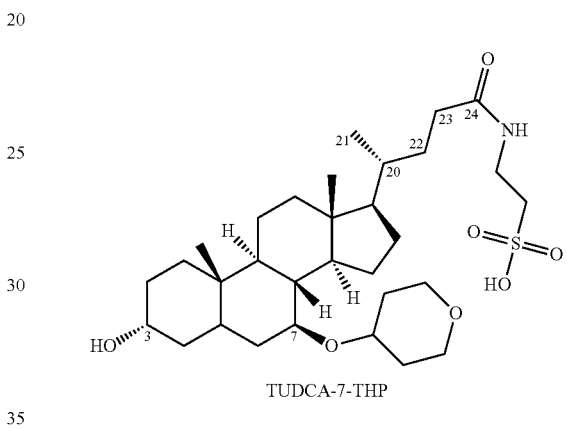

TUDCA-7-THP

PBADs potently and specifically inhibit HBV and HDV infection. The inhibitory effect of some natural bile acids has been described by us (Yan et al., J Virol, March 2014, 88(6):3273-3284) and others: Ni et al., Gastroenterol, April 2014, 146(4):902-905; Konig et al., J Hepatol, online 15 May 2014. Initially, we focused on bile acid derivative modifications (Scheme 1). Primary or secondary bile salts with or without modifications, including cholic acid (CA), taurocholic acid (TCA), glycocholic acid (GCA), lithocholic acid (LCA), deoxycholic acid (DCA), taurolithocholic acid (TLCA), chenodeoxycholic acid (CDCA), ursodeoxycholic acid (UDCA), hyodeoxycholic acid (HDCA), tauroursode-oxycholic acid (TUDCA) and other listed derivatives were incubated with HepG2-NTCP cells and the binding of a FITC labeled pre-S1 peptide to the receptor was subsequently examined by fluorescence microscopy. Consistent with the results that bile acids blocked pre-S1 lipopeptide binding to NTCP, these substrates of NTCP reduced HDV infection as indicated by staining of intracellular HDV delta antigen of infected cells. We further evaluated the ability of these bile salts in inhibiting HBV infection. The levels of secreted HBV e antigen of (HBeAg) was decreased when HepG2-NTCP were inoculated with HBV viruses in the presence of indicated bile salts, with TUDCA being the most potent one among all bile acid derivatives tested. Some modified monomeric bile acids we tested, including 7-Diz-TUDCA, Iso-TUDCA, CA-UDCA, Diz-UDCA, 3-Diz-TUDCA, Biotin-UDCA, 3-OAc-TUDCA did not show significantly improved inhibitory efficiency over the natural monomeric TUDCA (Table C).

TABLE C
Monomeric Bile acids for NTCP inhibitors
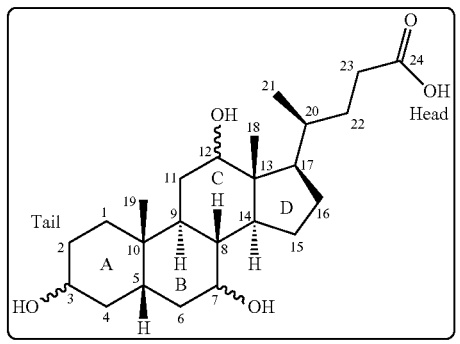
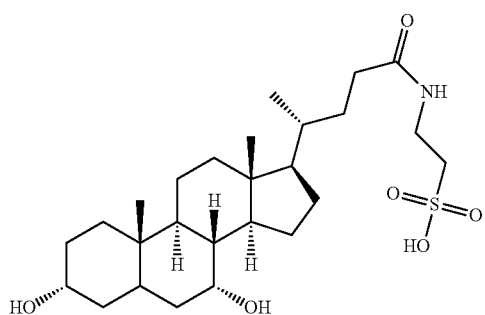
Chenodeoxycholic acid (TCDCA)
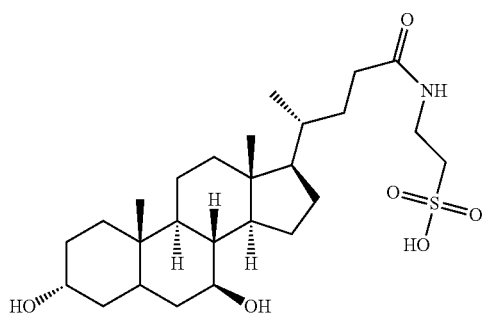
Tauroursodeoxycholic acid (TUDCA)
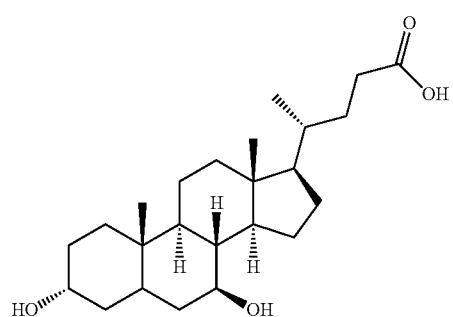
Ursodeoxycholic acid (UDCA)

TABLE C-continued
Monomeric Bile acids for NTCP inhibitors
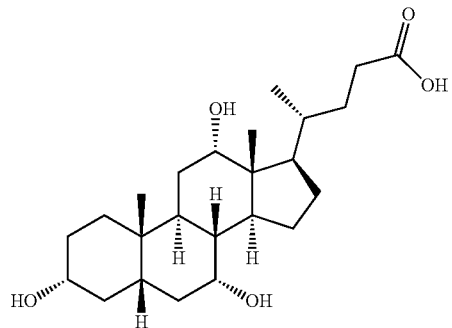
Cholic acid (CA)
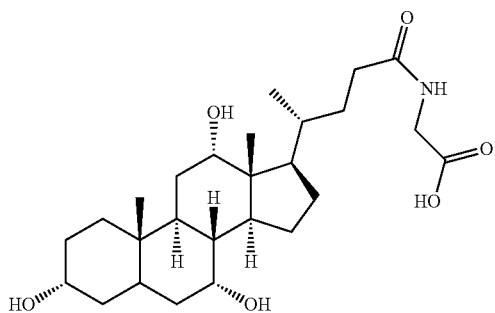
Glycocholic acid (GCA)
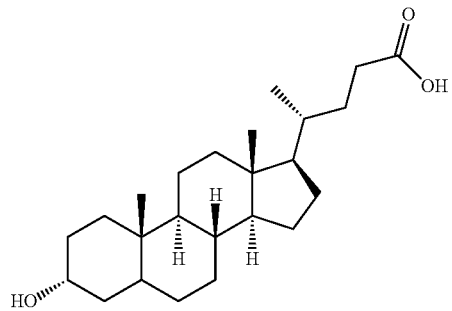
Lithocholic acid (LCA)
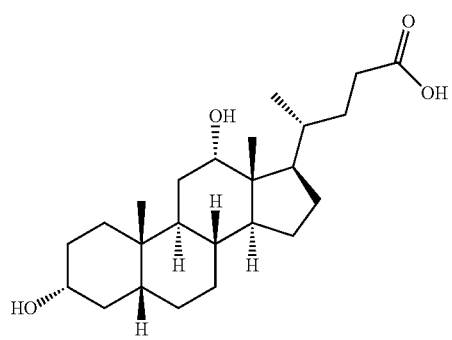
Deoxycholic acid (DCA)

TABLE C-continued
Monomeric Bile acids for NTCP inhibitors
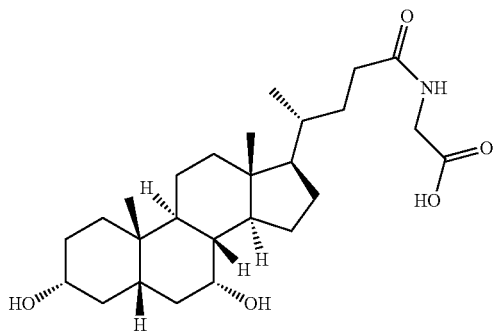 [SMILES: C[C@H](CCC(=O)NCC(=O)O)[C@H]1CC[C@H]2[C@@H]3[C@H](O)C[C@@H]4C[C@H](O)CC[C@]4(C)[C@H]3CC[C@]12C]
Glycochenodeoxycholic acid (GCDCA)
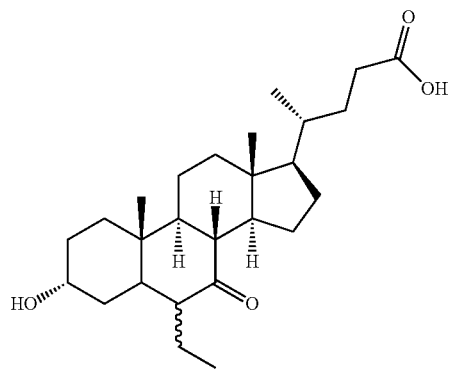
UDCA-6-Ethyl-7-Ketone
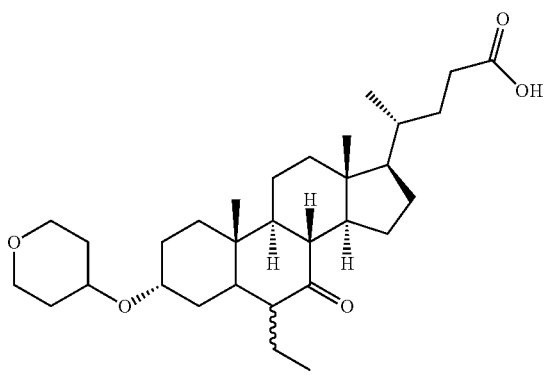
UDCA-3-THP-6-Ethyl-7-Ketone
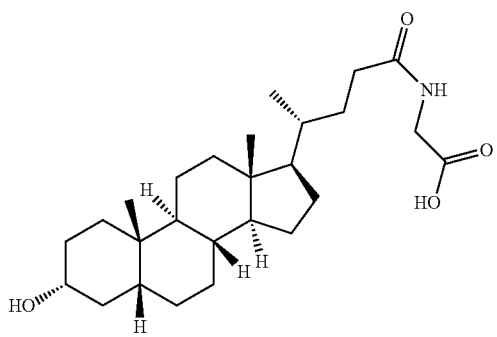 [SMILES: C[C@H](CCC(=O)NCC(=O)O)[C@H]1CC[C@H]2[C@@H]3CC[C@@H]4C[C@H](O)CC[C@]4(C)[C@H]3CC[C@]12C]
Glycolithocholic acid (GLCA)

TABLE C-continued
Monomeric Bile acids for NTCP inhibitors
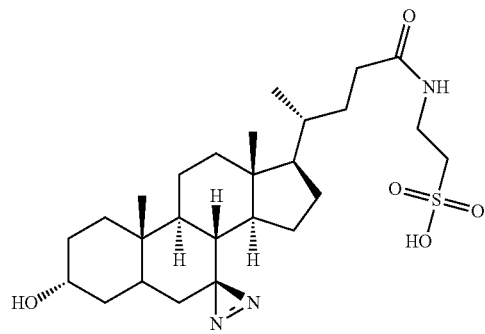
7-Diz-TUDCA
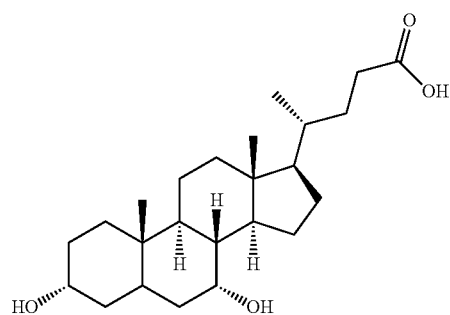
Chenodeoxycholic acid (CDCA)
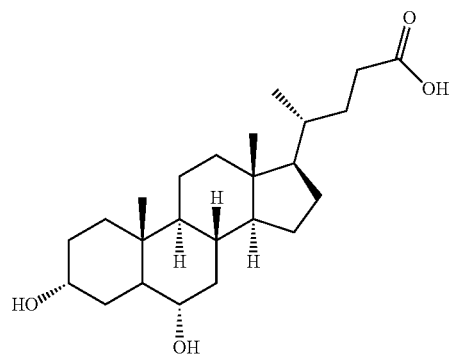
Hyodeoxycholic acid (HDCA)
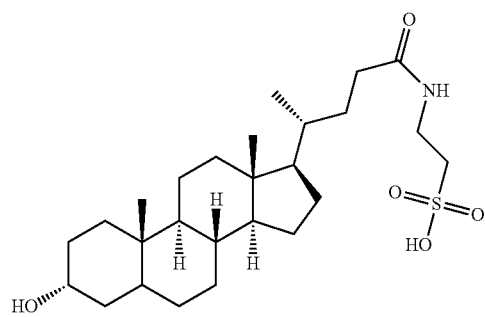
Taurolithocholic acid (TLCA)

TABLE C-continued
Monomeric Bile acids for NTCP inhibitors
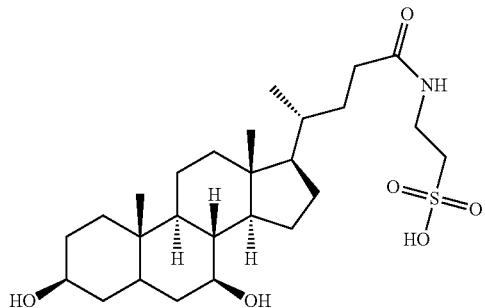
Iso-tauroursodeoxycholic acid (iso-TUDCA)
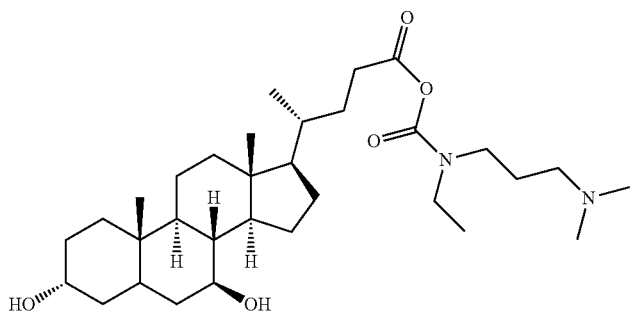
Carbamic-UDCA (CA-UDCA)
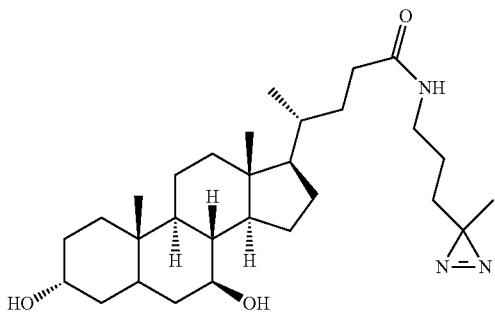
Diz-Ursodeoxycholic acid (DiZ-UDCA)
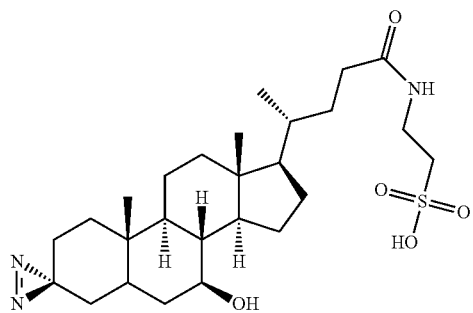
3-Diz-TUDCA

TABLE C-continued
Monomeric Bile acids for NTCP inhibitors
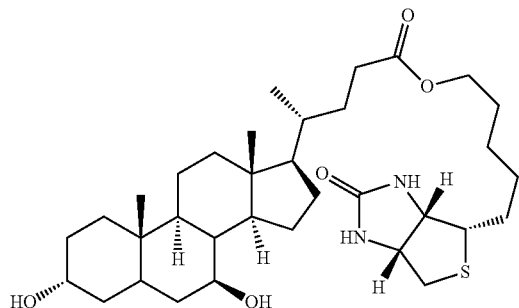
Biotin-UDCA
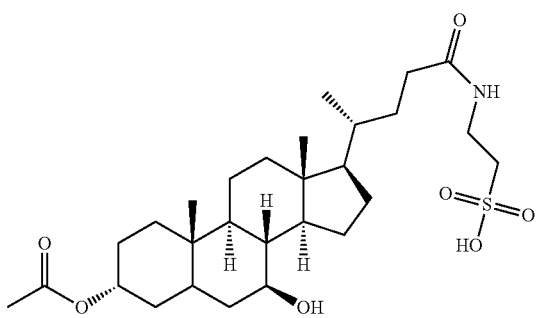
3-OAc-TUDCA
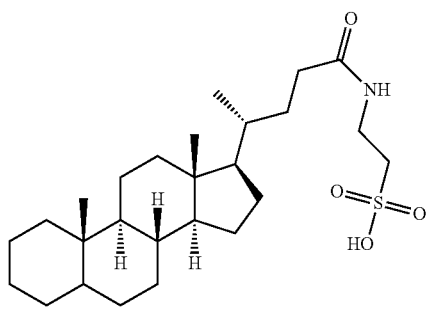
Trideoxylcholic acid (TDCA)
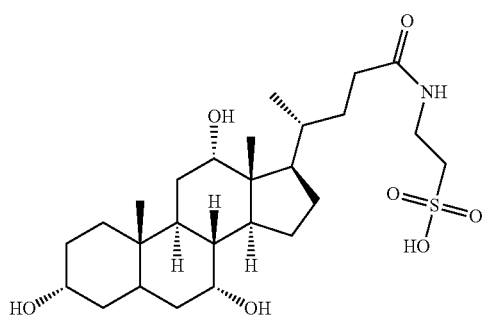
Taurocholic acid (TCA)

Figure 2:
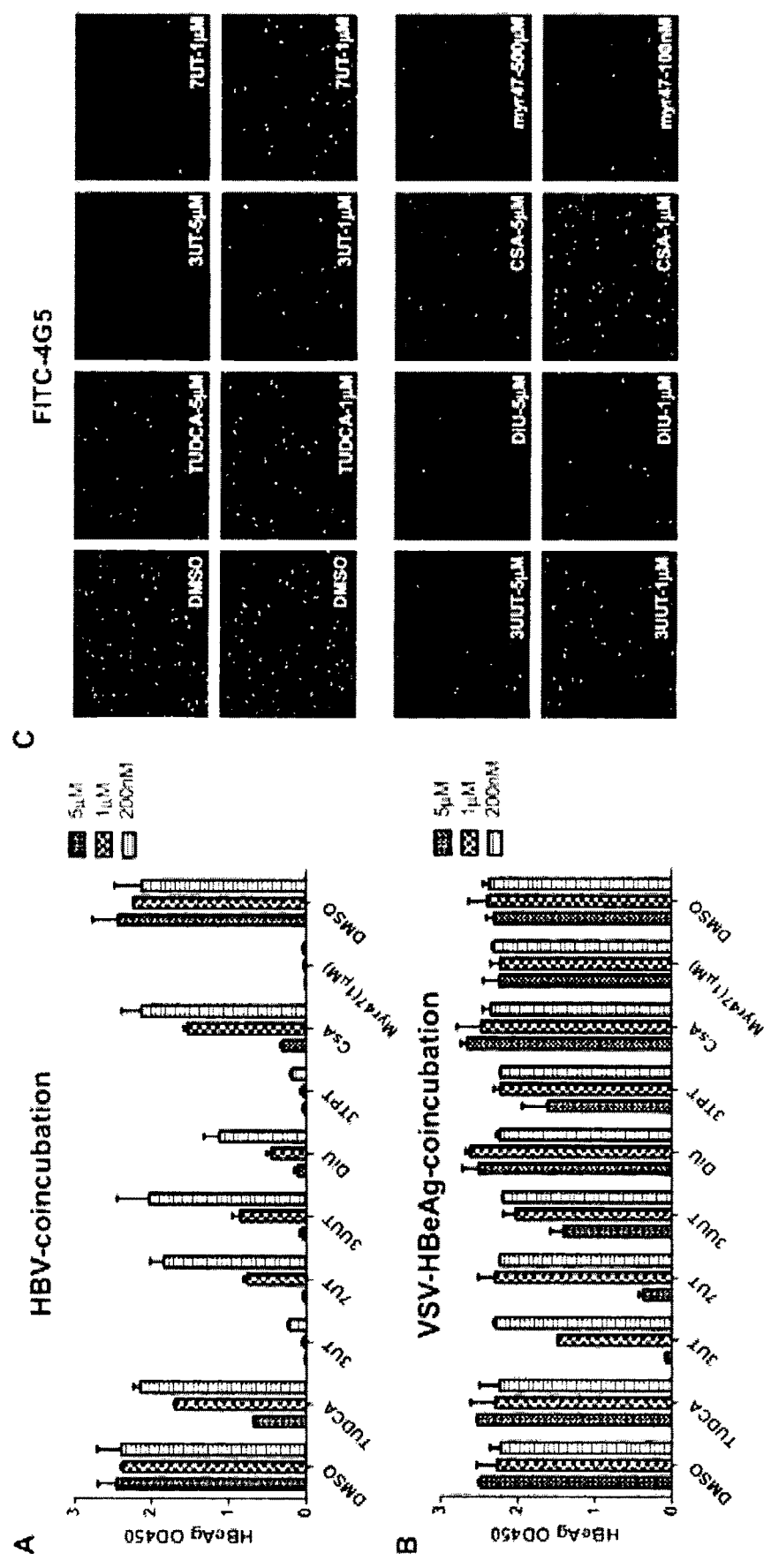
FIG. 2 PBAD inhibited NTCP-mediated HBV and HDV infection. (A-B) HepG2-NTCP infected with HBV (A) and a control virus VSV-HBeAg (B) in the presence of indicated PBADs with different concentrations. On day 5 post infection (dpi), the level of secreted HBeAg was detected by ELISA. (C) HepG2-NTCP infected with HDV in the presence of indicated PBADs with different concentrations. At day 5 post infection, the intracellular delta antigen were stained with FITC conjugated 4G5 and nuclear stained with DAPI.
Figure 3:
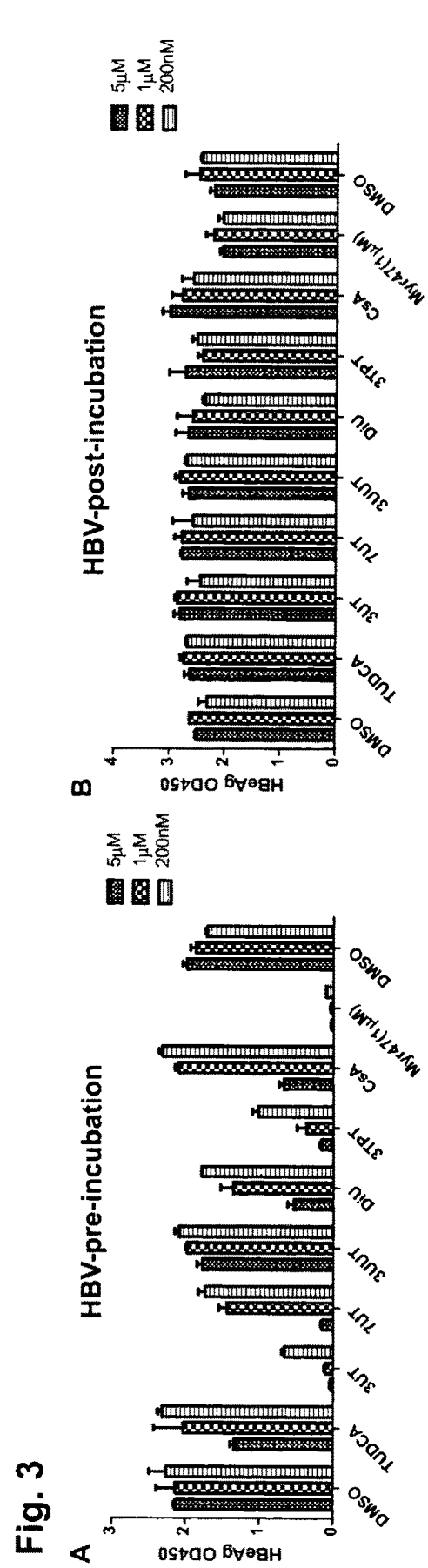
FIG. 3 PBAD inhibited HBV infection at the entry level. HepG2-NTCP cells were incubated with indicated PBADs at different concentrations before (A) or post (B) HBV infection. The treatment lasted for 24 hrs. The level of secreted HBeAg was detected by ELISA at 5 dpi.
Figure 5:
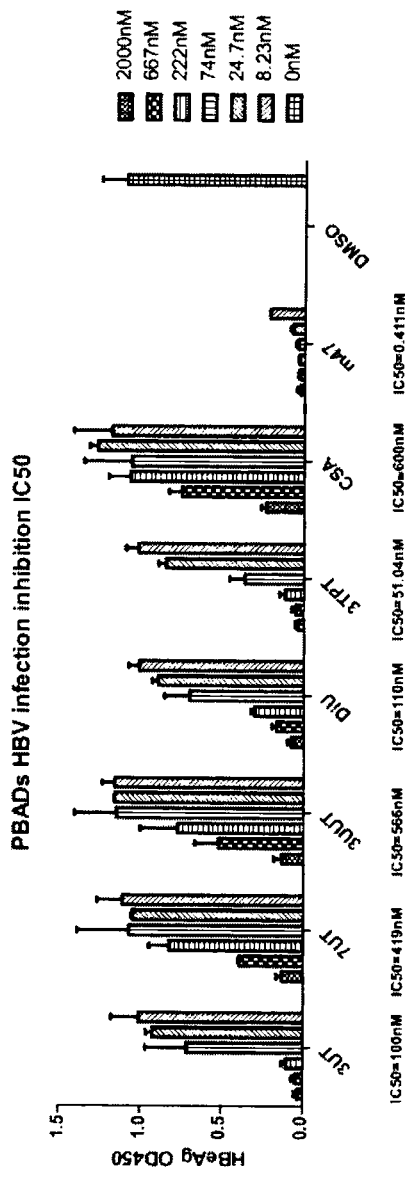
FIG. 5 IC50 of PBAD for inhibiting HBV infection on HepG2-NTCP cells. HepG2-NTCP cells were infected by HBV in the presence of indicated PBADs at different concentrations. The level of HBeAg in the medium was examined at 5 dpi using ELISA.

TABLE C-continued
Monomeric Bile acids for NTCP inhibitors
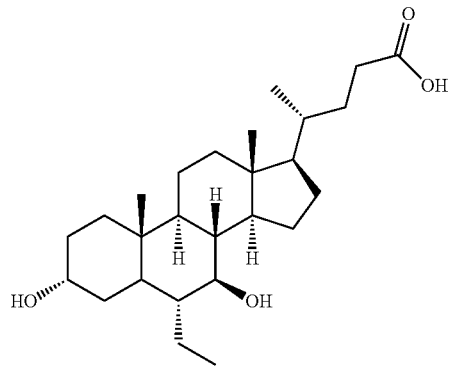
UDCA-6-Ethyl
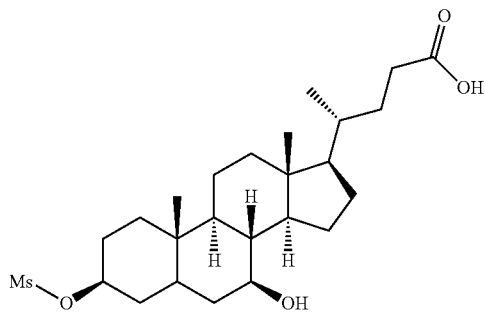
UDCA-3-iso-Ms
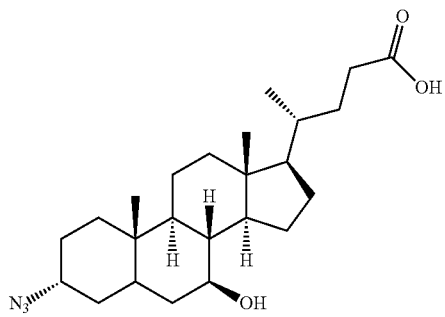
UDCA-3-$N_3$
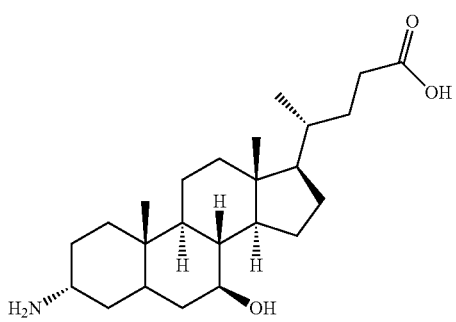
UDCA-3-$NH_2$ TABLE C-continued
Monomeric Bile acids for NTCP inhibitors
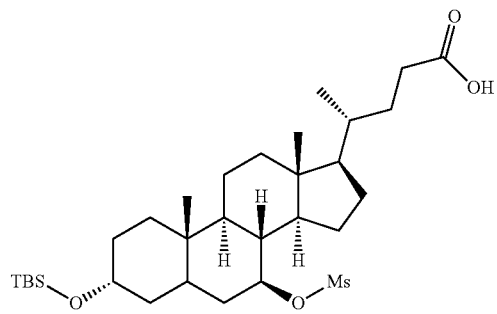
UDCA-3-TBS-7-Ms
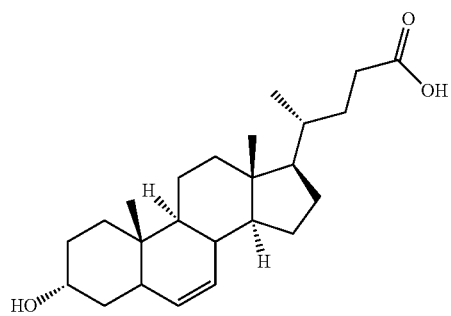 [SMILES: C[C@H](CCC(=O)O)[C@H]1CC[C@H]2C3C=CC4C[C@H](O)CC[C@]4(C)[C@H]3CC[C@]12C]
UDCA-5,6-Olefin
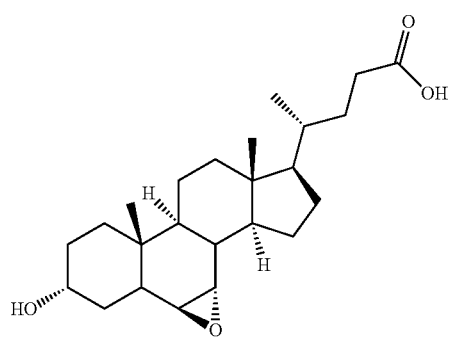 [SMILES: C[C@H](CCC(=O)O)[C@H]1CC[C@H]2C3[C@@H]4O[C@H]4C4C[C@H](O)CC[C@]4(C)[C@H]3CC[C@]12C]
UDCA-6,7-Epoxy
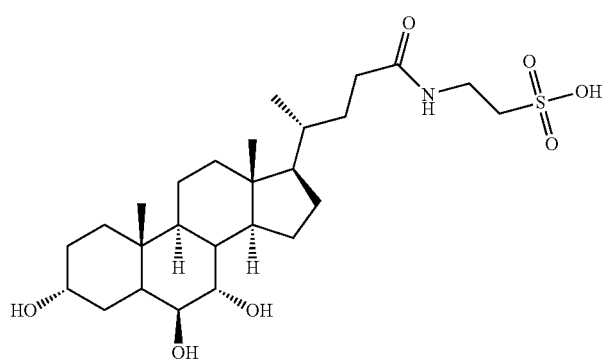
TCDCA-6(S)-OH TABLE C-continued
Monomeric Bile acids for NTCP inhibitors
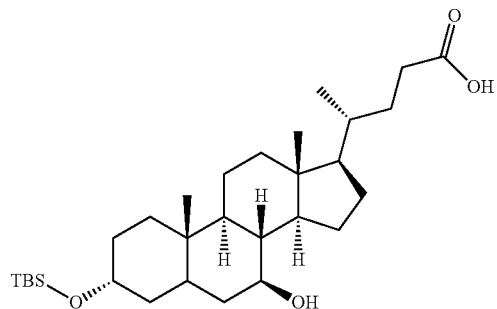
UDCA-3-TBS
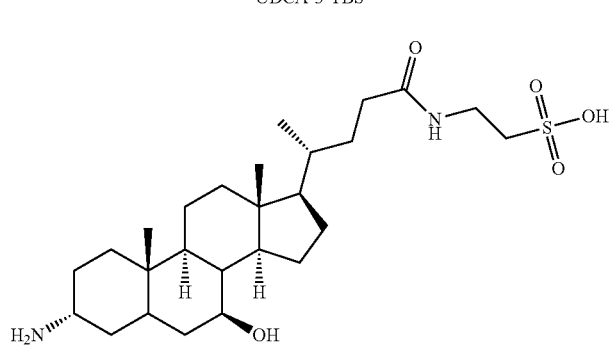
TUDCA-3-NH₂
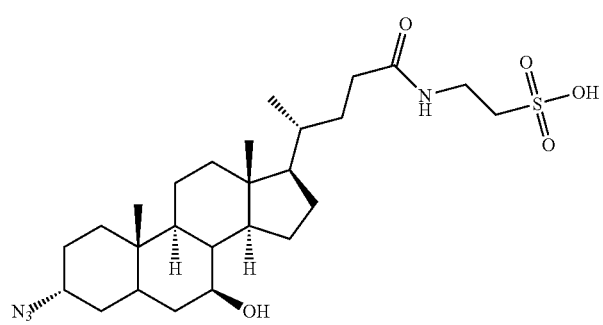
TUDCA-3-N₃
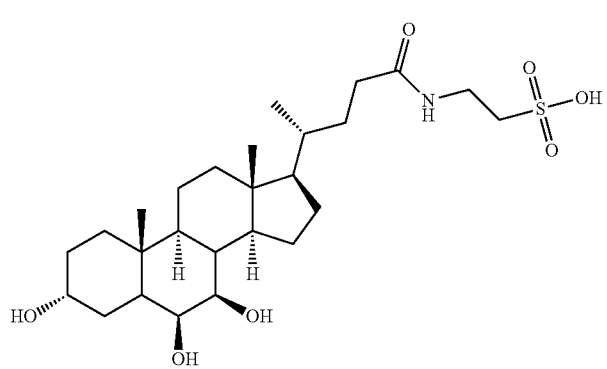
TUDCA-6S-OH TABLE C-continued
Monomeric Bile acids for NTCP inhibitors
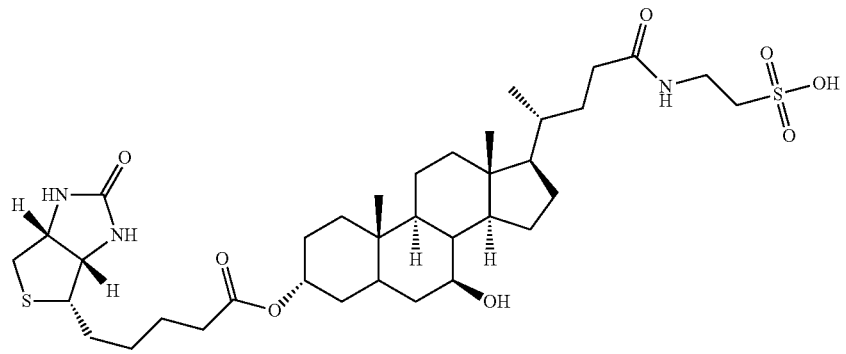
TUDCA-3-Biotin
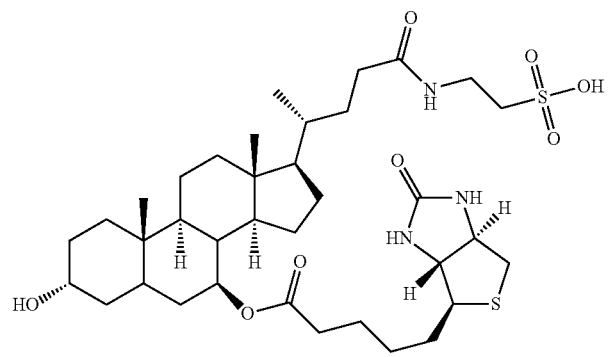
TUDCA-7-Biotin
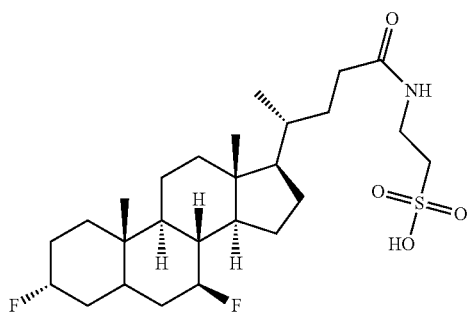
TUDCA-3,7-F
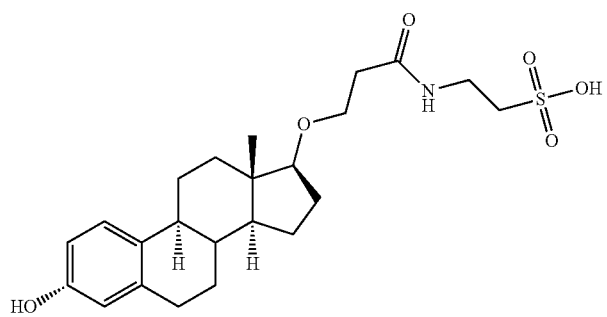
T-estrol Based on quantitative analysis of active impurities we examined several polymeric bile acid derivatives (Table D). We first synthesized the "head-to-tail" polymers, such as dimeric 3-UT (NQL-012) and 7-UT(NQL-015). For "head-to-head" motif, we tried DIU(NQL-009), which was connected by ester bond directly, other type of connections are under studied. For "tail-to-tail" connection, 3-TPT (NQL-018) and 3-TPAT (NQL-044) was linked together through double ester or amide bonds with 5 carbons in the middle, more or less bond connection will be studied as soon as possible. We found 3-UT(NQL-012), 7-UT(NQL-015), DIU (NQL-009), 3-TPT(NQL-018) and 3-TPAT (NQL-044) have high antiviral activity against both HBV and HDV, with an IC50 of the 3-TPT for HBV down to 51 nM (FIG. 5, please also see FIGS. 2 and 3).

TABLE D
Molecular design of tested PBADs
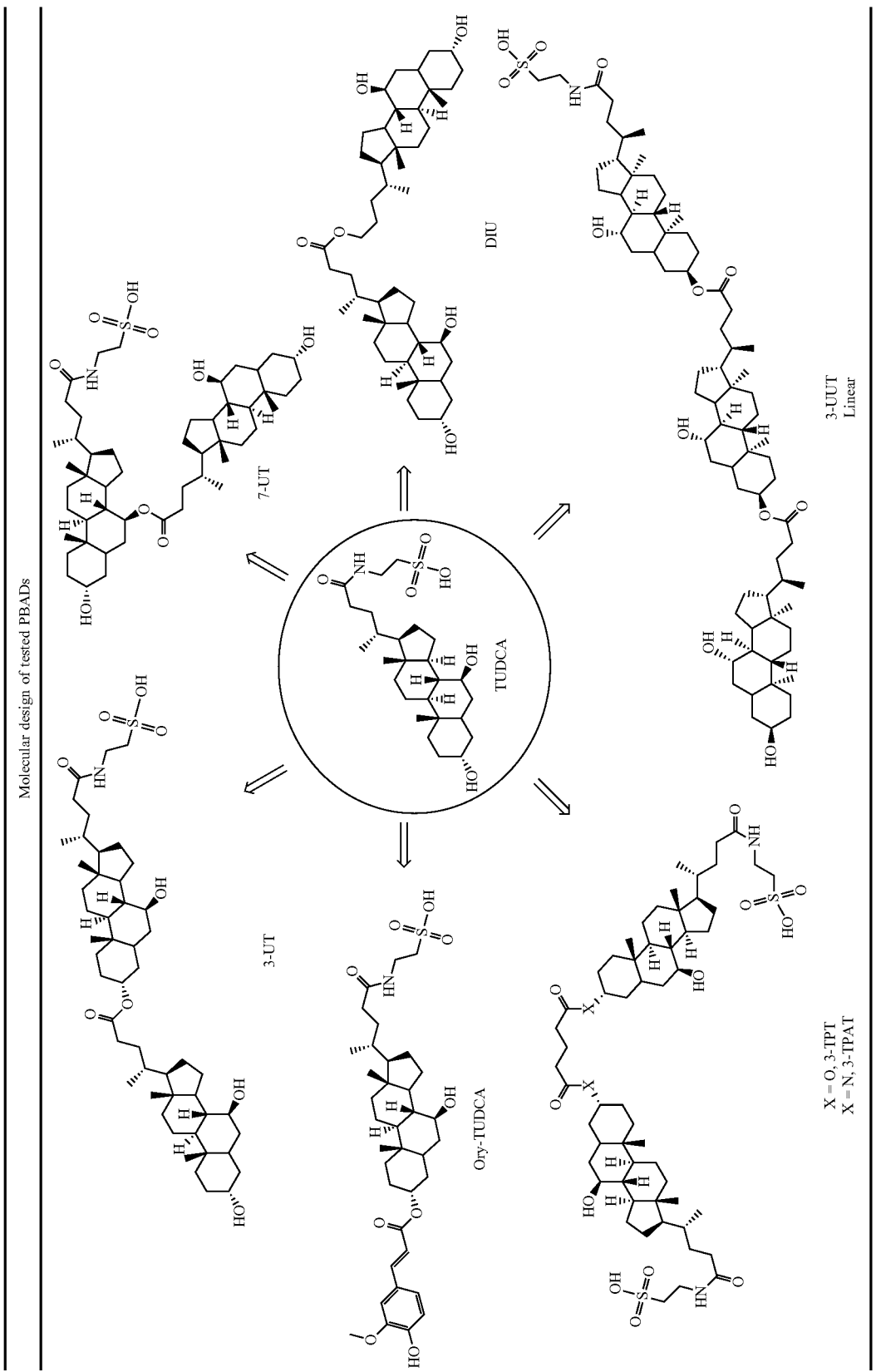

These data indicate that dimeric bile acids based on UDCA and TUDCA motif are active against HBV and HDV infection.

The invention encompasses all combinations of two same or different monomeric bile acid derivatives (formula I-IV) disclosed herein, including alternative linkers, their pharmaceutically tolerated salts, conjugated acid form, metabolic derivatives, and the synthesis, purification and the use of these derivatives and salts, including the structures shown as 3-UT (NQL-012), 7-UT (NQL-015), DIU (NQL-009), 3-TPT and 3-TPAT (NQL-044), which has two UDCAs or TUDCAs connected with ester bond between acid group on one UDCA or TUDCA and one of hydroxyl groups on another UDCA or TUDCA (Scheme 2), and including dimeric bile acids derivatives of the formula (II), (III), (IV) and (V) in Scheme 3.

In the Table E the U and T in the dimeric bile acid derivatives can be symmetric (identical to each other) or asymmetric (combination of UDCA and TUDCA). The L is the conjugated linkage group between different position of U and T. For the "head-to-head" formula (V) U1-L-U2, L connected two side chains of U1 and U2 at positions (via the carbon atom or the substituent thereon) of 20 to 24 via covalent bond. For the "head-to-tail" formula (VI) 3-U1-L-U2, L connected to the position (via the carbon atom or the substituent thereon) of 20 to 24 on one side chain of U1 and 3-positions (via the carbon atom or the substituent X atom) of U2 via covalent bond. For the "head-to-tail" formula (VII) 7-U1-L-U2, L connected to the position (via the carbon atom or the substituent thereon) of 20 to 24 on one side chain of U1 and 7-positions (via the carbon atom or the substituent X atom) of U2 via covalent bond. For the "tail-to-tail" formula (VIII) T1-L-T2, L connected to 3- or 7-position (via the carbon atom or the substituent X or Y atoms) of T1 and 3- or 7-position (via the carbon atom or the substituent X or Y atoms) of T2 via covalent bond. The number n and m can be any Arabic numerals.

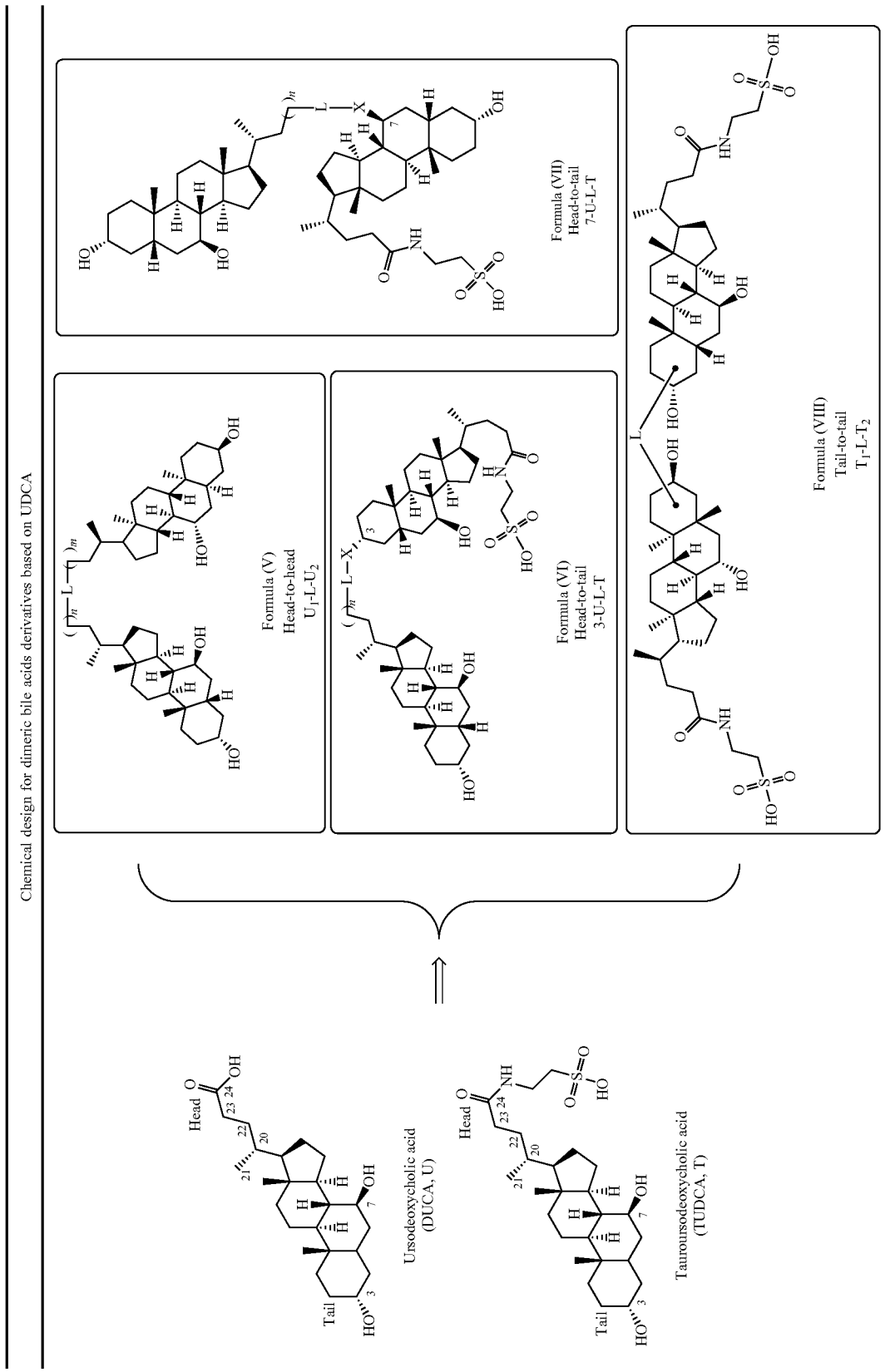
TABLE E
Chemical design for dimeric bile acids derivatives based on UDCA The invention encompasses dimeric bile acids based on monomeric bile acid motif of B (Table F), and in addition to the UDCA and TUDCA dimeric derivatives showed in the Table E, the invention encompasses generally dimeric bile acids derivatives of formula (IX), (X) and (XI) in Table F.

In the table F: B1 and B2 in the dimeric bile acid derivatives can be symmetric (identical to each other) or asymmetric (combination of all the above mentioned monomeric bile acid derivative possibilities). L is the conjugated linkage group between different position of B1 and B2. For the "head-to-head" formula (IX) B1-L-B2, L connected two side chains of B1 and B2 at positions (the carbon atom or the substituent thereon) of 20 to 24 via covalent bond. For the "head-to-tail" formula (X) B1-L-B2, L connected to the position (via the carbon atom or the substituent atoms thereon) of 20 to 24 on one side chain of B1 and any positions (via the carbon atom or the substituent atoms thereon, on the rings of A, B, C and D) of 1 to 19 of B2 via covalent bond. For the "tail-to-tail" formula (XI) B1-L-B2, L connected to any one position (via the carbon atom or the substituent atoms thereon, on the rings of A, B, C and D) of 1 to 19 of B1 and any positions (via the carbon atom or the substituent atoms thereon, on the rings of A, B, C and D) of 1 to 19 of B2 via covalent bond. The number n and m can be any Arabic numerals.

TABLE F

Chemical design for dimeric bile acids derivatives

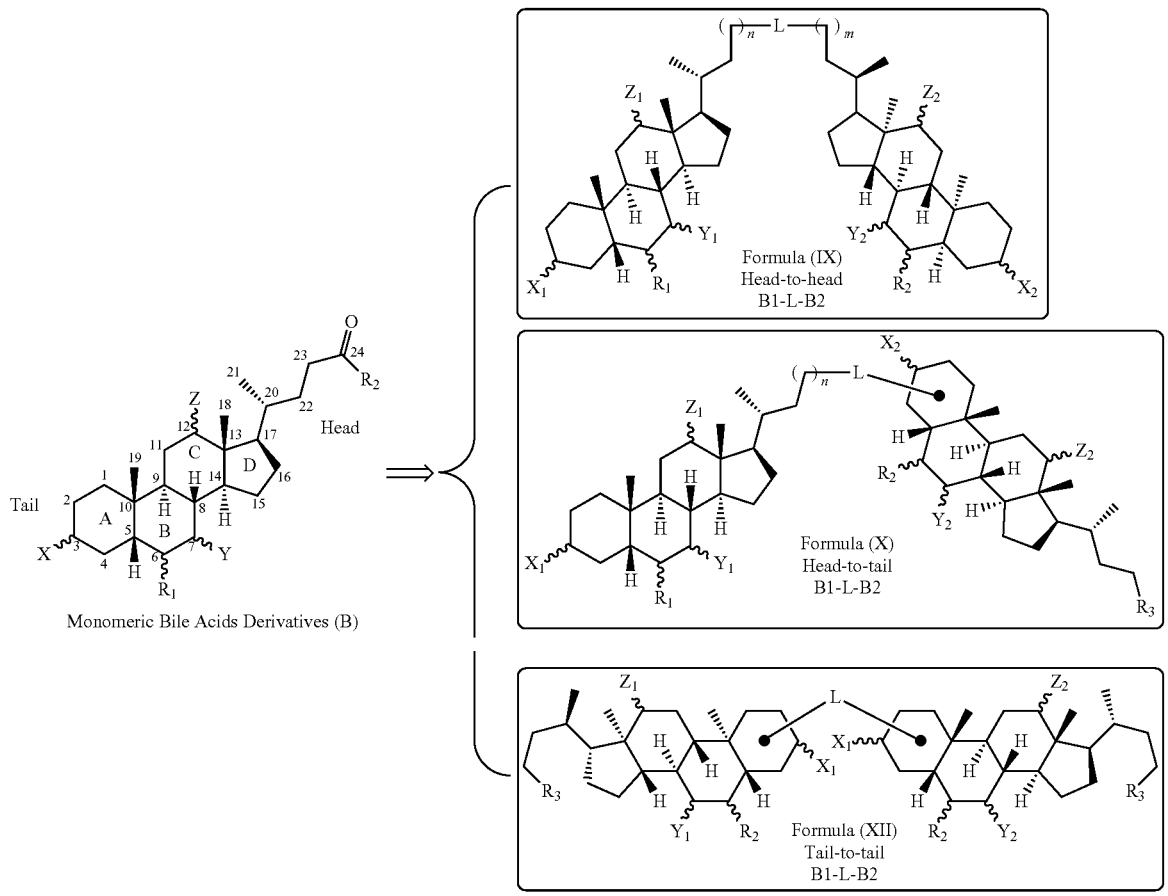

We also tested and found anti-HBV and anti-HDV activity for trimeric bile acid derivatives, though the activity of linear trimeric bile acid 3UUT (see table D) was not as high as the dimeric counterparts (FIG. 5, also see FIGS. 2 and 3). Active trimmers are encompassed by formula (XII) in the Table G.

TABLE G

Chemical design for trimeric bile acid derivatives.

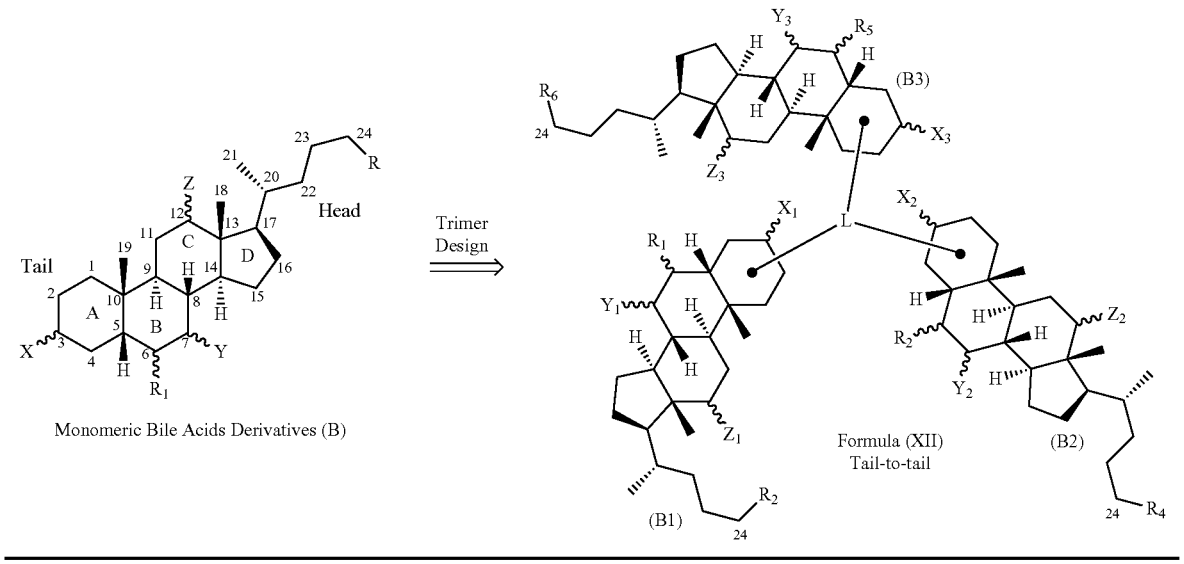

For the trimeric structure (XII) in Table G:

L is the conjugated linkage group between B1, B2 and B3. Wherein B1, B2 and B3 are monomeric bile acid derivatives. For the trimeric formula (XII), L is connected to the monomeric bile acid derivatives at any positions (the carbon atom or the substituent atoms thereon) of 1 to 24 via covalent bond. The number n, m and o can be any Arabic numerals.

PBADs inhibit HBV infection at the entry level. To dissect the anti-viral mechanism of PBADs, we conducted time course studies to find their action time windows. We found these PBADs were active when added before or during viral inoculation on the cells, but not post viral inoculation, indicating they may act on the early entry process (FIG. 3).

Figure 4:
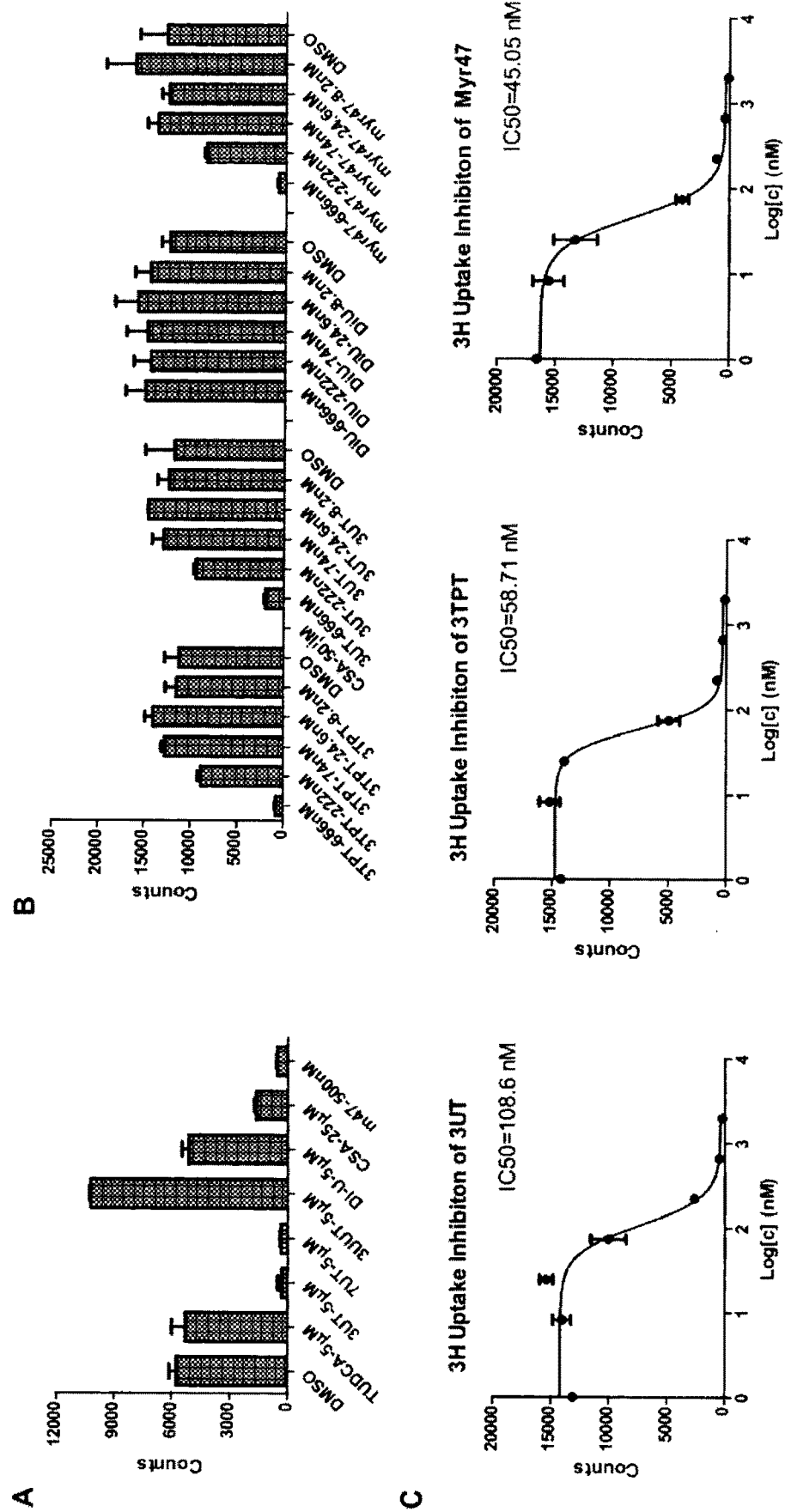
FIG. 4 Some PBADs significantly blocked substrate uptake by NTCP. (A) [3H] taurocholate uptake assay was conducted on HepG2-NTCP cells in the presence of indicated chemicals or myr47 (a peptide corresponding to the first 47 amino acids of the L envelope protein and with a myristoylation modification at the N-terminus). (B) Dose dependent inhibition of [3H] Taurocholate uptake by 3UT (NQL-012), 3TPT(NQL-018), DiU(NQL-009) and myr47. The indicated chemicals together with the [3H] taurocholate were added on HepG2-NTCP cells and incubated for 10 min, the [13H] taurocholate uptake efficiency was then determined. (C) IC50 of 3UT(NQL-012), 3TPT(NQL-018) and myr47 for inhibiting NTCP-mediated [13H] taurocholate uptake. HepG2-NTCP cells were pretreated with indicated concentrations of 3UT(NQL-012), 3TPT(NQL-018) or Myr47 for 2 hrs before uptake assay.

PBADs significantly block substrate uptake of NTCP. We further analyzed the influence of PBAD treatment on NTCP mediated [3H] labeled taurocholate uptake (FIG. 4). In the co-incubation assay, most of the PBADs such as 3-UT (NQL-012), 7-UT (NQL-015) and 3TPT (NQL-018) that efficiently inhibited HBV and HDV infection also inhibited NTCP substrate uptake, with a significantly higher efficiency than that of TUDCA (FIG. 4A,B). We also evaluated the uptake inhibition of 3UT(NQL-012) and 3TPT(NQL-018) in the pretreatment assay. The results showed the IC50 of 3UT (NQL-012) is 108.6 nM, 3TPT(NQL-018) is 58.7 nM, close to IC50 of a positive control reagent (preS1 peptide of HBV L protein) (FIG. 4C).

The IC50 of PBADs of HBV infection on HepG2-NTCP cells. We conducted dose dependence inhibition assay to determine more quantitatively the IC50 of the PBADs. As illustrated in Figure. 5, the 3TPT(NQL-018) showed the best anti-HBV activity, with an IC50 of 51.04 nM, about 100 times lower than that of its monomer precursor (TUDCA). The potency of 3UT(NQL-012) and DiU(NQL-009) was slightly lower than 3TPT(NQL-018). Their IC50 values were 100 nM and 110 nM, respectively.

Figure 6:
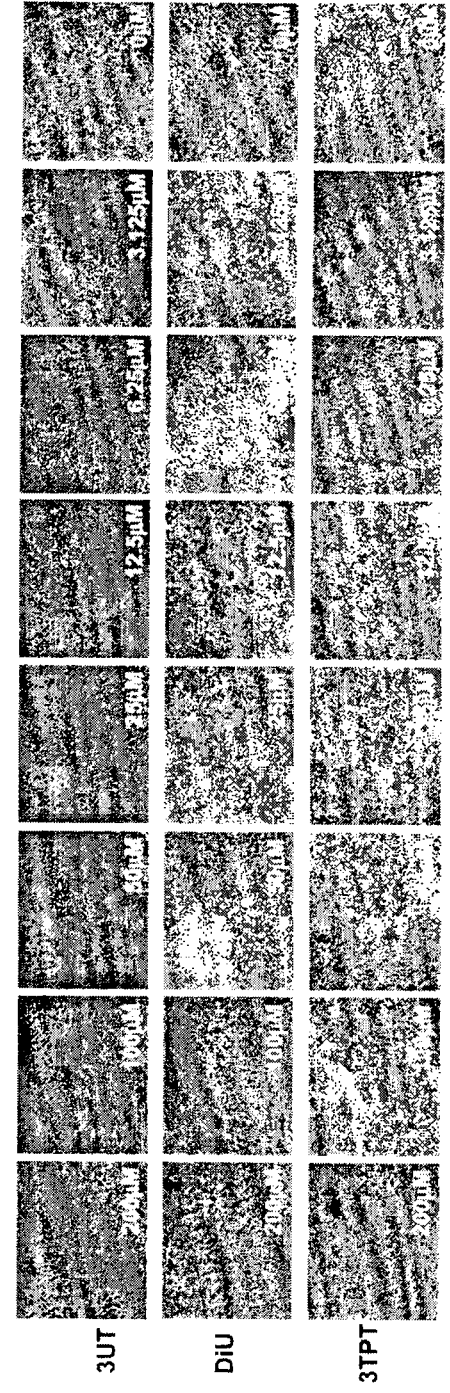
FIG. 6 Toxicity of 3UT(NQL-012), DiU(NQL-009) and 3TPT(NQL-018) in cell cultures. HepG2-NTCP cells were incubated with 3UT(NQL-012), DiU(NQL-009) or 3TPT (NQL-018) at indicated concentrations for 48 hrs, cell viability was evaluated and images were captured at 5 dpi.

In vitro cytotoxicity of PBADs. We also conducted experiments to determine the LD50 on HepG2-NTCP cell line of the three PBADs (3-UT (NQL-012), DIU (NQL-009), 3TPT (NQL-018)). We treated cells by different concentrations of PBADs for 48 hrs and captured the images of cells after they were further cultured for 3 days in PMM. As shown in FIG. 6, treatment by 3UT (NQL-012) led to significant cell death at high concentration, with a LD50 near 25 µM. No detectable cytotoxicity was observed upon treatment of DIU(NQL-009) and 3TPT(NQL-018) up to 200 µM, which is 2000-4000 folds higher than its inhibitory concentration for HBV infection.

Figure 7:
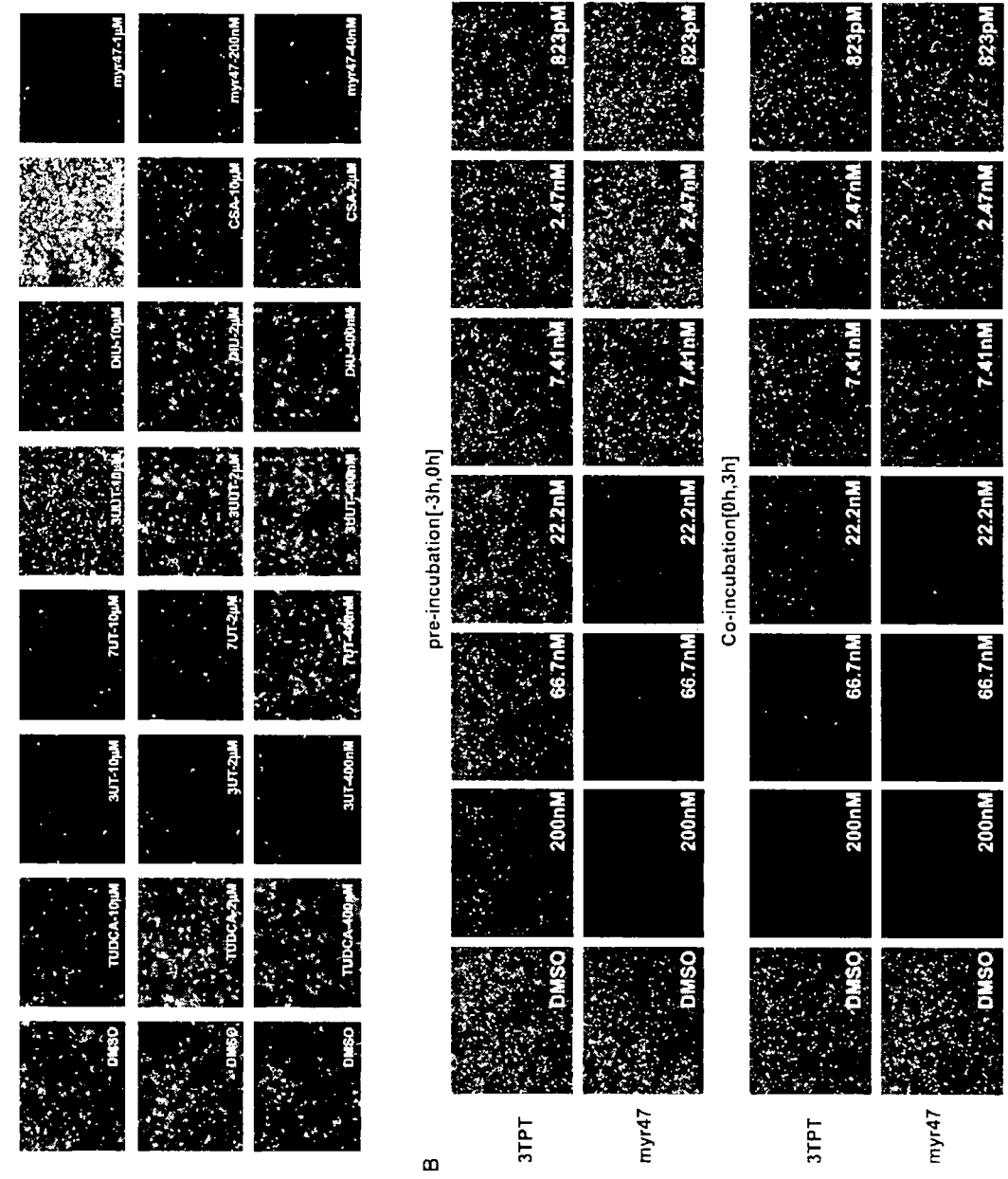
FIG. 7 PBAD inhibited viral infection by targeting NTCP and blocked the interaction between NTCP and the HBV preS1 domain. (A) Binding of FITC-preS1 peptide to NTCP was blocked by PBAD. FITC-preS1 binding assay was conducted in the presence of indicated concentrations of chemicals. (B) Dose dependence assay of 3TPT(NQL-018) and myr47 for inhibiting the binding between FITC-preS1 peptide and NTCP. The binding was evaluated as the HepG2-NTCP cells were pre-incubated (upper panel) or co-incubated (lower panel) with the chemicals for 3 hrs.
Figure 8:
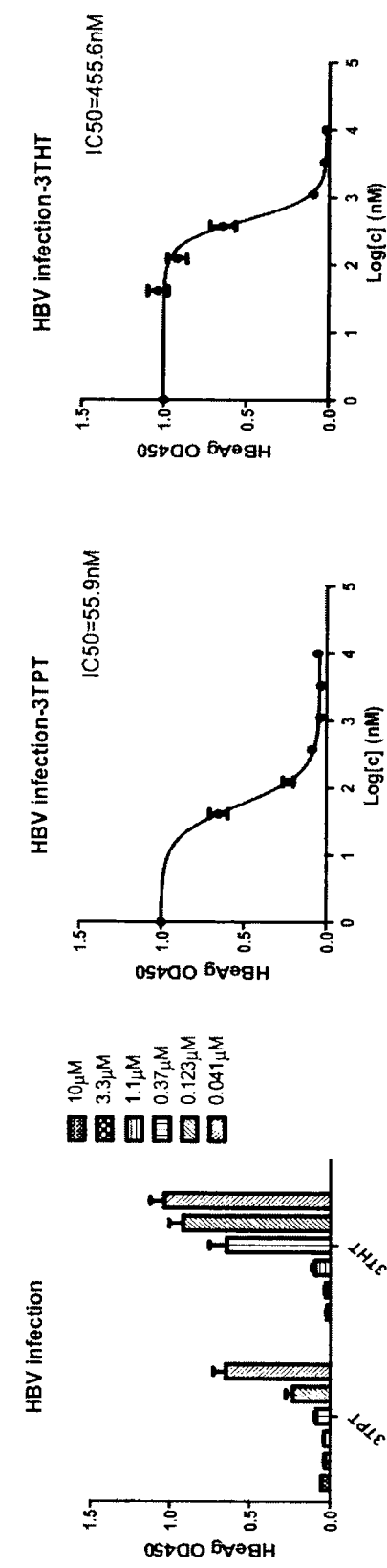
FIG. 8 The influence of the length of linkage group on the activity of PBADs. We compared the activity of 3TPT (NQL-018) (bis-ester bond with 5 carbons in the middle) and 3THT (bis-ester bond with 7 carbons in the middle). HepG2-NTCP cells were infected by HBV in the presence of indicated concentrations of PBADs. The level of secreted HBeAg in the medium was examined at 5 dpi, and the IC50 value of them are indicated in the figures.
Figure 9:
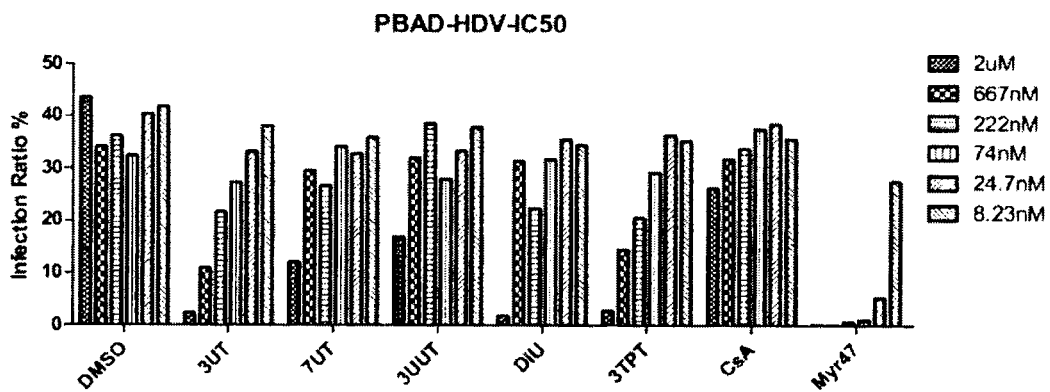
FIG. 9 PBADs dose dependently inhibited HDV infection. HepG2-NTCP cells were infected with HDV in the presence of indicated PBADs with different concentrations. At day 6 post infection, the intracellular delta antigen was stained with FITC conjugated monoclonal antibody 4G5. HDV infection ratio was calculated accordingly.

PBADs inhibit viral infection by targeting NTCP and block its interaction with HBV preS1 domain. We employed FITC-preS1 peptide binding assay to examine whether PBADs block FITC-preS1 binding to NTCP. As shown in FIG. 7A, some PBADs indeed blocked the interaction between preS1 and NTCP, and the efficiency was correlated to their anti-HBV activity. Interestingly, high concentration of 3UUT(NQL-016), DIU(NQL-009) and CSA led to the aggregation of FITC-preS1 peptide, which may be attributed to their hydrophobic properties. Furthermore, we tested the effect of pretreatment versus co-incubation of 3TPT(NQL-018) at different concentrations. The FIG. 7B showed that the effect of pretreatment of 3TPT(NQL-018) was not as strong as that of co-incubation.

Figure 10:
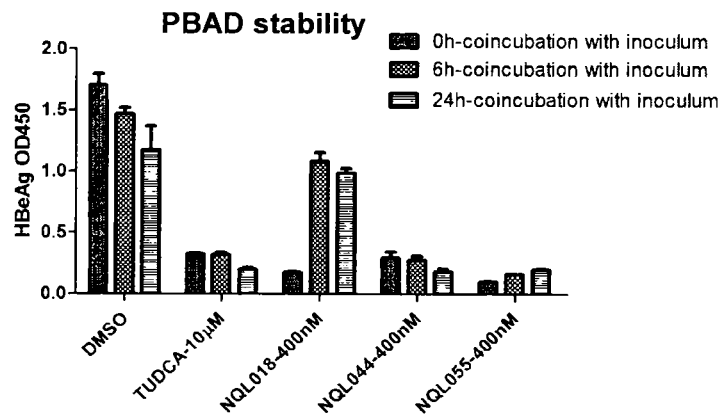
FIG. 10 The influence of the linkage groups on the in vitro stability of PBADs. TUDCA, NQL018, NQL044, and NQL055 were incubated with HBV inocula of different times before viral infection, and present in the inocula during infection period. The level of secreted HBeAg was detected by ELISA at 5 dpi. Only NQL018 showed decreased activity after long time incubation.

The in vitro stability of PBADs could PBADs could be enhanced by optimization of the linkage bond. We conducted stability analysis of several PBADs with similar structure but of different linkage. FIG. 10 showed that the ester bond based 3TPT(NQL018, table H) is not stable upon long time incubation with the inoculum. In comparison, NQL044 and NQL055 are much more stable as no significant potency decrease was observed. This indicates the in vitro and in vivo stability is to a large extent determined by the feature of the linkage groups.

TABLE H
Chemical structural examples of dimeric bile acids derivatives of UDCA with different linkages.
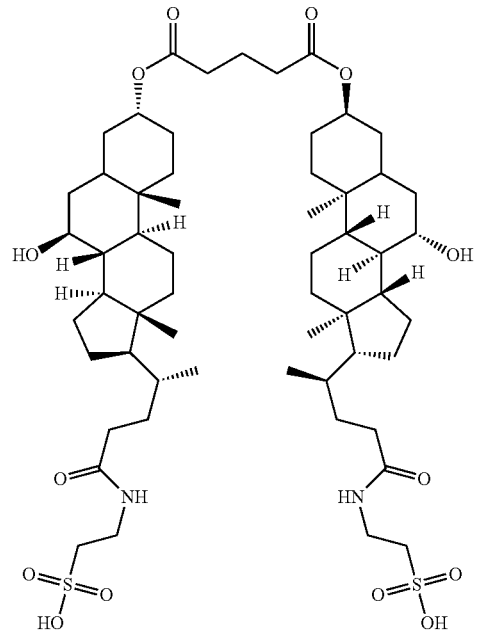
NIBS-Qi-WHLi-018
NQL-018(3-TPT)
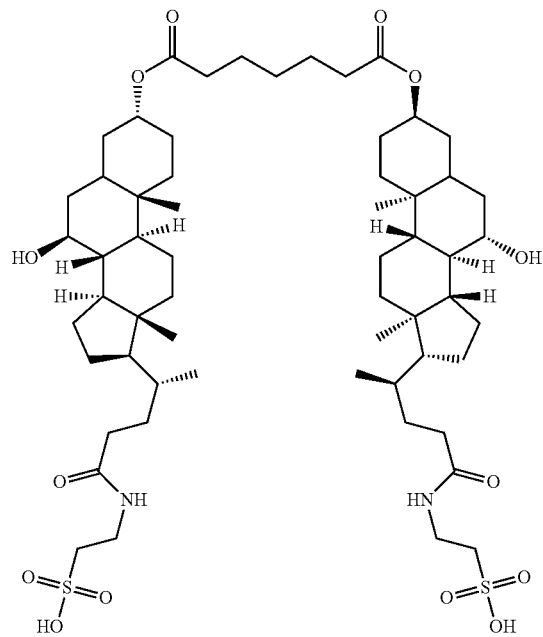 [SMILES: C[C@H](CCC(=O)NCCS(=O)(=O)O)[C@H]1CC[C@H]2[C@@H]3[C@@H](O)CC4C[C@H](OC(=O)CCCCCC(=O)O[C@@H]5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-019
NQL-019

TABLE H-continued
Chemical structural examples of dimeric bile acids derivatives of UDCA with different linkages.
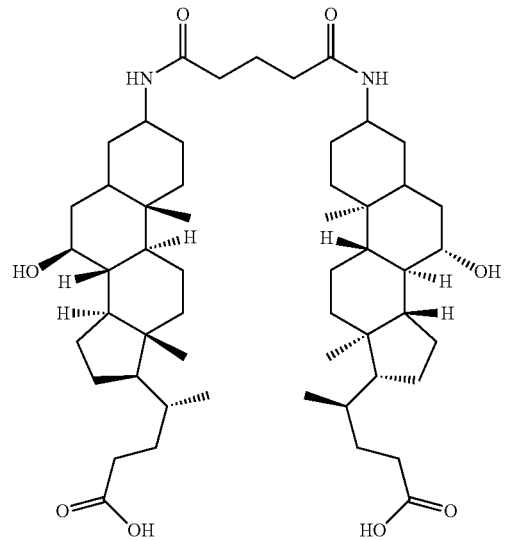 [SMILES: C[C@H](CCC(=O)O)[C@H]1CC[C@H]2[C@@H]3[C@@H](O)CC4CC(NC(=O)CCCC(=O)NC5CC[C@@]6(C)C(C5)C[C@H](O)[C@H]5[C@@H]7CC[C@H]([C@H](C)CCC(=O)O)[C@@]7(C)CC[C@@H]56)CC[C@]4(C)[C@H]3CC[C@]12C]
NIBS-Qi-WHLi-020
NQL-020
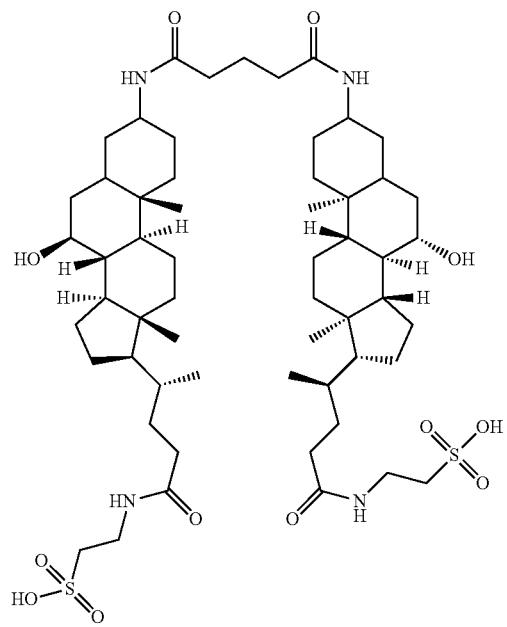 [SMILES: C[C@H](CCC(=O)NCCS(=O)(=O)O)[C@H]1CC[C@H]2[C@@H]3[C@@H](O)CC4CC(NC(=O)CCCC(=O)NC5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-021
NQL-021

TABLE H-continued
Chemical structural examples of dimeric bile acids derivatives of UDCA with different linkages.
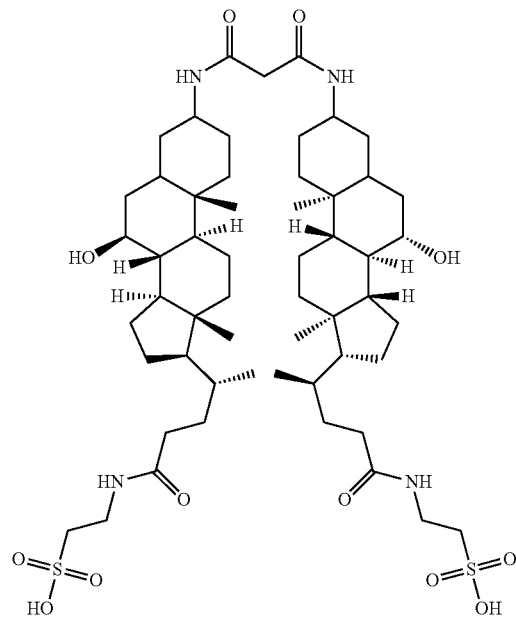 [SMILES: C[C@H](CCC(=O)NCCS(=O)(=O)O)[C@H]1CC[C@H]2[C@@H]3[C@@H](O)CC4CC(NC(=O)CC(=O)NC5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-022
NQL-022
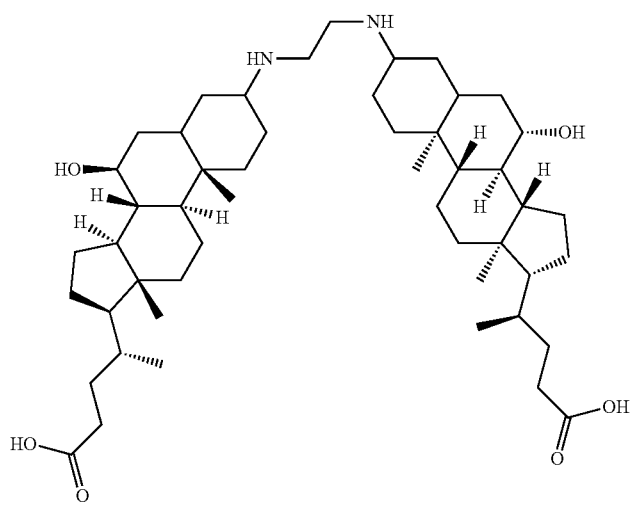
NIBS-Qi-WHLi-023
NQL-023

137 138
TABLE H-continued
Chemical structural examples of dimeric bile acids derivatives of UDCA with different linkages.
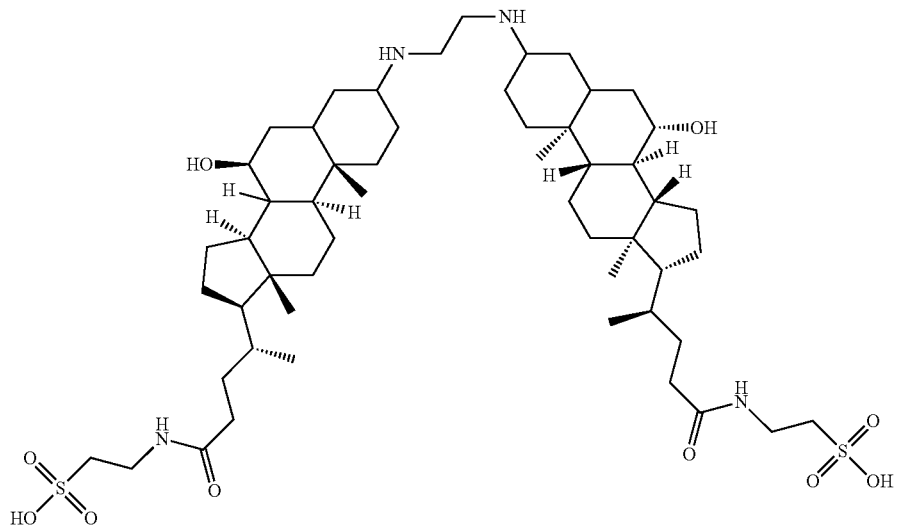 [SMILES: C[C@H](CCC(=O)NCCS(=O)(=O)O)[C@H]1CC[C@H]2C3[C@@H](O)CC4CC(NCCNC5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-024
NQL-024
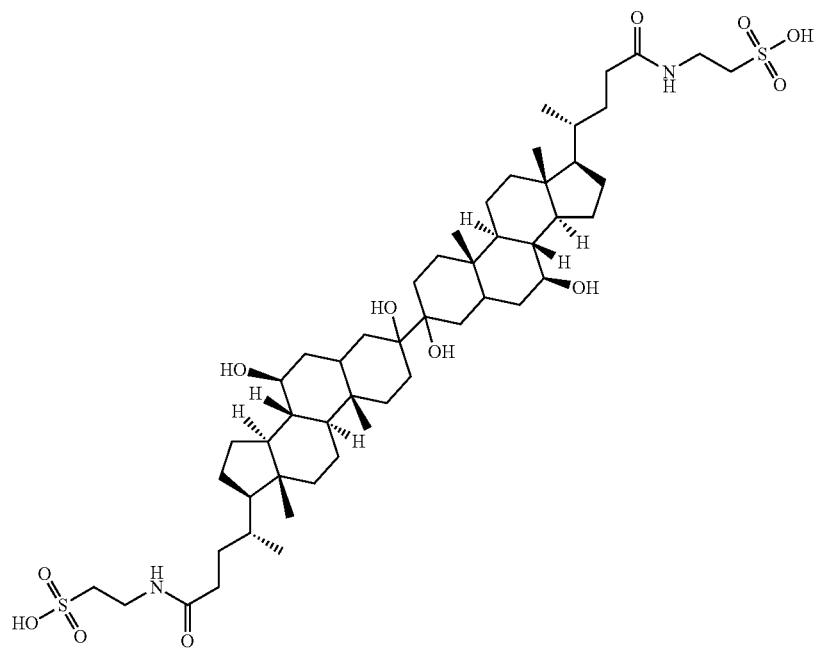 [SMILES: C[C@H](CCC(=O)NCCS(=O)(=O)O)[C@H]1CC[C@H]2[C@@H]3[C@@H](O)CC4CC(O)(C5(O)CC[C@@]6(C)C(C[C@H](O)[C@H]7[C@@H]8CC[C@H]([C@H](C)CCC(=O)NCCS(=O)(=O)O)[C@@]8(C)CC[C@@H]76)C5)CC[C@]4(C)[C@H]3CC[C@]12C]
NIBS-Qi-WHLi-025
NQL-025

TABLE H-continued
Chemical structural examples of dimeric bile acids derivatives of UDCA with different linkages.
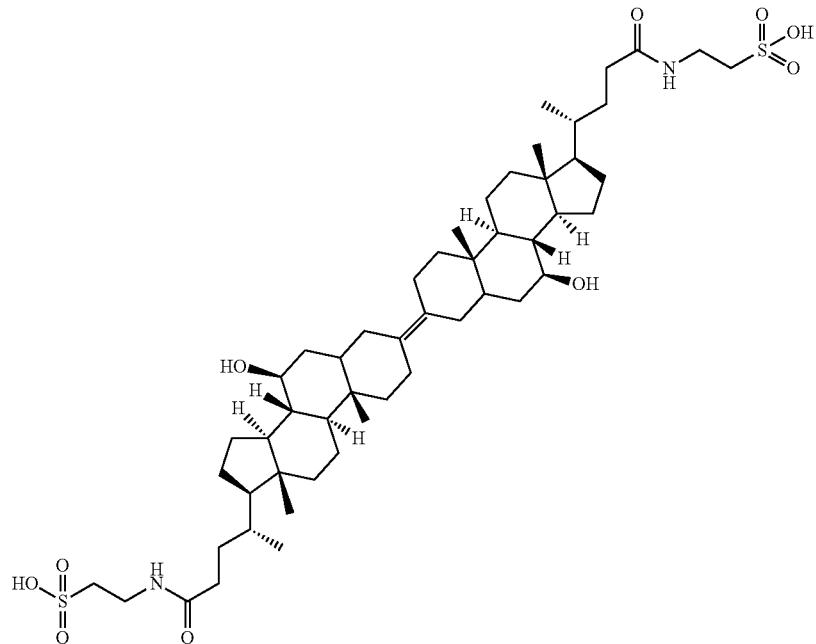 [SMILES: C[C@H](CCC(=O)NCCS(=O)(=O)O)[C@H]1CC[C@H]2[C@@H]3[C@@H](O)CC4C/C(=C5\CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-026
NQL-026
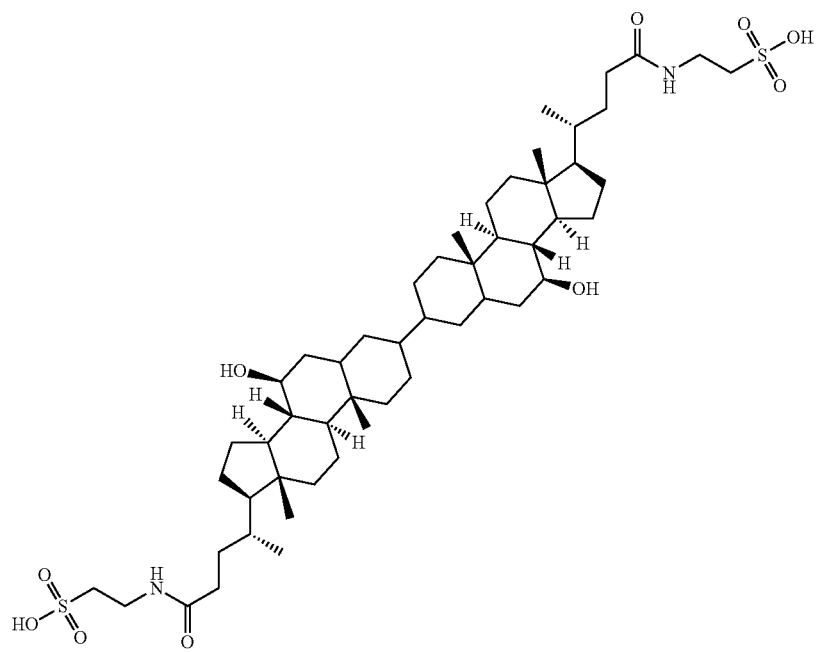 [SMILES: C[C@H](CCC(=O)NCCS(=O)(=O)O)[C@H]1CC[C@H]2[C@@H]3[C@@H](O)CC4CC(C5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-027
NQL-027

TABLE H-continued
Chemical structural examples of dimeric bile acids derivatives of UDCA with different linkages.
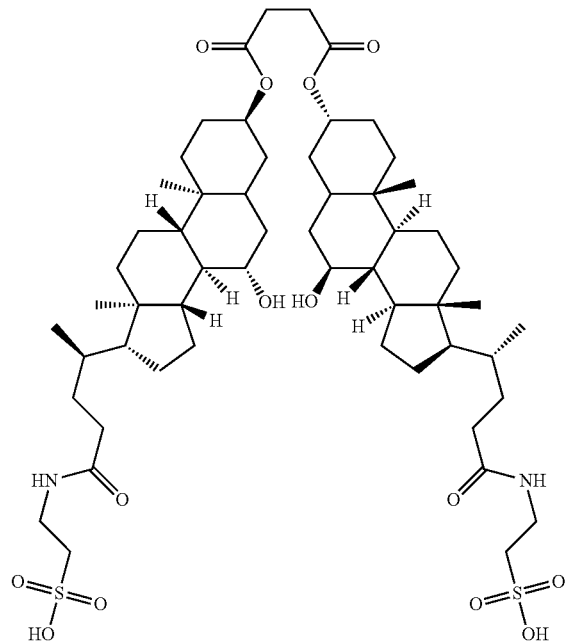 [SMILES: C[C@H](CCC(=O)NCCS(=O)(=O)O)[C@H]1CC[C@H]2[C@@H]3[C@@H](O)CC4C[C@H](OC(=O)CCC(=O)O[C@@H]5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-028
NQL-028
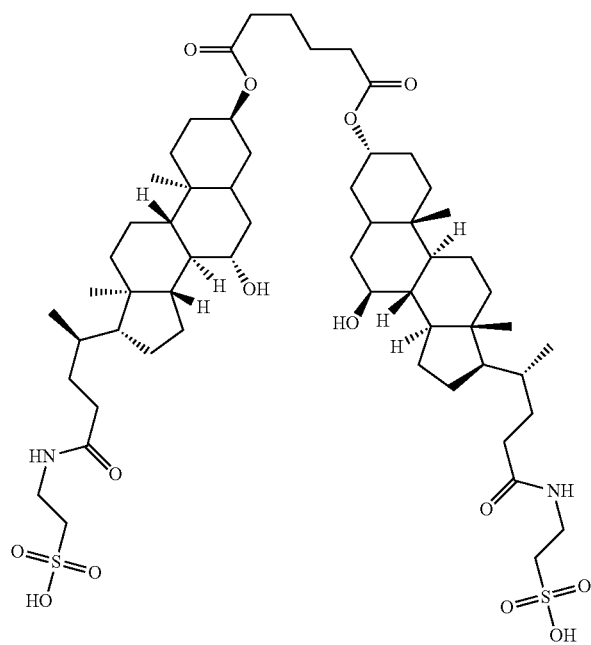 [SMILES: C[C@H](CCC(=O)NCCS(=O)(=O)O)[C@H]1CC[C@H]2[C@@H]3[C@@H](O)CC4C[C@H](OC(=O)CCCCC(=O)O[C@@H]5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NIBS-Qi-WHLi-029
NQL-029

TABLE H-continued
Chemical structural examples of dimeric bile acids derivatives of UDCA with different linkages.
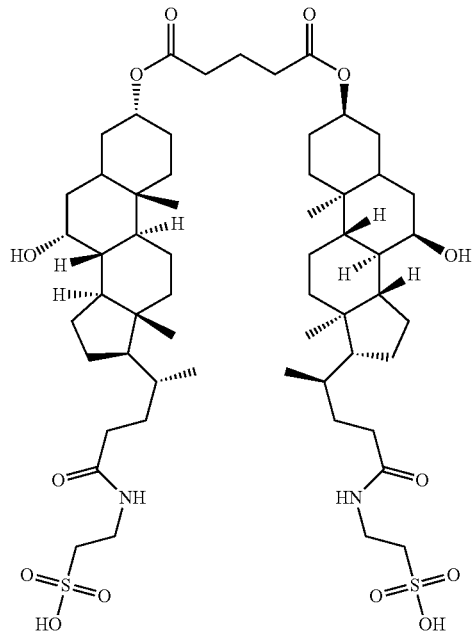
NIBS-Qi-WHLi-030
NQL-030
TCDCA-TCDCA
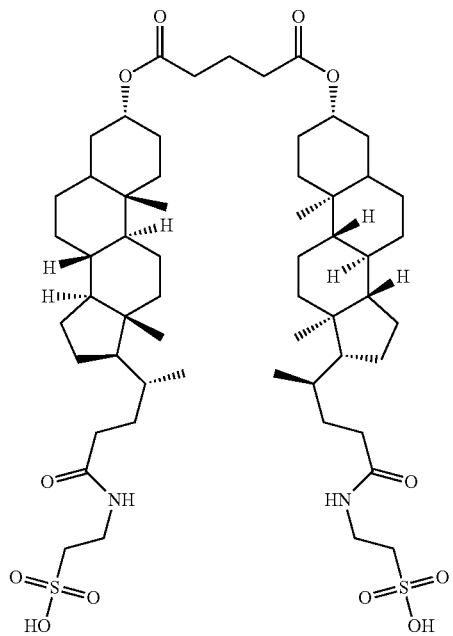
NIBS-Qi-WHLi-032
NQL-032
TLCA-TLCA

TABLE H-continued
Chemical structural examples of dimeric bile acids derivatives of UDCA with different linkages.
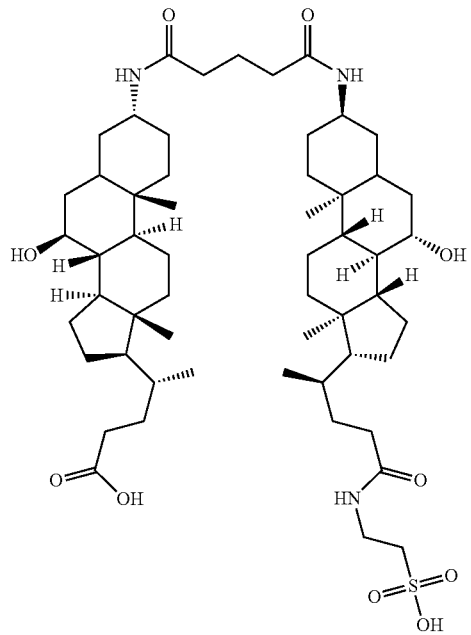
NIBS-Qi-WHLi-043
NQL-043
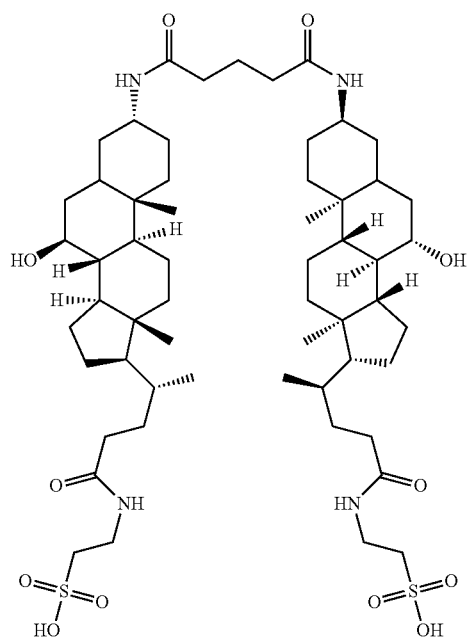
NIBS-Qi-WHLi-044
NQL-044

TABLE H-continued
Chemical structural examples of dimeric bile acids derivatives of UDCA with different linkages.
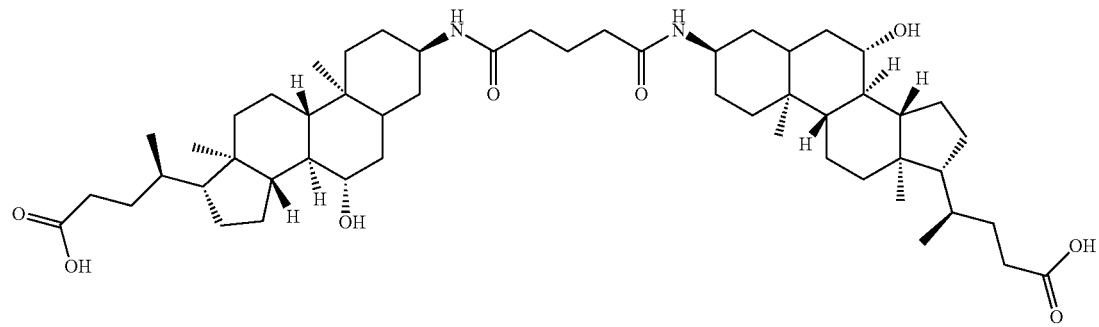 [SMILES: C[C@H](CCC(=O)O)[C@H]1CC[C@H]2[C@@H]3[C@@H](O)CC4C[C@H](NC(=O)CCCC(=O)N[C@@H]5CC[C@@]6(C)C(C5)C[C@H](O)[C@H]5[C@@H]7CC[C@H]([C@H](C)CCC(=O)O)[C@@]7(C)CC[C@@H]56)CC[C@]4(C)[C@H]3CC[C@]12C]
NQL-048
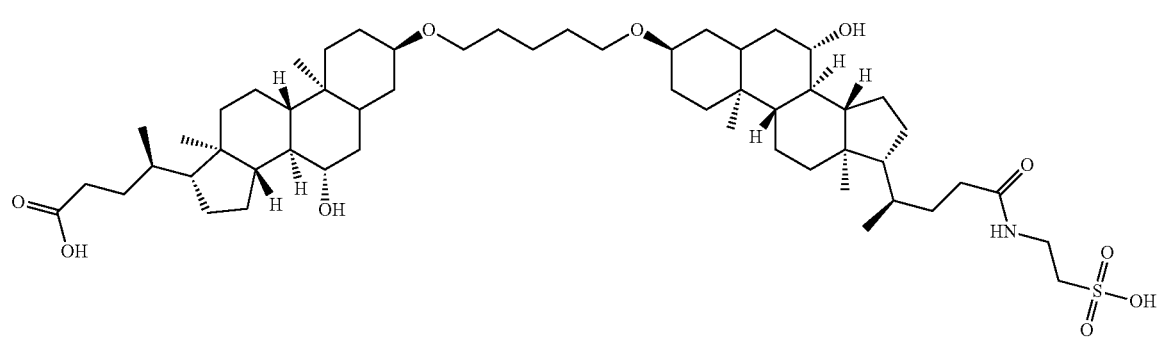 [SMILES: C[C@H](CCC(=O)O)[C@H]1CC[C@H]2[C@@H]3[C@@H](O)CC4C[C@H](OCCCCCO[C@@H]5CC[C@@]6(C)C(C5)C[C@H](O)[C@H]5[C@@H]7CC[C@H]([C@H](C)CCC(=O)NCCS(=O)(=O)O)[C@@]7(C)CC[C@@H]56)CC[C@]4(C)[C@H]3CC[C@]12C]
NQL-052
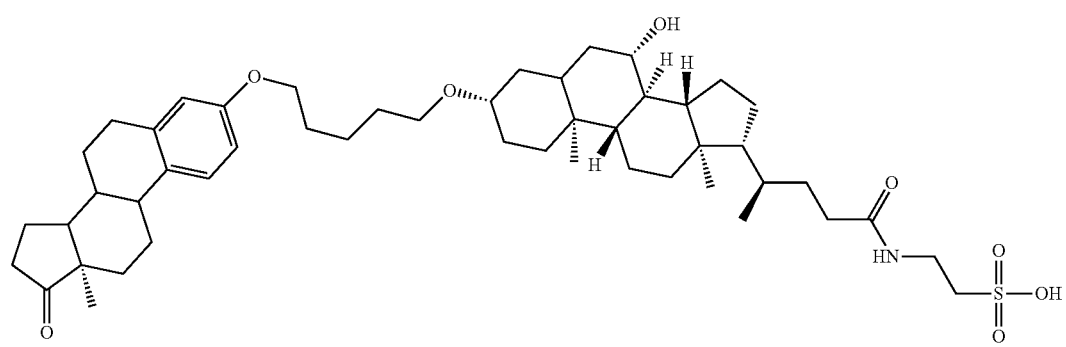 [SMILES: C[C@H](CCC(=O)NCCS(=O)(=O)O)[C@H]1CC[C@H]2[C@@H]3[C@@H](O)CC4C[C@@H](OCCCCCOc5ccc6c(c5)CCC5C6CC[C@@]6(C)C(=O)CCC56)CC[C@]4(C)[C@H]3CC[C@]12C]
NQL-053
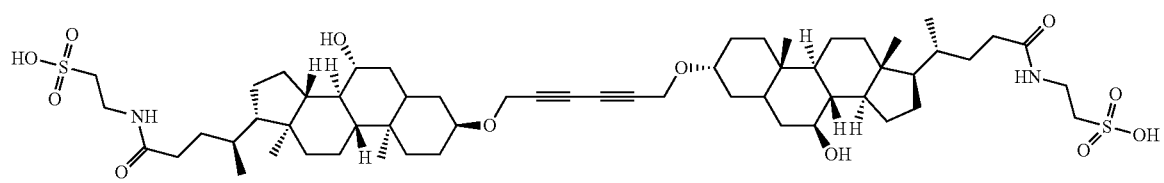
NQL-054
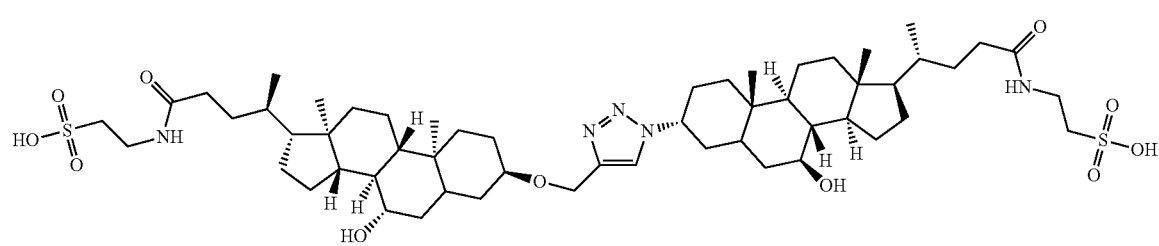 [SMILES: C[C@H](CCC(=O)NCCS(=O)(=O)O)[C@H]1CC[C@H]2[C@@H]3[C@@H](O)CC4C[C@H](OCc5cn([C@@H]6CC[C@@]7(C)C(C6)C[C@H](O)[C@H]6[C@@H]8CC[C@H]([C@H](C)CCC(=O)NCCS(=O)(=O)O)[C@@]8(C)CC[C@@H]67)nn5)CC[C@]4(C)[C@H]3CC[C@]12C]

TABLE H-continued
Chemical structural examples of dimeric bile acids derivatives of UDCA with different linkages.
NQL-055
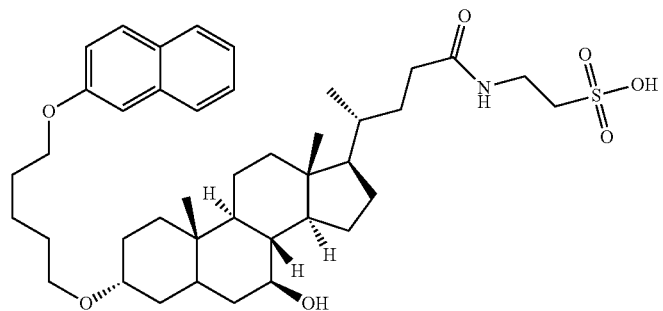 [SMILES: C[C@H](CCC(=O)NCCS(=O)(=O)O)[C@H]1CC[C@H]2[C@@H]3[C@@H](O)CC4C[C@H](OCCCCCOc5ccc6ccccc6c5)CC[C@]4(C)[C@H]3CC[C@]12C]
NQL-056
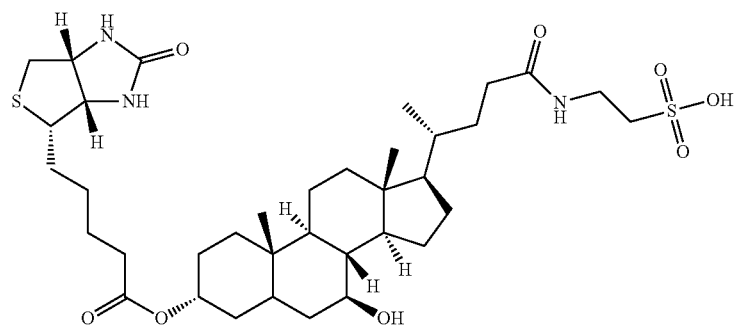 [SMILES: C[C@H](CCC(=O)NCCS(=O)(=O)O)[C@H]1CC[C@H]2[C@@H]3[C@@H](O)CC4C[C@H](OC(=O)CCCC[C@@H]5SC[C@@H]6NC(=O)N[C@@H]65)CC[C@]4(C)[C@H]3CC[C@]12C]
NQL-057
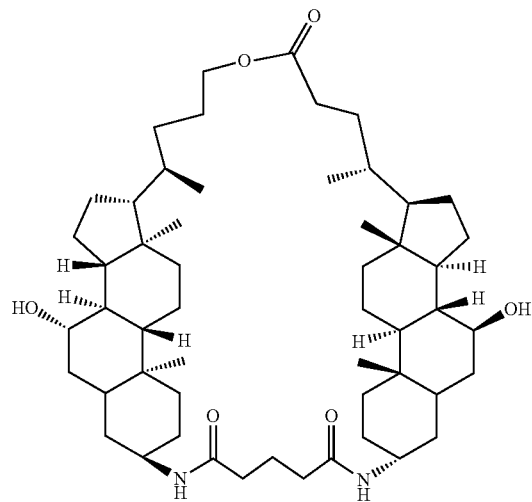 [SMILES: C[C@@H]1CCCOC(=O)CC[C@@H](C)[C@H]2CC[C@H]3[C@@H]4[C@@H](O)CC5C[C@@H](CC[C@]5(C)[C@H]4CC[C@]23C)NC(=O)CCCC(=O)N[C@@H]2CC[C@@]3(C)C(C2)C[C@H](O)[C@H]2[C@@H]4CC[C@H]1[C@@]4(C)CC[C@@H]23]
NQL-058

TABLE H-continued

Chemical structural examples of dimeric bile acids derivatives of UDCA with different linkages.

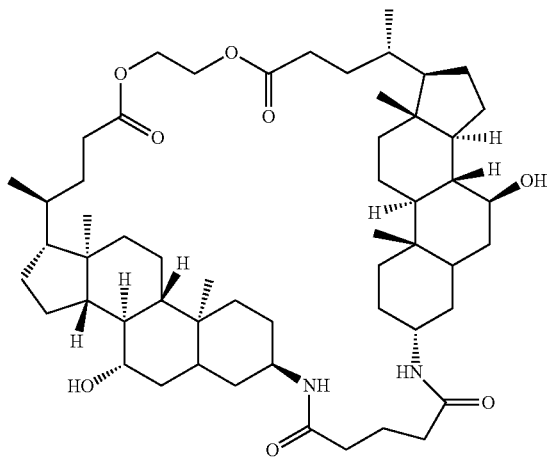 [SMILES: C[C@H]1CCC(=O)OCCOC(=O)CC[C@H](C)[C@H]2CC[C@H]3[C@@H]4[C@@H](O)CC5C[C@@H](CC[C@]5(C)[C@H]4CC[C@]23C)NC(=O)CCCC(=O)N[C@@H]2CC[C@@]3(C)C(C2)C[C@H](O)[C@H]2[C@@H]4CC[C@H]1[C@@]4(C)CC[C@@H]23]

NQL-059

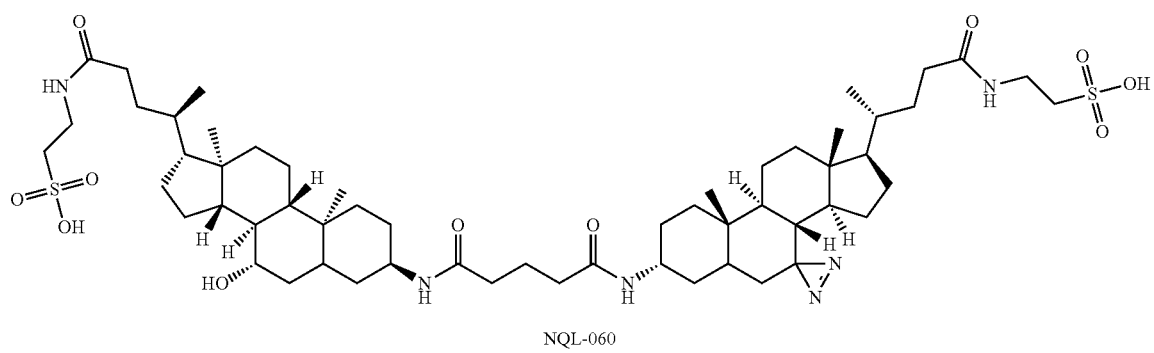

NQL-060

Figure 11:
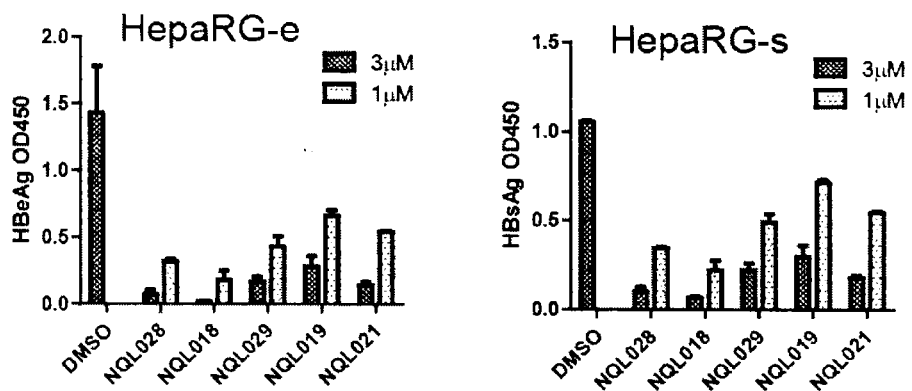
FIG. 11 HepaRG cells were infected with HBV in the presence of indicated PBADs. The level of secreted HBsAg and HBeAg was detected by ELISA at 5 dpi.

The antiviral potency of PBADs is also repeatable on other HBV infection system (HepaRG) with similar inhibition profile. As showed in FIG. 11, we conducted HBV infection assay on HepaRG cells, in which endogenous NTCP expression could be induced upon DMSO. HBV infection was conducted in the presence of NQL028, NQL018, NQL029, NQL019 and NQL021, all of which were bis-ester based PBADs with different linkage length. All of them inhibited HBV infection and the inhibition profile is similar to the result from HBV infection on HepG2-NTCP cells.

Figure 12:
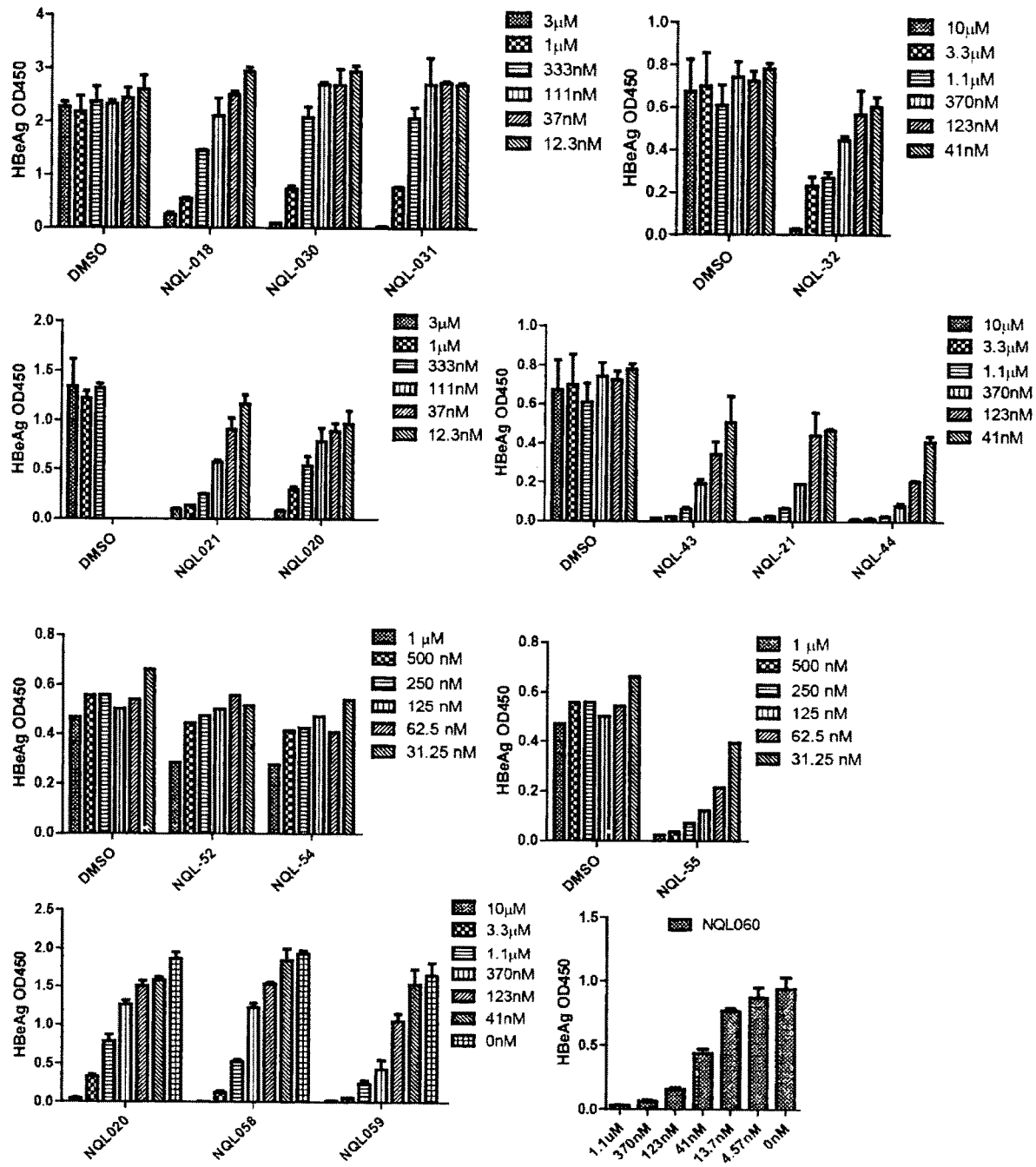
FIG. 12 Structure activity relationships analysis of different PBADs across a variety of monomers and linkages. HepG2-NTCP cells were infected with HBV in the presence of the indicated PBADs with different concentration. The level of secreted HBeAg was detected by ELISA at 5-6 dpi.

Structure activity relationship analysis of the PBADs. In FIG. 12, we showed the results of HepG2-NTCP cells infected with HBV in the presence of the indicated PBADs across a variety of monomers and linkages with different concentration. Each figure compared the efficacy of different PBADs (Table H) with similar structure, and the influence of their structure difference to antiviral potency was analyzed according to the results.

Materials and Methods. Cell culture. Human hepatocarcinoma cell line HepG2 was from American Type Culture Collection (ATCC); human hepatocarcinomacell line (Huh-7) was from the Cell Bank of Type Culture Collection, Chinese Academy of Sciences. They were cultured with Dulbecco's Modification of Eagle's Medium (DMEM; Invitrogen) supplemented with 10% fetal bovine serum (FBS, Gibco) at 37° C. with regular passage of every 2 days. HepG2NTCP stable cell line was generated from HepG2 cells and maintained in DMEM supplemented with 10% FBS and 500 µg/ml G418. HepG2-NTCP stable cell line were cultured on collagen (BD) coated plates or dishes. These cells were cultured in PTH maintenance medium (PMM) for 24 hrs before viral infection, peptide binding, substrate uptake, and other NTCP related experiments.

Peptide, antibodies and other reagents. FITC-pre-S1 peptide is derived from pre-S1 domain of HBV (C-type, GenBank accession no. EU554535.1) containing the first 59 residues, with an amino-terminal myristoylation modification and a carboxyl-terminal fluorescein isothiocyanate (FITC) conjugation; myr(+)47 peptide containing 2-47 residues of pre-S1 domain of HBV with N-terminal myristoylation. All these peptides were synthesis by SunLight peptides Inc. (Beijing, China). 1C10 is a mouse monoclonal antibody (mAb) recognizing the HBV core protein; 4G5 is a mouse mAb specifically targeting HDV delta antigen, #36 antibody is a mouse mAb specifically targeting NTCP. All mAbs were developed by the conventional hybridoma technology in the lab. Most natural bile acids are purchased form Sigma Aldrich. [3H] labeled taurocholate with activity of 15.3 Ci/mmol (0.185 TBq/mmol) and liquid scintillation cocktail (Ultima GOLD™ XR) were purchased from Perkin Elmer.

Virus production. Virions were produced from Huh7 cells after transfection of viral production plasmids. After transfection, cells were replenished with PMM, and virus containing medium were collected at 3 days and 6 days post transfection, centrifuged and stored at −80° C.

FITC-preS1 peptide binding assay. NTCP expressing cells were cultured in PTH maintenance medium (PMM) for 24 hrs before conducting this assay. For Immunofluorescence microscopy, cells were incubated with 400 nM FITC-pre-S1 peptide diluted in WME or PMM at 37° C. for about 2-3 hrs. Subsequently, cells were washed once by WME, and then directly visualized with a Fluorescence Microscope.

HBV and HDV infection assay. HepG2NTCP Cells were cultured in PMM for 12-24 hrs before infection, and then inoculated with 200 multiplicities of genome equivalents (mge) of HBV, or 500 mge of HDV in the presence of 5% PEG8000 in PMM at 37° C. for about 24 hrs. Chemicals to be tested were added to the cells as indicated in the specific assays. The inoculum was replenished by PMM post infection. The infections were detected at day 5 post infection (dpi).

[3H] substrate uptake assay. [3H]taurocholate uptake assay was conducted following a protocol as previously described(60). In general, HepG2-NTCP cells were cultured in PMM for 12-24 hrs, then were treated with or without indicated chemicals before uptake assay. For substrate uptake assay, cells were generally incubated with 0.5 µl (0.5 µCi) [3H]-taurocholate dissolved in Na+ Ringer's solutions for 10 mins at 37° C. with or without the presence of chemicals. Subsequently, cells were washed once by PBS and lysed by 100 µl of 1% TritonX-100 in H2O for 5 mins at room temperature. The lysate was transferred into liquid scintillation tube and mixed with 900 µl liquid scintillation cocktail (Ultima GOLD™ XR) (Perkin Elmer, USA). Liquid scintillation counting was performed on a Perkin Elmer 1450 LSC Liquid Scintillation Counter and Luminescence Counter.

ELISA assay for the detection of HBeAg and HBsAg. ELISA kits for HBeAg and HBsAg detection were from Wantai Pharm Inc. (Beijing, China). Supernatant from infected HepG2NTCP cells was collected on 2-5 days post infection. The secreted HBeAg and HBsAg in the culture medium was measured with a commercial kit from Wantai Pharm Inc (Beijing, China) by following the manufactory's instructions.

Immunostaining assay. For HBV infection, infected cells were washed twice with PBS and fixed in 3.7% paraformaldehyde (PFA) at room temperature for 10 mins. Subsequently, cells were permeabilized with 0.5% Trition X-100/PBS for 10 mins at room temperature, blocked with 3% BSA at 37° C. for 1 hour, and followed by incubating with 5 µg/ml mouse mAb1C10 which recognizes HBcAg, and followed by staining with FITC-conjugated secondary antibody. Nucleus was stained with DAPI in blue. The stained cells were imaged with the fluorescence microscope (Nikon). For HDV infection, on 5 dpi, HDV infected cells were fixed with 100% methanol at room temperature for 10 mins, intracellular delta antigens were then stained with 5 µg/ml of FITC conjugated 4G5 and nucleus were stained with DAPI in blue. Images were collected by an Eclipse Ti Fluorescence Microscope (Nikon) and a representative picture is shown.

Synthesis of PBADs. Preparing compounds of the general formula (I) to (VIII) from B1 or B2 by known or if not known, by the processes described below in details. The linkage L being generated from activated functional group on either B1 or B2 by construction of a covalent bond, in particular in the course of condensation or nucleophilic substitution reactions. Unprotective strategies were applied through the synthesis of 3-substituted or 3-linked polymeric bile acids. For example, condensation and substitution on bile acids is preferably happened in position 3, then position 7. Activated carboxylic acids, such as acid chlorides, anhydrides or aminoester will react directly with free alcohol or amino group to form ester or amide bond in the presence of organic or inorganic bases such as trialkylamine, pyridines, NaOH, KOH and so on. Suitable solvents for this type of reaction include tetrahydrofuran, methylene chloride, ether, acetonitile, dimethoxylethane and dimethylformamide. The reactions on the position of 7 and other positions can be achieved selectively by the use of suitable protection groups such as acetyl ester, trityl, alkyl(aryl)silyl, benzyl, allyl carbonate, Carboxybenzyl and ethers.

The preparation of bioactive polymeric bile acid derivatives were illustrated in the table C and D as exemplified by synthesis of 3-UT (NQL-012), 3-TPT (NQL-018) and 3-TAPT (NQL-044) from ursodeoxycholic acid (UDCA).

TABLE I

The synthetic route to 3-UT (NQL-012)

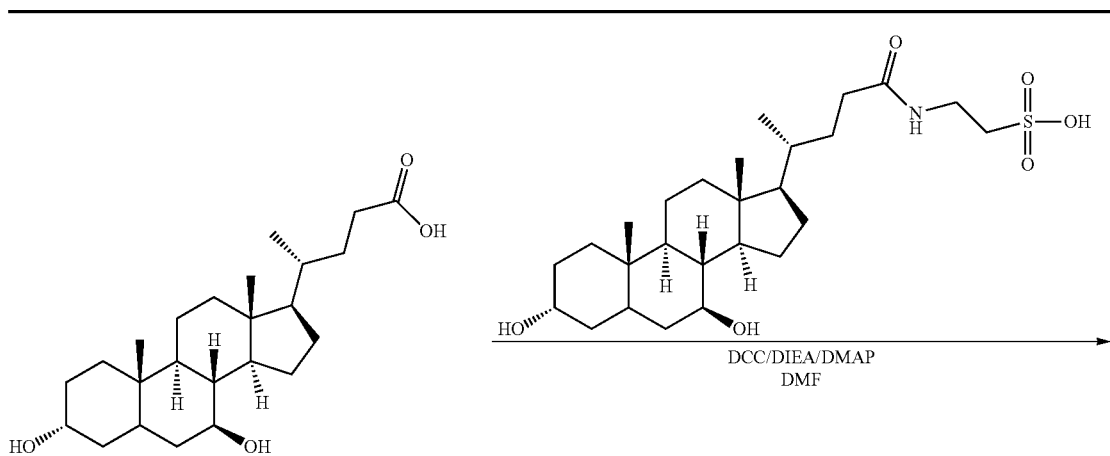

TABLE I-continued

The synthetic route to 3-UT (NQL-012)

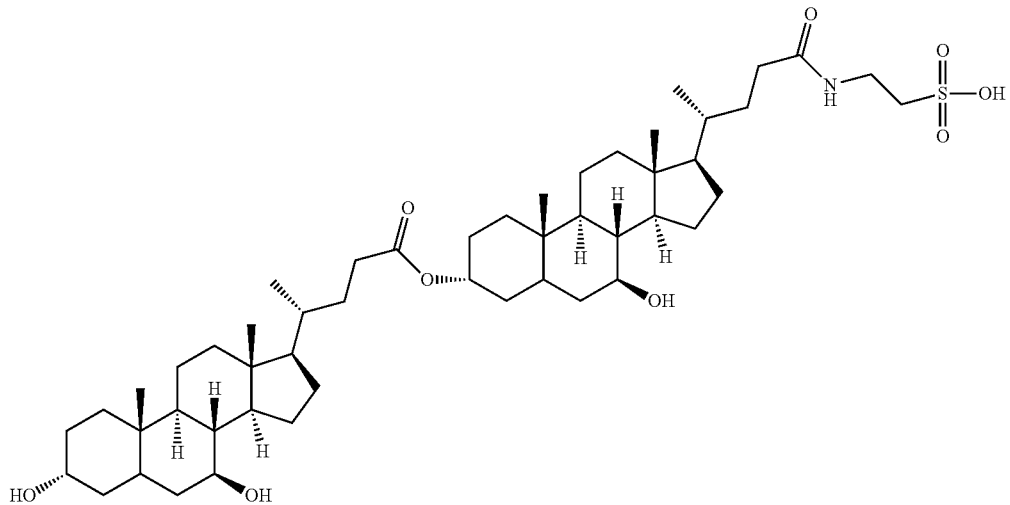

In a 10 mL, one-necked, round-bottomed flask, (4R)-4-((3R,7S,8R,9S,10S,13R,14S,17R)-3,7-dihydroxy-10,13-dimethylhexadecahydro-1H-cyclopenta [α] phenanthren-17-yl) pentanoic acid (UDCA) (23.5 mg, 0.06 mmol, 1.5 equiv) was dissolved in DMF (1 mL) at room temperature. Then 2-((4R)-4-((3R,7S,8R,9S,10S,13R,14S,17R)-3,7-dihydroxy-10,13-dimethylhexadecahydro-1H-cyclopenta [α] phenanthren-17-yl) pentanamido) ethanesulfonic acid (TUDCA) (20 mg, 0.04 mmol, 1.0 equiv), N,N-Diisopropylethylamine (DIEA) (15.5 mg, 0.12 mmol, 3.0 equiv), 4-Dimethylaminopyridine (DMAP) (5 mg, 0.04 mmol, 1.0 equiv) and N,N'-Dicyclohexylcarbodiimide (DCC) (16.5 mg, 0.08 mmol, 2.0 equiv) was added. After the addition was complete, the mixture was stirred at room temperature for 14 h. The mixture was concentrated and purified by preparative-HPLC to obtain target product as a white solid (5.0 mg).

The examples of Table J were obtained in analogy to Table I

Examples

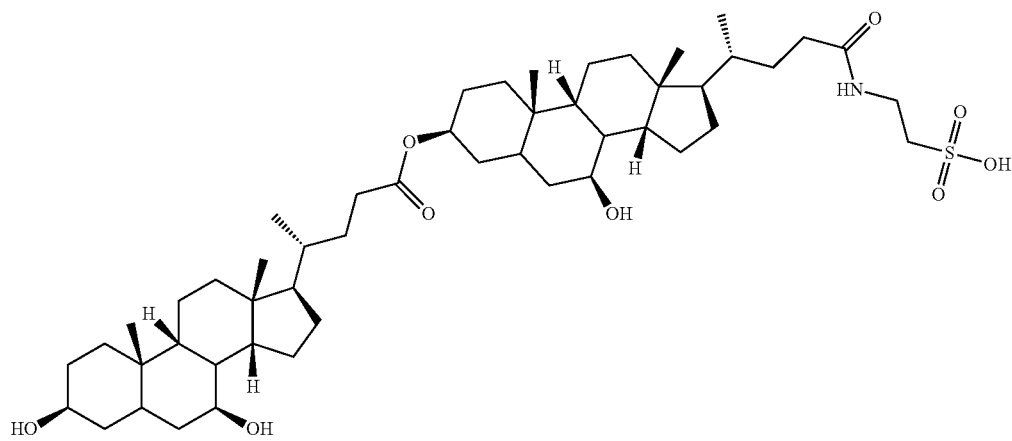 [SMILES: C[C@H](CCC(=O)O[C@H]1CC[C@@]2(C)C(C1)C[C@H](O)C1[C@H]3CC[C@H]([C@H](C)CCC(=O)NCCS(=O)(=O)O)[C@@]3(C)CC[C@H]12)[C@H]1CC[C@@H]2C3[C@@H](CC[C@@]21C)[C@@]1(C)CC[C@H](O)CC1C[C@@H]3O]

NQL-012
$C_{50}H_{83}NO_9S$
MW: 874
$[M - H]^-$: 873

157
158
-continued
Examples
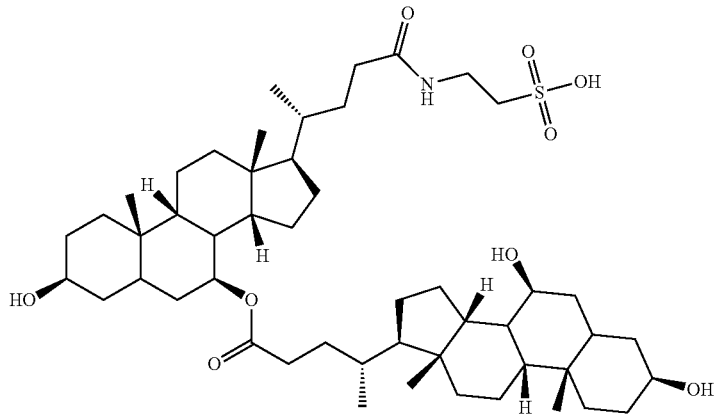 [SMILES: C[C@H](CCC(=O)NCCS(=O)(=O)O)[C@H]1CC[C@@H]2C3[C@@H](OC(=O)CC[C@@H](C)[C@H]4CC[C@@H]5C6[C@@H](CC[C@@]54C)[C@@]4(C)CC[C@H](O)CC4C[C@@H]6O)CC4C[C@@H](O)CC[C@]4(C)[C@@H]3CC[C@@]21C]
NQL-015
$C_{50}H_{85}NO_8S$
MW: 860
$[M - H]^-$: 859
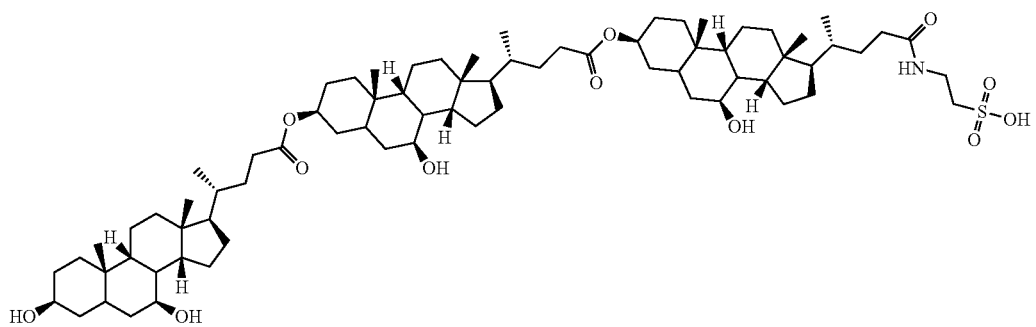 [SMILES: C[C@H](CCC(=O)O[C@H]1CC[C@@]2(C)C(C1)C[C@H](O)C1[C@H]3CC[C@H]([C@H](C)CCC(=O)O[C@H]4CC[C@@]5(C)C(C4)C[C@H](O)C4[C@H]6CC[C@H]([C@H](C)CCC(=O)NCCS(=O)(=O)O)[C@@]6(C)CC[C@H]45)[C@@]3(C)CC[C@H]12)[C@H]1CC[C@@H]2C3[C@@H](CC[C@@]21C)[C@@]1(C)CC[C@H](O)CC1C[C@@H]3O]
NQL-016
$C_{74}H_{121}NO_{12}S$
MW: 1248
$[M - H]^-$: 1247
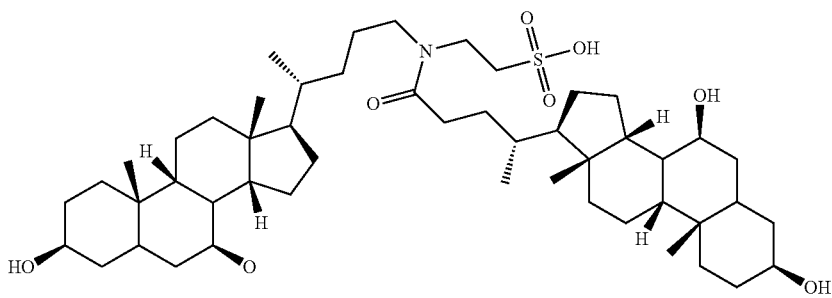 [SMILES: C[C@H](CCCN(CCS(=O)(=O)O)C(=O)CC[C@@H](C)[C@H]1CC[C@@H]2C3[C@@H](CC[C@@]21C)[C@@]1(C)CC[C@H](O)CC1C[C@@H]3O)[C@H]1CC[C@@H]2C3[C@@H](CC[C@@]21C)[C@@]1(C)CC[C@H](O)CC1C[C@@H]3O]
NQL-017
$C_{50}H_{83}NO_9S$
MW: 874
$[M - H]^-$: 873

| -continued |
|---|
| Examples |
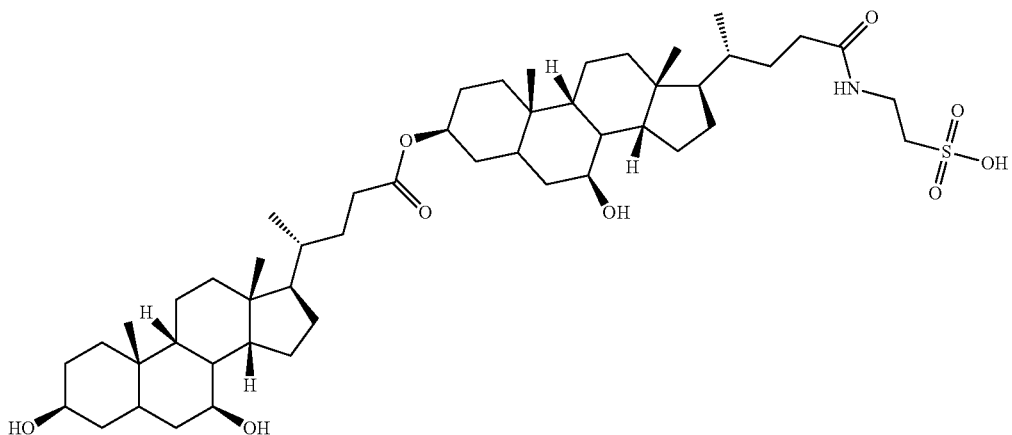 [SMILES: C[C@H](CCC(=O)O[C@H]1CC[C@@]2(C)C(C1)C[C@H](O)C1[C@H]3CC[C@H]([C@H](C)CCC(=O)NCCS(=O)(=O)O)[C@@]3(C)CC[C@H]12)[C@H]1CC[C@@H]2C3[C@@H](CC[C@@]21C)[C@@]1(C)CC[C@H](O)CC1C[C@@H]3O]
NQL-031
$C_{50}H_{83}NO_9S$
MW: 874
$[M - H]^-$: 873
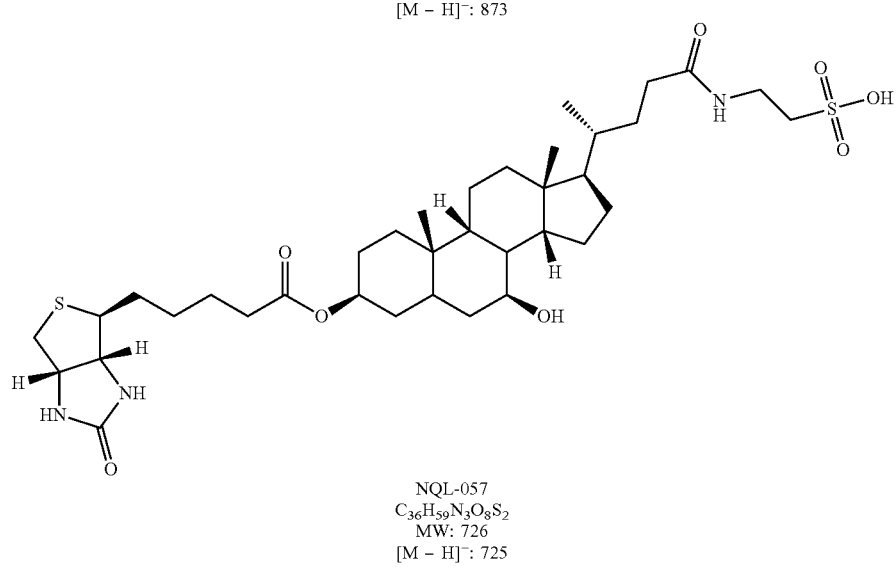
NQL-057
$C_{36}H_{59}N_3O_8S_2$
MW: 726
$[M - H]^-$: 725
| TABLE K |
|---|
| The synthetic route to NQL-018 |
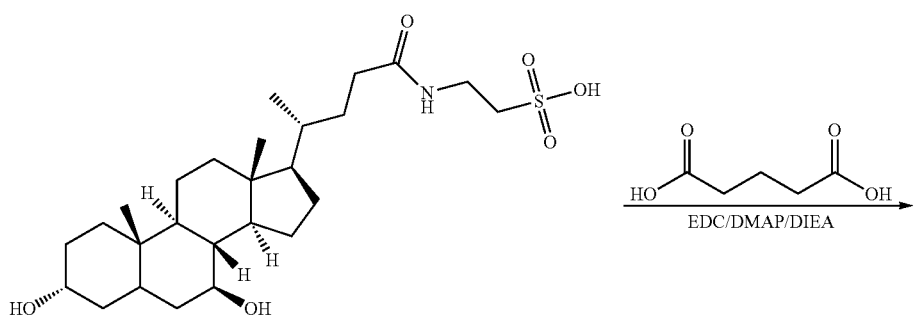 [SMILES: C[C@H](CCC(=O)NCCS(=O)(=O)O)[C@H]1CC[C@H]2[C@@H]3[C@@H](O)CC4C[C@H](O)CC[C@]4(C)[C@H]3CC[C@]12C ; O=C(O)CCCC(=O)O]

TABLE K-continued

The synthetic route to NQL-018

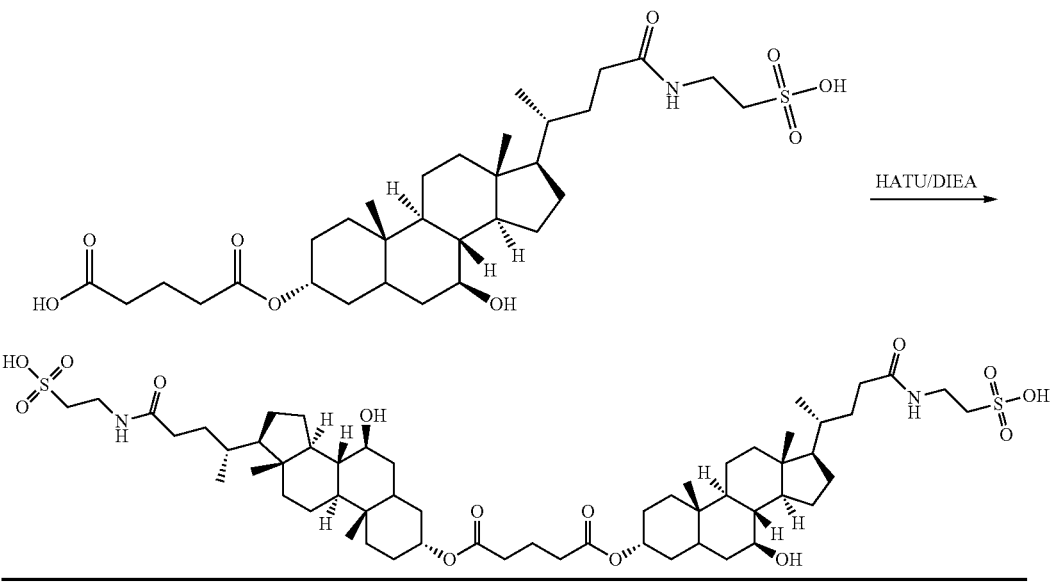

In a 10 mL, one-necked, round-bottomed flask, 2-((4R)-4-((3R,7S,8R,9S,10S,13R,14S,17R)-3,7-dihydroxy-10,13-dimethylhexadecahydro-1H-cyclopenta [α] phenanthren-17-yl) pentanamido) ethanesulfonic acid (TUDCA) (50.0 mg, 0.1 mmol, 2.0 equiv) was dissolved in DMF (1 mL) at room temperature. Then glutaric acid (6.6 mg, 0.05 mmol, 1.0 equiv), N,N-Diisopropylethylamine (DIEA) (25.8 mg, 0.2 mmol, 4.0 equiv), 4-Dimethylaminopyridine (DMAP) (6.1 mg, 0.05 mmol, 1.0 equiv) and 1-Ethyl-3-(3-dimethylaminopropyl)carbodiimide (EDC) (23.0 mg, 0.12 mmol, 2.4 equiv) was added. After the addition was complete, the mixture was stirred at room temperature for 14 h. The mixture was concentrated and used directly.

In a 10 mL, one-necked, round-bottomed flask, the above 5-(((3R,7S,9S,10S,13R,14S,17R)-7-hydroxy-10,13-dimethyl-17-((R)-5-oxo-5-((2-sulfoethyl)amino)pentan-2-yl) hexadecahydro-1H-cyclopenta[α]phenanthren-3-yl)oxy)-5-oxopentanoic acid (30.6 mg, 0.05 mmol, 1.0 equiv) was dissolved in DMF (1 mL) at room temperature. Then 2-((4R)-4-((3R,7S,8R,9S,10S,13R,14S,17R)-3,7-dihydroxy-10,13-dimethylhexadecahydro-1H-cyclopenta [α] phen-anthren-17-yl)pentanamido) ethanesulfonic acid (25.0 mg, 0.05 mmol, 1.0 equiv), 1-[Bis(dimethylamino)methylene]-1H-1,2,3-triazolo[4,5-b]pyridinium 3-oxid hexafluorophosphate (HATU) (19.0 mg, 0.05 mmol, 1.0 equiv) and N,N-Diisopropylethylamine (DIEA) (25.8 mg, 0.2 mmol, 4.0 equiv) were added. After the addition was complete, the mixture was stirred at room temperature for 14 h. The mixture was concentrated and purified by pre-HPLC to get target product as a white solid (9.3 mg), which was confirmed by NMR and Mass spectrum.

The examples of Table L were obtained in analogy to Table K.

Examples

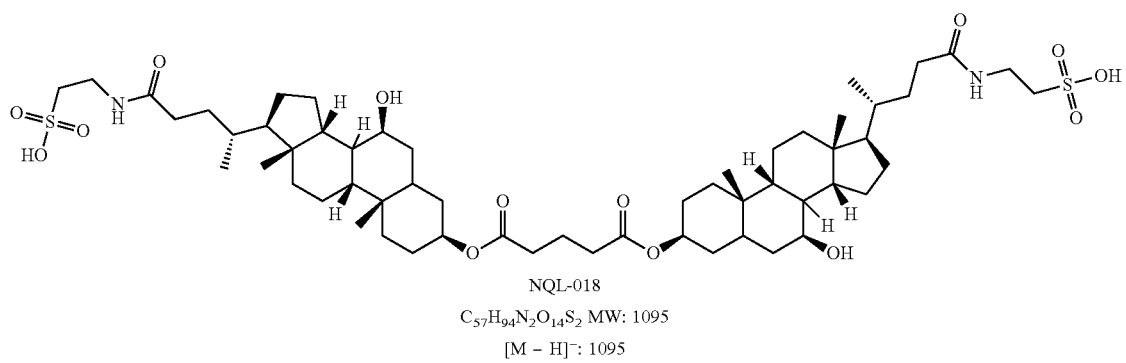

NQL-018
$C_{57}H_{94}N_2O_{14}S_2$ MW: 1095
$[M - H]^-$: 1095

-continued
Examples
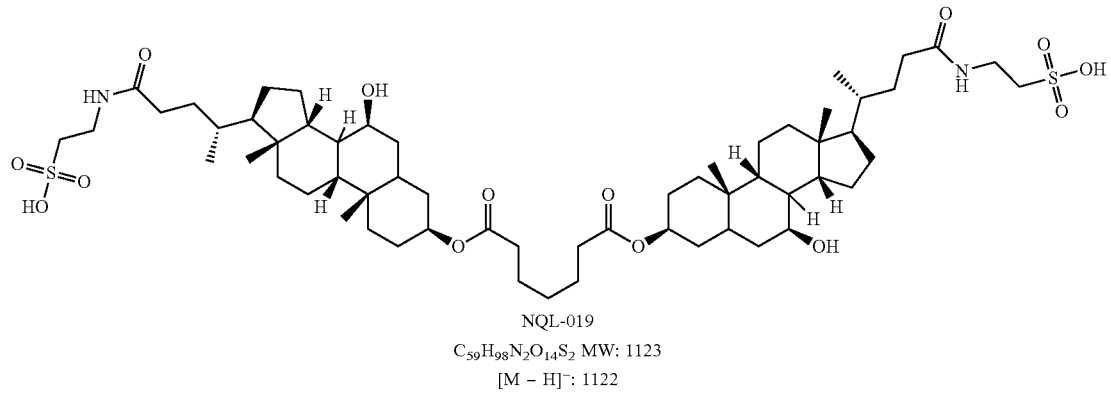
NQL-019
C$_{59}$H$_{98}$N$_2$O$_{14}$S$_2$ MW: 1123
[M − H]$^-$: 1122
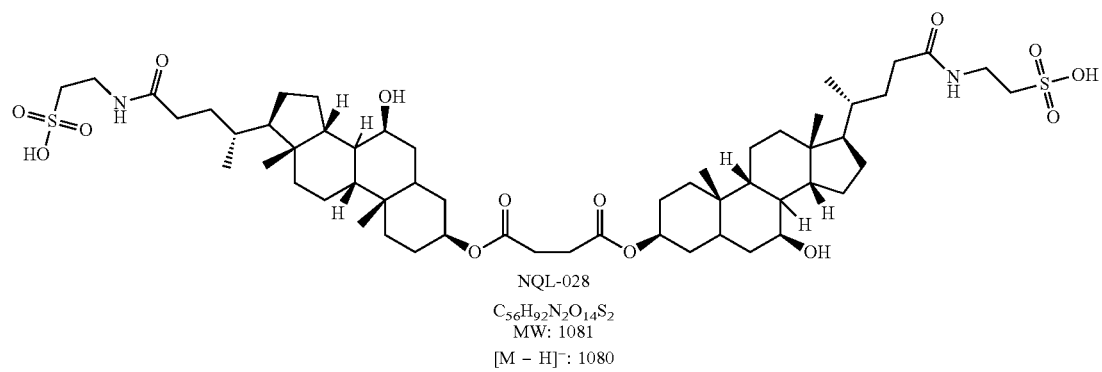
NQL-028
C$_{56}$H$_{92}$N$_2$O$_{14}$S$_2$
MW: 1081
[M − H]$^-$: 1080
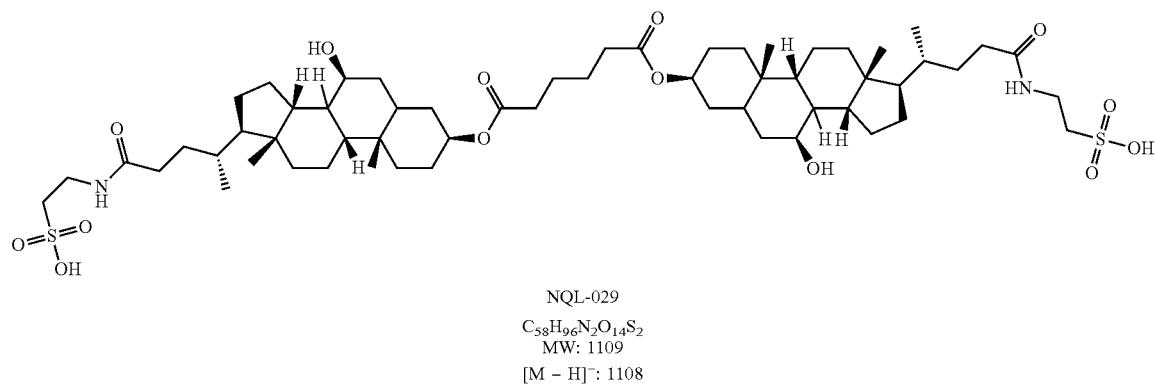
NQL-029
C$_{58}$H$_{96}$N$_2$O$_{14}$S$_2$
MW: 1109
[M − H]$^-$: 1108
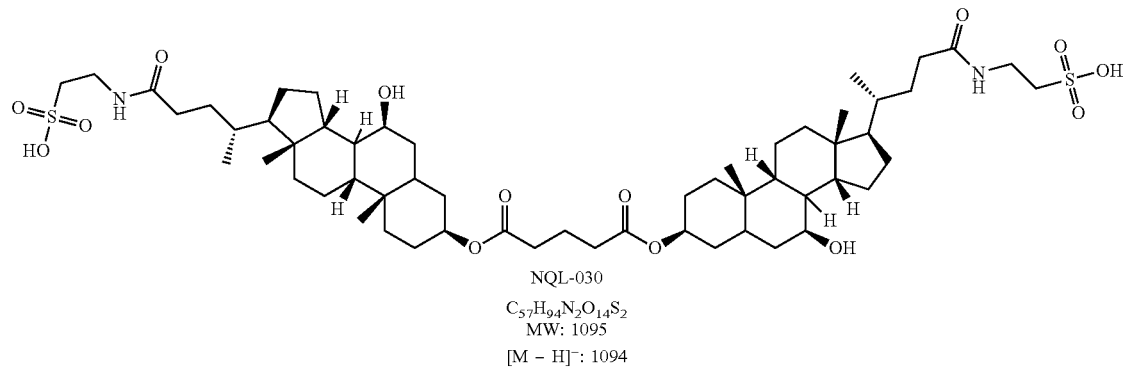
NQL-030
C$_{57}$H$_{94}$N$_2$O$_{14}$S$_2$
MW: 1095
[M − H]$^-$: 1094

Examples

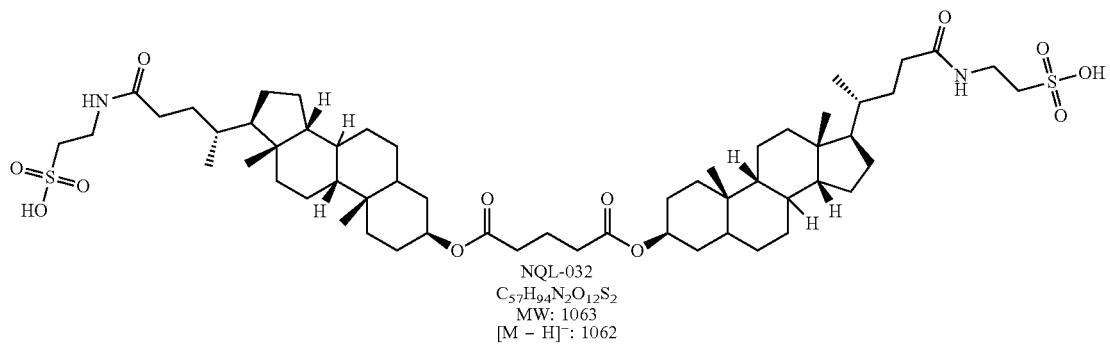

NQL-032
$C_{57}H_{94}N_2O_{12}S_2$
MW: 1063
$[M - H]^-$: 1062

TABLE M

The synthetic route to NQL-044

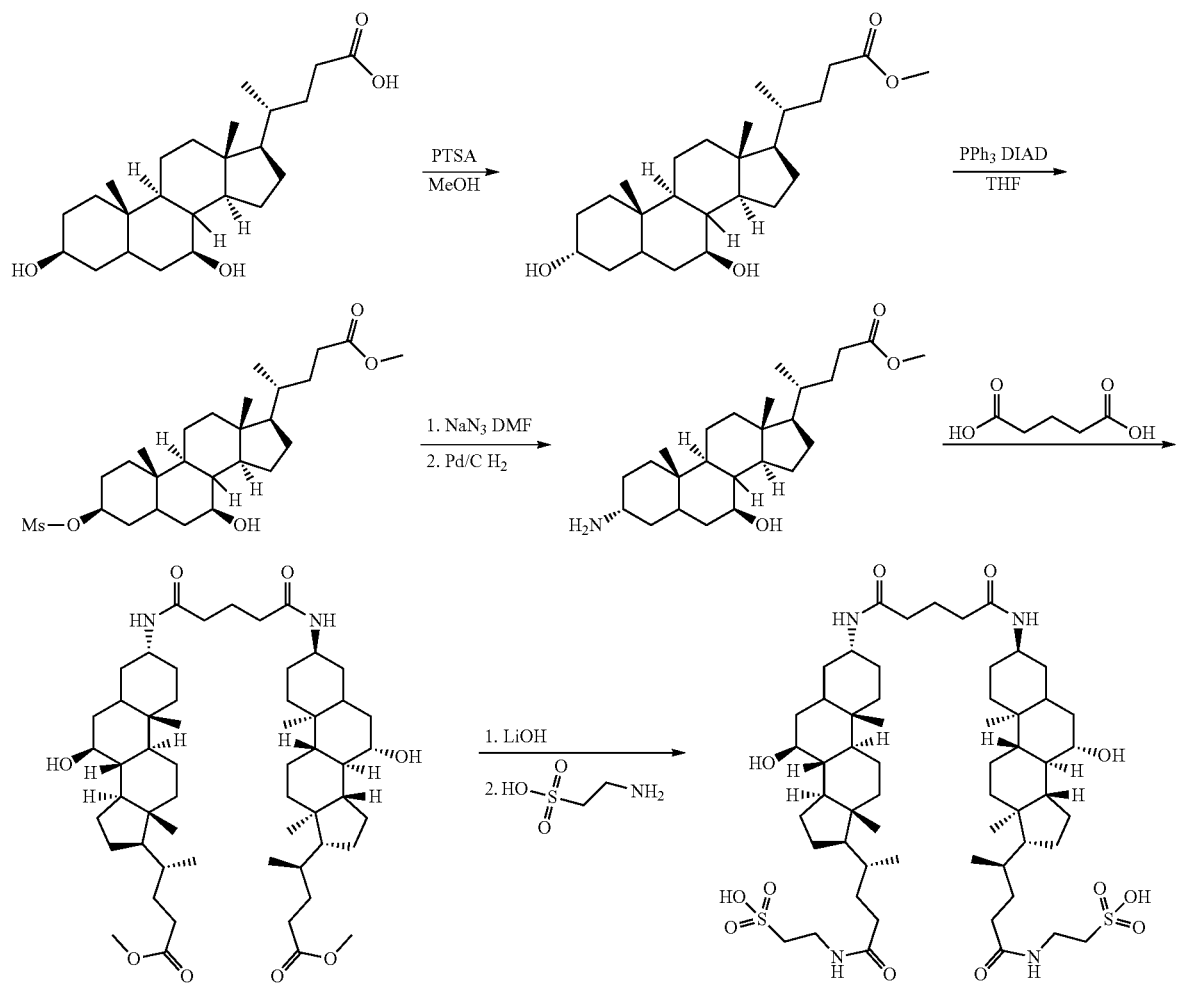

In a 100 mL, one-necked, round-bottom flask, (4R)-4-((3R,7S,9S,10S,13R,14S,17R)-3,7-dihydroxy-10,13-dimethylhexadecahydro-1H-cyclopenta [α] phenanthren-17-yl) pentanoic acid (10.0 g, 25.5 mmol, 1.0 equiv) was dissolved in MeOH (100 mL) at room temperature. Then PTSA (cat.) was added. After the addition was complete, the mixture was stirred at 80° C. for 14 h. The mixture was concentrated and basified with con.NaHCO₃ to pH>8, then extracted with EA, concentrated under reduced pressure to get target product (9.3 g) which was confirmed by NMR.

In a 100 mL, three-necked, round-bottom flask, PPh3 (2.6 g, 10.0 mmol, 2.0 equiv) was dissolved in anhydrous THF (100 mL) at −150 C, then DIAD (2.02 g, 10 mmol, 2.0 equiv) was added under Ar dropwise. After 10 min, methyl (4R)-4-((3R,7S,9S,10S,13R,14S,17R)-3,7-dihydroxy-10,13-dimethylhexadecahydro-1H-cyclopenta [α] phenanthren-17-yl) pentanoate (2.0 g, 5.0 mmol, 1.0 equiv) dissolved in THF (10 mL) was added dropwise. The mixture was stirred at room temperature for 30 min. Then methanesulfonic acid (960 mg, 10.0 mmol, 2.0 equiv) was added. After the addition was complete, the mixture was stirred at room temperature for 14 h. The mixture was quenched by the addition of con.NaHCO₃ to pH>8 and extracted with EA, concentrated under reduced pressure and purified by silica column chromatography (PE:EA=1:1) to get target product (0.6 g) which was confirmed by NMR.

In a 25 mL, one-necked, round-bottom flask, methyl (4R)-4-((3S,7S,9S,10S,13R,14S,17R)-7-hydroxy-10,13-dimethyl-3-((methylsulfonyl)oxy)hexadecahydro-1H-cyclopenta [α] phenanthren-17-yl) pentanoate (1.2 g, 2.5 mmol, 1.0 equiv) was dissolved in DMF (10 mL) at room temperature. Then NaN3 (325 mg, 5.0 mmol, 2.0 equiv) was added. After the addition was complete, the mixture was stirred at 80° C. for 1.5 h. The mixture was washed with water and extracted with EA, concentrated and used directly.

The crude product was dissolved in MeOH (10 mL) at room temperature. Then Pd/C (0.5 g) was added and bubbled with a balloon full of H2. After the addition was complete, the mixture was stirred at room temperature for 14 h under H2. The mixture was concentrated and purified by chromatography column (DCM:MeOH=5:1) to get target product as a yellow solid (700 mg), which was confirmed by NMR and UPLC/MS.

In a 10 mL, one-necked, round-bottom flask, methyl (4R)-4-((3R,7S,9S,10S,13R,14S,17R)-3-amino-7-hydroxy-10,13-dimethylhexadecahydro-1H-cyclopenta [α] phenanthren-17-yl) pentanoate (120.0 mg, 0.3 mmol, 1.0 equiv) was dissolved in DMF (2.0 mL) at room temperature. Then 2-glutaric acid (39.6 mg, 0.3 mmol, 1.0 equiv), DIEA (116.0 mg, 0.9 mmol, 3.0 equiv), DMAP (36 mg, 0.3 mmol, 1.0 equiv) and EDC (173 mg, 0.9 mmol, 3.0 equiv) was added. After the addition was complete, the mixture was stirred at room temperature for 24 h. The mixture was confirmed by UPLC, concentrated and purified by chromatography column (DCM:MeOH=20:1) to get target product (52 mg).

In a 10 mL, one-necked, round-bottom flask, methyl (4R)-4-((3S,7R,10S,13R,17R)-7-hydroxy-3-(5-(((3R,7S,10S,13R,17R)-7-hydroxy-17-((R)-5-methoxy-5-oxopentan-2-yl)-10,13-dimethylhexadecahydro-1H-cyclopenta [α] phenanthren-3-yl)amino)-5-oxopentanamido)-10,13-dimethylhexadecahydro-1H-cyclopenta [α] phenanthren-17-yl) pentanoate (52.0 mg, 0.057 mmol, 1.0 equiv) was dissolved in THF (1.0 mL)/MeOH (0.2 mL)/H2O (1.0 mL) at room temperature. Then LiOH (7.2 mg, 0.17 mmol, 3.0 equiv) was added and stirred at room temperature for 4 h. The mixture was acidified with 1N HCl to pH<3 and extracted with EA, concentrated and used directly.

The crude product was dissolved in DMF (1.5 mL) at room temperature. Then 2-aminoethanesulfonic acid (42.5 mg, 0.34 mmol, 6.0 equiv), DIEA (58.8 mg, 0.46 mmol, 8.0 equiv), DMAP (7 mg, 0.05 mmol, 1.0 equiv) and EDC (32.6 mg, 0.17 mmol, 3.0 equiv) was added. After the addition was complete, the mixture was stirred at room temperature for 14 h. The mixture was concentrated and purified by pre-HPLC to get target product as a white solid (0.7 mg), which was confirmed by NMR and Mass spectrum.

The examples of Table N were obtained in analogy to Table M

Examples

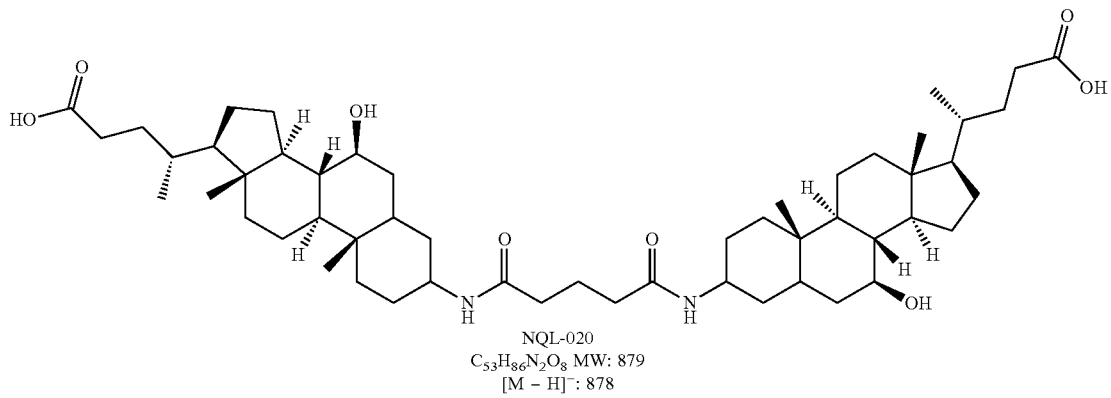

NQL-020
$C_{53}H_{86}N_2O_8$ MW: 879
[M − H]⁻: 878

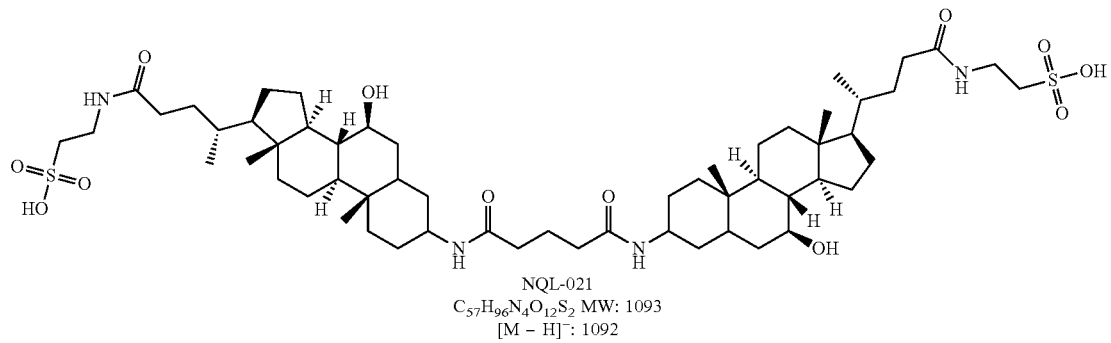

NQL-021
$C_{57}H_{96}N_4O_{12}S_2$ MW: 1093
[M − H]⁻: 1092

-continued
Examples
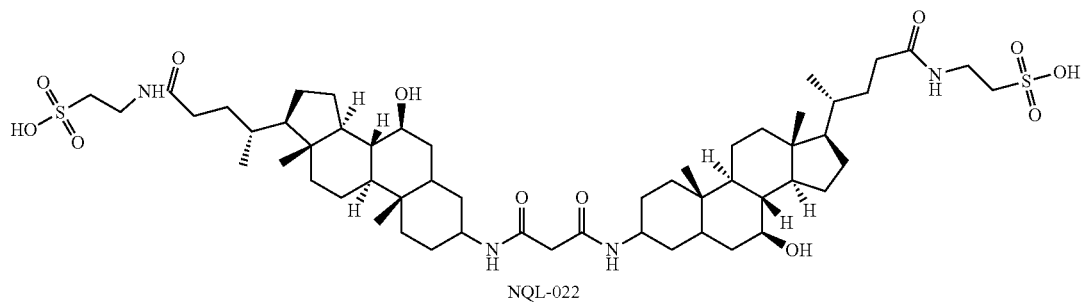
NQL-022
$C_{55}H_{92}N_4O_{12}S_2$ MW: 1065
[M − H]⁻: 1064
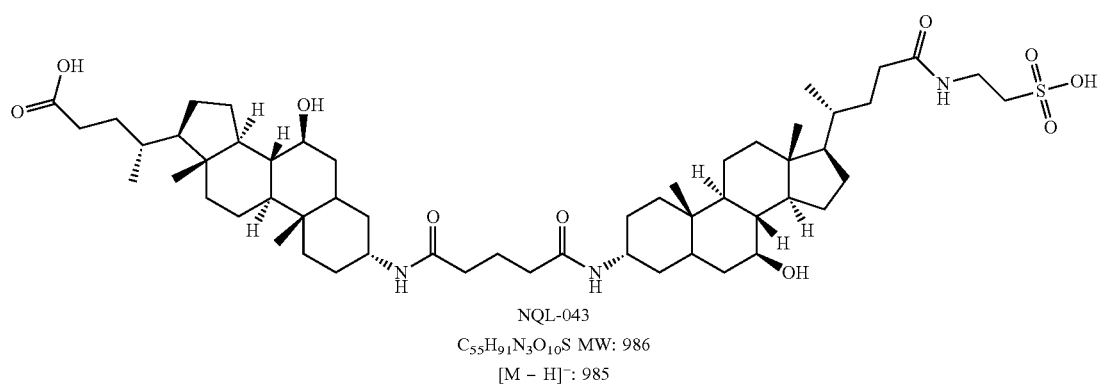
NQL-043
$C_{55}H_{91}N_3O_{10}S$ MW: 986
[M − H]⁻: 985
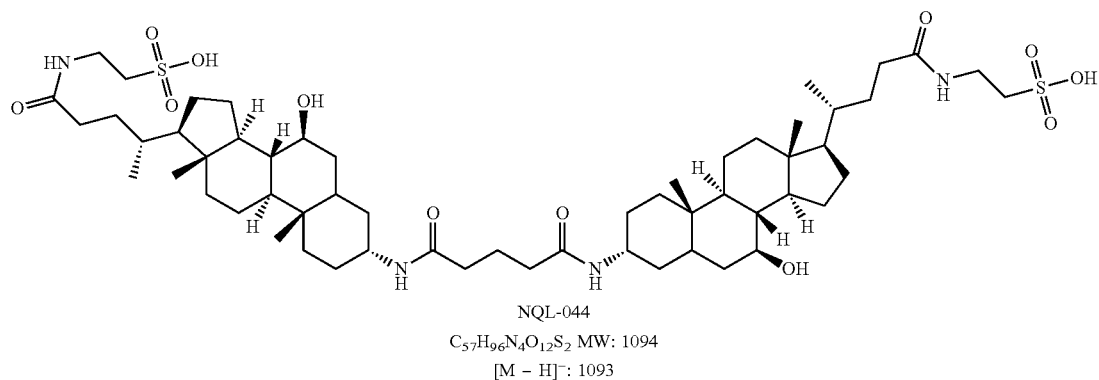
NQL-044
$C_{57}H_{96}N_4O_{12}S_2$ MW: 1094
[M − H]⁻: 1093
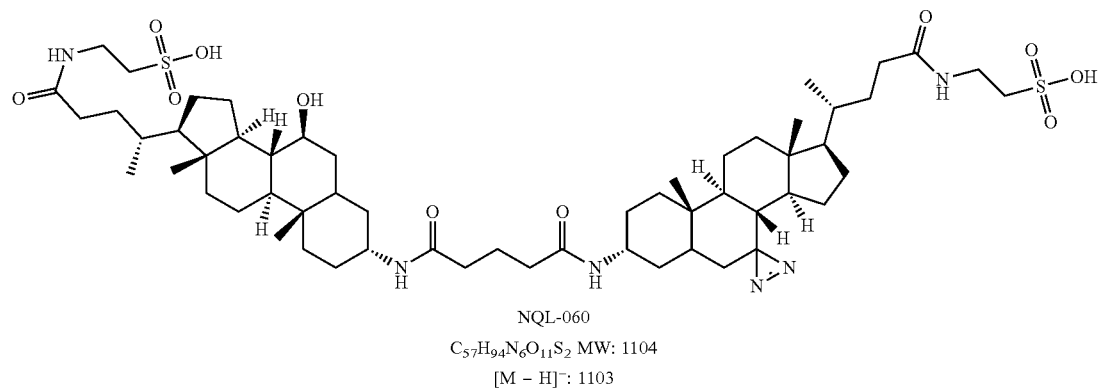
NQL-060
$C_{57}H_{94}N_6O_{11}S_2$ MW: 1104
[M − H]⁻: 1103

TABLE O
The synthetic route to NQL-055
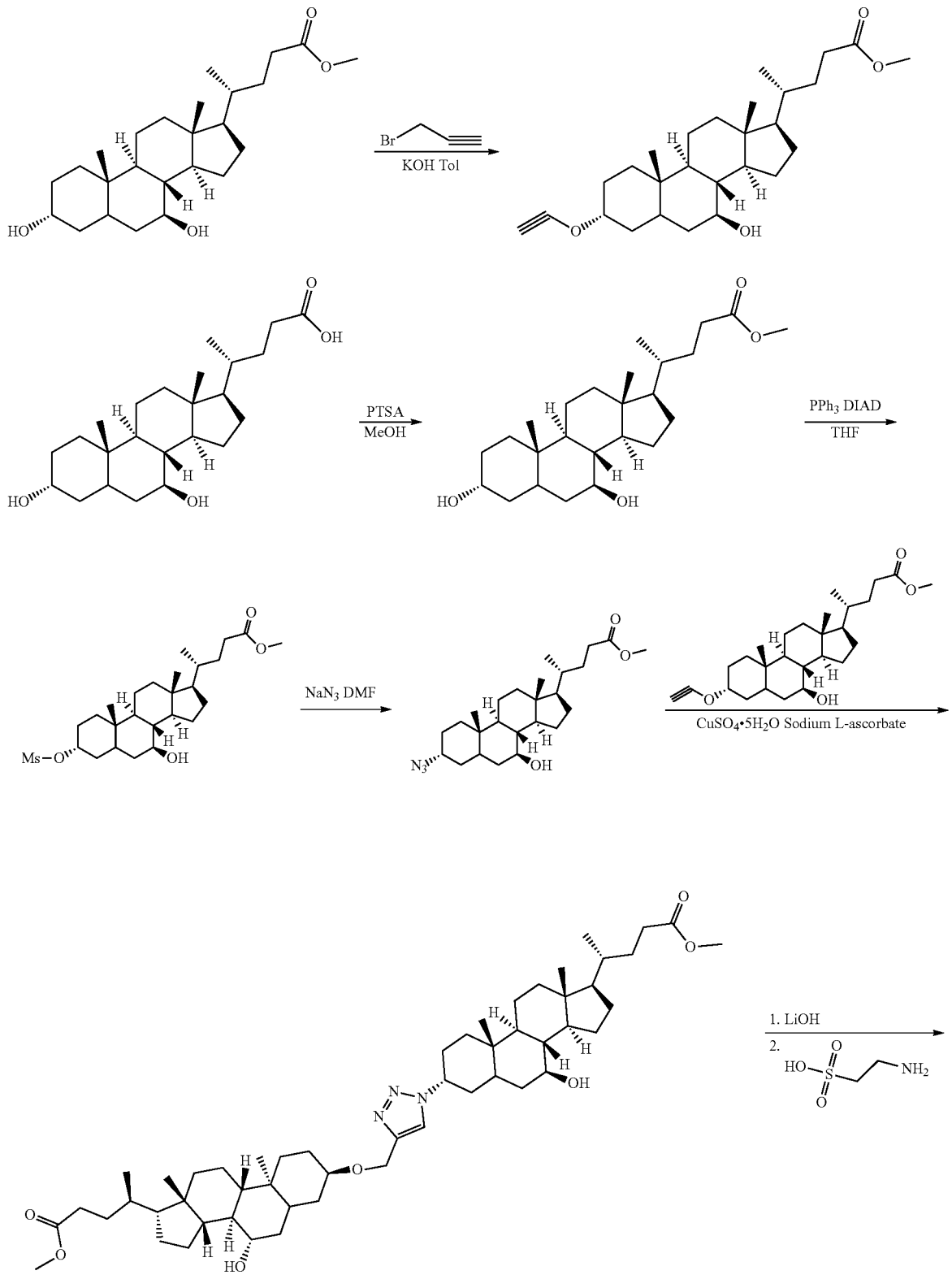

TABLE O-continued

The synthetic route to NQL-055

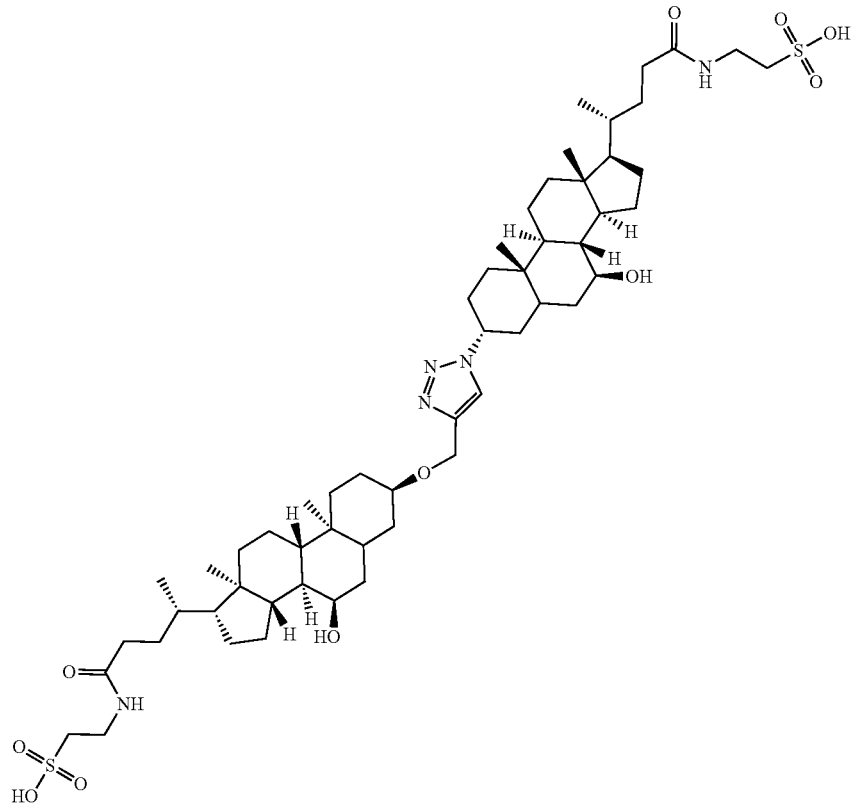 [SMILES: C[C@H](CCC(=O)NCCS(=O)(=O)O)[C@H]1CC[C@H]2[C@@H]3[C@@H](O)CC4C[C@H](n5cc(CO[C@@H]6CC[C@@]7(C)C(C6)C[C@@H](O)[C@H]6[C@@H]8CC[C@H]([C@@H](C)CCC(=O)NCCS(=O)(=O)O)[C@@]8(C)CC[C@@H]67)nn5)CC[C@]4(C)[C@H]3CC[C@]12C]

In a 100 mL, one-necked, round-bottom flask, (4R)-4-((3R,7S,9S,10S,13R,14S,17R)-3,7-dihydroxy-10,13-dimethylhexadecahydro-1H-cyclopenta [α] phenanthren-17-yl) pentanoic acid (406.0 mg, 1.0 mmol, 1.0 equiv) and 3-bromoprop-1-yne (476.0 mg, 4.0 mmol, 4.0 equiv) was dissolved in DMF (2 mL) at room temperature. After the addition was complete, the mixture was stirred at room temperature for 14 h. The mixture was washed with water and extracted with EA, concentrated and purified by chromatography column (DCM:MeOH=20:1) to get target product (50 mg) which was confirmed by NMR.

In a 100 mL, one-necked, round-bottom flask, (4R)-4-((3R,7S,9S,10S,13R,14S,17R)-3,7-dihydroxy-10,13-dimethylhexadecahydro-1H-cyclopenta [α] phenanthren-17-yl) pentanoic acid (10.0 g, 25.5 mmol, 1.0 equiv) was dissolved in MeOH (100 mL) at room temperature. Then PTSA (cat.) was added. After the addition was complete, the mixture was stirred at 80° C. for 14 h. The mixture was concentrated and basified with con.NaHCO₃ to pH>8, then extracted with EA, concentrated under reduced pressure to get target product (9.3 g) which was confirmed by NMR.

In a 100 mL, three-necked, round-bottom flask, PPh₃ (2.6 g, 10.0 mmol, 2.0 equiv) was dissolved in anhydrous THF (100 mL) at −15° C., then DIAD (2.02 g, 10 mmol, 2.0 equiv) was added under Ar dropwise. After 10 min, methyl (4R)-4-((3R,7S,9S,10S,13R,14S,17R)-3,7-dihydroxy-10,13-dimethylhexadecahydro-1H-cyclopenta [α] phenanthren-17-yl) pentanoate (2.0 g, 5.0 mmol, 1.0 equiv) dissolved in THF (10 mL) was added dropwise. The mixture was stirred at room temperature for 30 min. Then methanesulfonic acid (960 mg, 10.0 mmol, 2.0 equiv) was added.

After the addition was complete, the mixture was stirred at room temperature for 14 h. The mixture was quenched by the addition of con.NaHCO₃ to pH>8 and extracted with EA, concentrated under reduced pressure and purified by silica column chromatography (PE:EA=1:1) to get target product (0.6 g) which was confirmed by NMR.

In a 25 mL, one-necked, round-bottom flask, methyl (4R)-4-((3S,7S,9S,10S,13R,14S,17R)-7-hydroxy-10,13-dimethyl-3-((methylsulfonyl)oxy)hexadecahydro-1H-cyclopenta [α] phenanthren-17-yl) pentanoate (1.2 g, 2.5 mmol, 1.0 equiv) was dissolved in DMF (10 mL) at room temperature. Then NaN₃ (325 mg, 5.0 mmol, 2.0 equiv) was added. After the addition was complete, the mixture was stirred at 80° C. for 1.5 h. The mixture was washed with water and extracted with EA, concentrated purified by chromatography column (PE:EA=5:1) to get target product as a yellow solid (700 mg), which was confirmed by NMR.

In a 10 mL, one-necked, round-bottom flask, methyl (4R)-4-((3R,7S,9S,10S,13R,14S,17R)-3-azido-7-hydroxy-10,13-dimethylhexadecahydro-1H-cyclopenta [α] phenanthren-17-yl) pentanoate (35.5 mg, 0.084 mmol, 1.5 equiv) and methyl (4R)-4-((3R,7S,9S,10S,13R,14S,17R)-3-(ethynyloxy)-7-hydroxy-10,13-dimethylhexadecahydro-1H-cyclopenta [α] phenanthren-17-yl) pentanoate (25.0 mg, 0.056 mmol, 1.0 equiv) was dissolved in DMF (2.0 mL) at room temperature. Then CuSO₄·5H₂O (15.12 mg, 0.056 mmol, 1.0 equiv) and Sodium L-ascorbate (22.0 mg, 0.112 mmol, 2.0 equiv) in H₂O (2.0 mL) was added. After the addition was complete, the mixture was stirred at room temperature for 24 h. The mixture was washed with water and extracted with DCM, concentrated and purified by chromatography column (DCM:MeOH=20:1) to get target product (20 mg).

In a 10 mL, one-necked, round-bottom flask, methyl (4S)-4-((3S,7R,9R,10R,13S,14R,17S)-7-hydroxy-3-((1-((3R,7S,9S,10S,13R,14S,17R)-7-hydroxy-17-((R)-5-methoxy-5-oxopentan-2-yl)-10,13-dimethylhexadecahydro-1H-cyclopenta [a]phenanthren-3-yl)-1H-1,2,3-triazol-4-yl)methoxy)-10,13-dimethylhexadecahydro-1H-cyclopenta [a]phenanthren-17-yl) pentanoate (20.0 mg, 0.023 mmol, 1.0 equiv) was dissolved in THF (1.0 mL)/MeOH (0.2 mL)/H₂O (1.0 mL) at room temperature. Then LiOH (4.2 mg, 0.114 mmol, 5.0 equiv) was added and stirred at room temperature for 4 h. The mixture was acidified with 1N HCl to pH<3 and extracted with EA, concentrated and used directly.

The crude product was dissolved in DMF (1.5 mL) at room temperature. Then 2-aminoethanesulfonic acid (17.8 mg, 0.142 mmol, 6.0 equiv), DIEA (24.7 mg, 0.192 mmol, 8.0 equiv), DMAP (3 mg, 0.024 mmol, 1.0 equiv) and EDC (13.6 mg, 0.71 mmol, 3.0 equiv) was added. After the addition was complete, the mixture was stirred at room temperature for 14 h. The mixture was concentrated and purified by pre-HPLC to get target product as a white solid (4.4 mg), which was confirmed by NMR.

The examples of Table P were obtained in analogy to Table O.

| Examples |
|---|
| 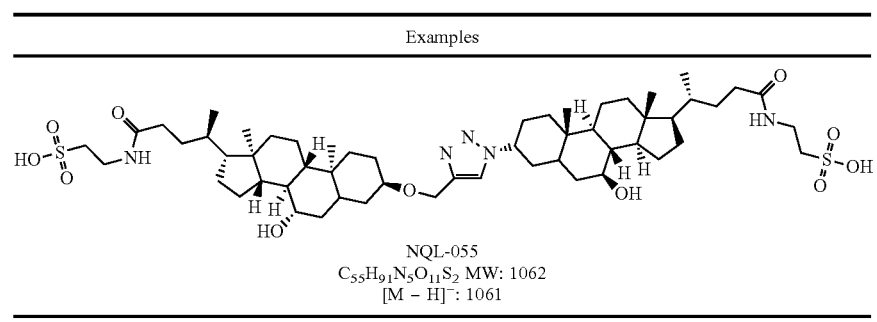<br>NQL-055<br>C₅₅H₉₁N₅O₁₁S₂ MW: 1062<br>[M − H]⁻: 1061 |

TABLE Q

The synthetic route to NQL-052

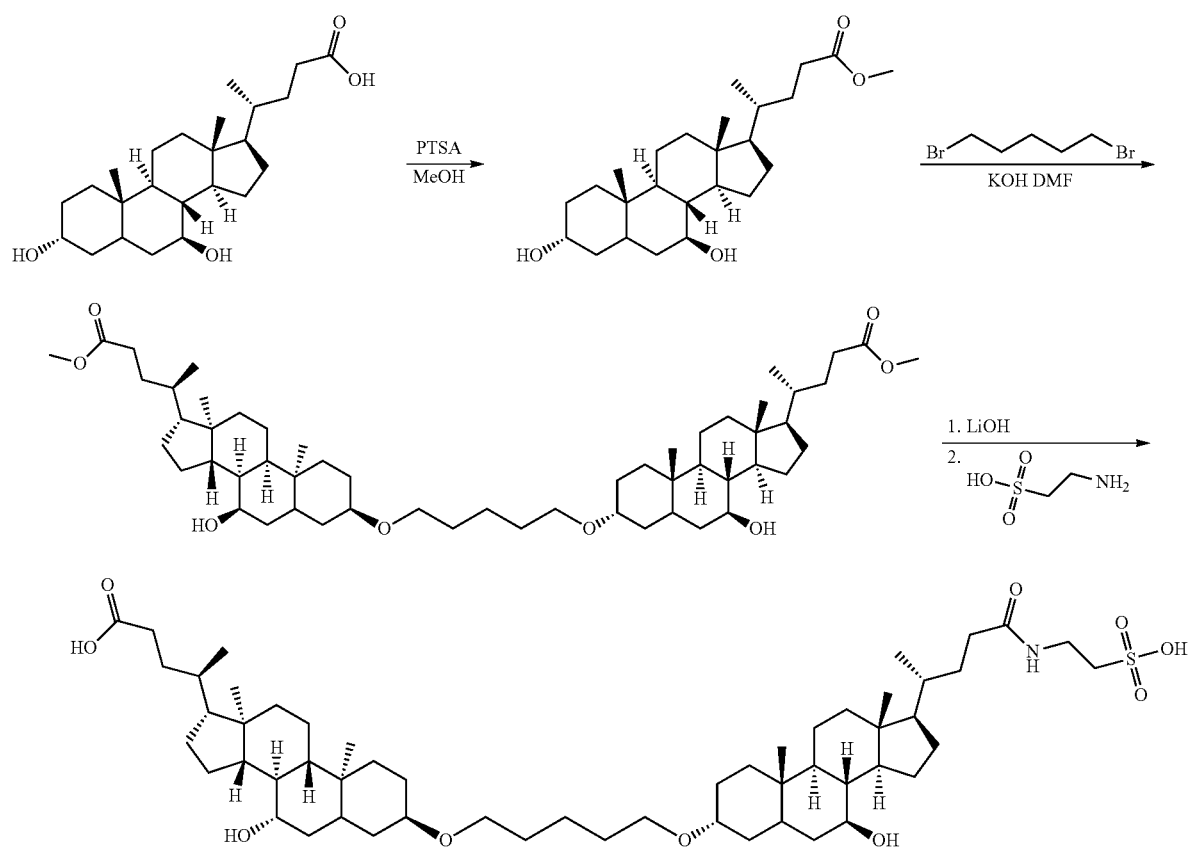

In a 100 mL, one-necked, round-bottom flask, (4R)-4-((3R,7S,9S,10S,13R,14S,17R)-3,7-dihydroxy-10,13-dimethylhexadecahydro-1H-cyclopenta [α] phenanthren-17-yl) pentanoic acid (10.0 g, 25.5 mmol, 1.0 equiv) was dissolved in MeOH (100 mL) at room temperature. Then PTSA (cat.) was added. After the addition was complete, the mixture was stirred at 80° C. for 14 h. The mixture was concentrated and basified with con.NaHCO₃ to pH>8, then extracted with EA, concentrated under reduced pressure to get target product (9.3 g) which was confirmed by NMR and MS spectrum.

In a 25 mL, one-necked, round-bottom flask, methyl methyl (4R)-4-((3R,7S,9S,10S,13R,14S,17R)-3,7-dihydroxy-10,13-dimethylhexadecahydro-1H-cyclopenta[a]phenanthren-17-yl) pentanoate (203.0 mg, 0.5 mmol, 1.0 equiv) was dissolved in DMF (10 mL) at room temperature. Then 1,5-dibromopentane (111.5 mg, 0.5 mmol, 1.0 equiv) and KOH (56.0 mg, 1.0 mmol, 2.0 equiv) was added. After the addition was complete, the mixture was stirred at room temperature for 36 h. The mixture was washed with water and extracted with EA, concentrated to get a crude product which was used directly.

In a 10 mL, one-necked, round-bottom flask, dimethyl 4,4'-((3R,3'R,7S,7'S,10S,10'S,13R,13'R,17R,17'R)-(pentane-1,5-diylbis (oxy)) bis (7-hydroxy-10,13-dimethylhexadecahydro-1H-cyclopenta [a] phenanthrene-3,17-diyl)) (4R,4'R)-dipentanoate (crude) was dissolved in THF (1.0 mL)/MeOH (0.2 mL)/H2O (1.0 mL) at room temperature. Then LiOH (7.2 mg, 0.17 mmol, 3.0 equiv) was added and stirred at room temperature for 4 h. The mixture was acidified with 1N HCl to pH<3 and extracted with EA, concentrated purified by chromatography column (DCM:MeOH=20:1) to get target product (47 mg) which was confirmed by UPLC/MS.

The product was dissolved in DMF (1.5 mL) at room temperature. Then 2-aminoethanesulfonic acid (42.5 mg, 0.34 mmol, 6.0 equiv), DIEA (58.8 mg, 0.46 mmol, 8.0 equiv), DMAP (7 mg, 0.05 mmol, 1.0 equiv) and EDC (32.6 mg, 0.17 mmol, 3.0 equiv) was added. After the addition was complete, the mixture was stirred at room temperature for 14 h. The mixture was concentrated and purified by pre-HPLC to get target product as a white solid (2.6 mg), which was confirmed by NMR and UPLC/MS.

The examples of Table R were obtained in analogy to Table Q

Examples

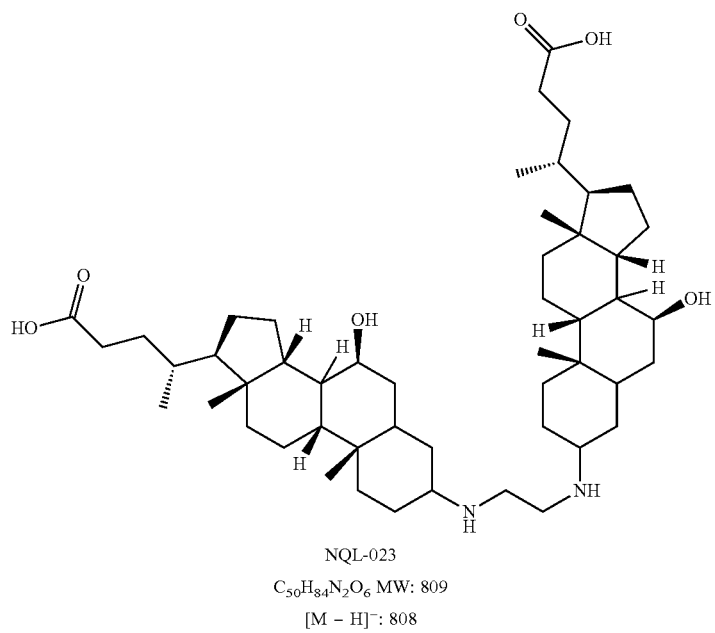

NQL-023
$C_{50}H_{84}N_2O_6$ MW: 809
$[M - H]^-$: 808

-continued
Examples
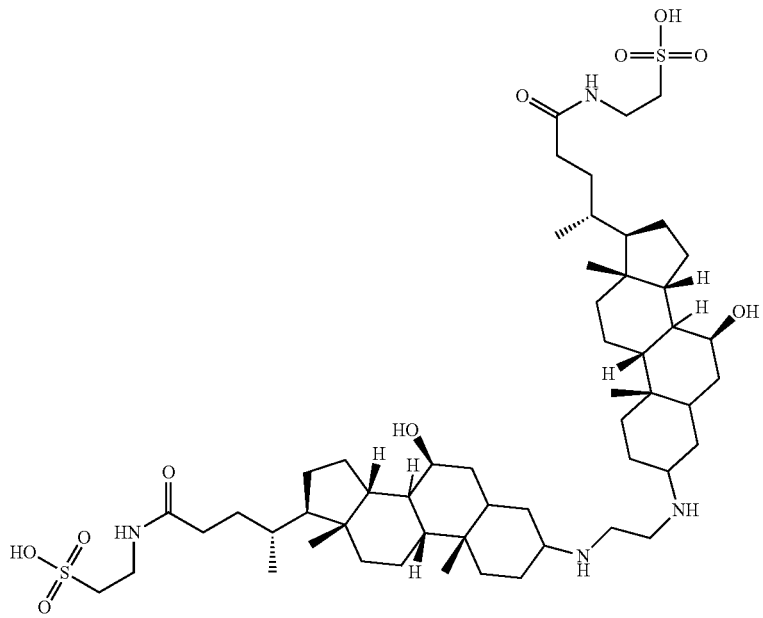 [SMILES: C[C@H](CCC(=O)NCCS(=O)(=O)O)[C@H]1CC[C@@H]2C3[C@@H](CC[C@@]21C)[C@@]1(C)CCC(NCCNC2CC[C@@]4(C)C(C2)C[C@H](O)C2[C@H]5CC[C@H]([C@H](C)CCC(=O)NCCS(=O)(=O)O)[C@@]5(C)CC[C@H]24)CC1C[C@@H]3O]
NQL-024
$C_{54}H_{94}N_4O_{10}S_2$ MW: 1023
$[M - H]^-$: 1022
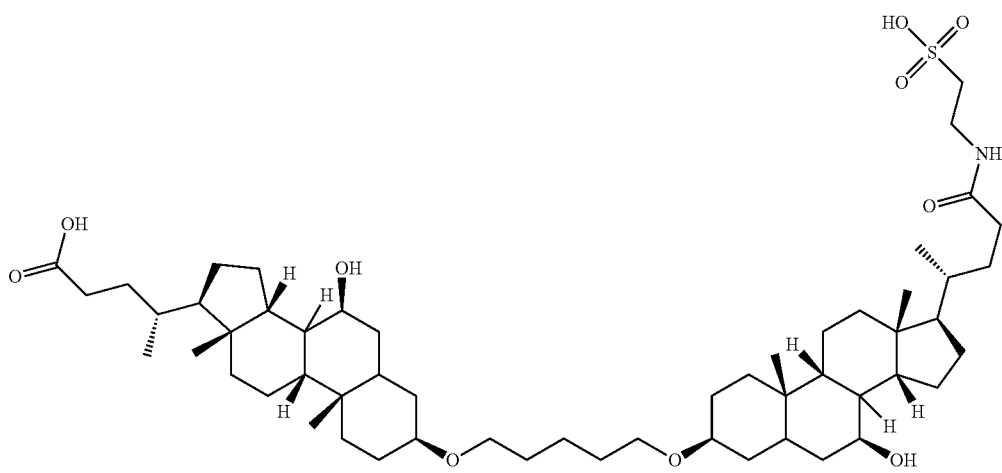 [SMILES: C[C@H](CCC(=O)O)[C@H]1CC[C@@H]2C3[C@@H](CC[C@@]21C)[C@@]1(C)CC[C@H](OCCCCCO[C@H]2CC[C@@]4(C)C(C2)C[C@H](O)C2[C@H]5CC[C@H]([C@H](C)CCC(=O)NCCS(=O)(=O)O)[C@@]5(C)CC[C@H]24)CC1C[C@@H]3O]
NQL-052
$C_{55}H_{93}NO_{10}S$ MW: 960
$[M - H]^-$: 959

-continued
Examples
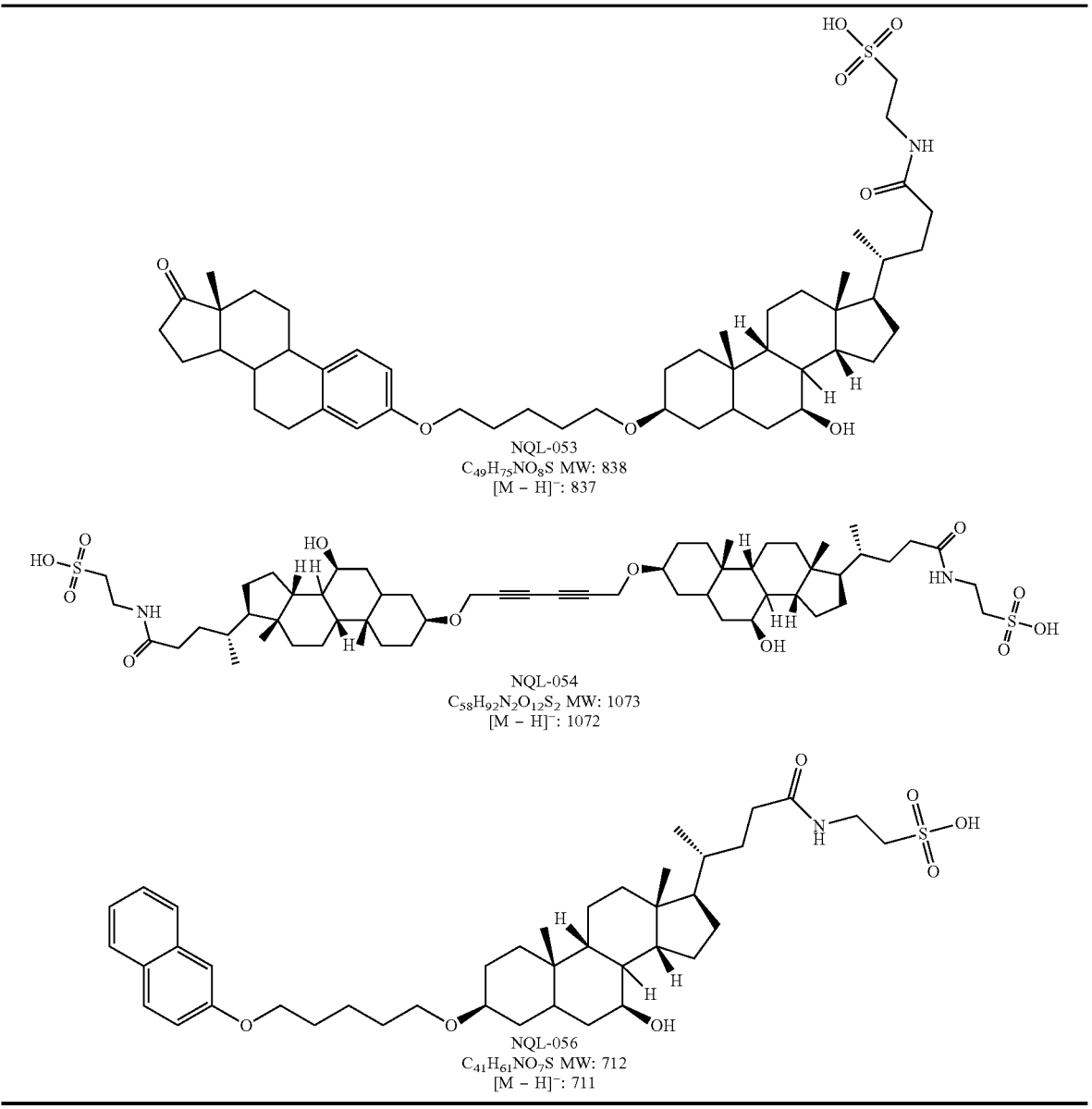
TABLE S
The synthetic route to NQL-052
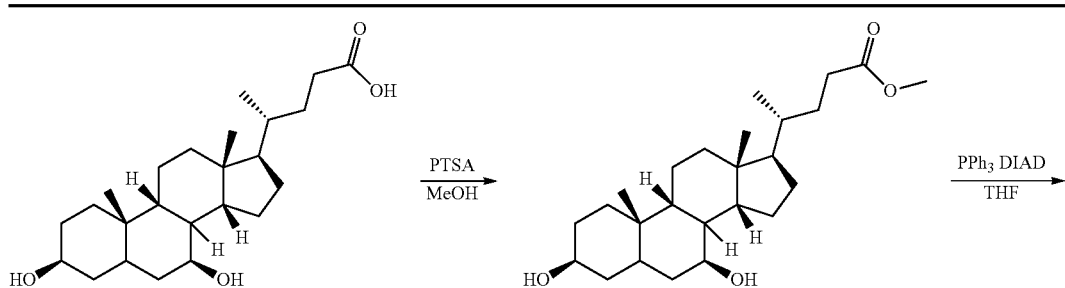

TABLE S-continued

The synthetic route to NQL-052

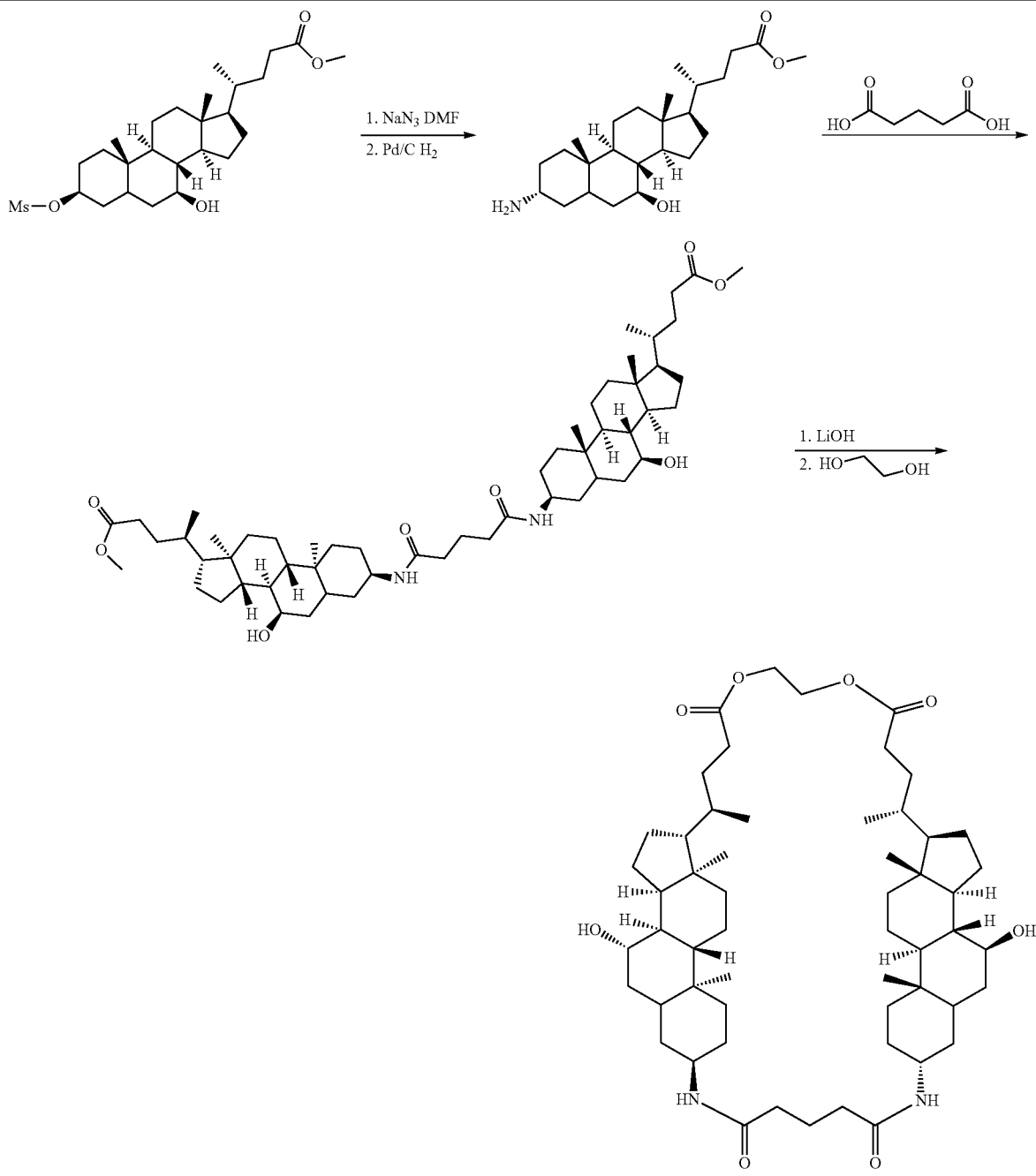

In a 100 mL, one-necked, round-bottom flask, (4R)-4-((3R,7S,9S,10S,13R,14S,17R)-3,7-dihydroxy-10,13-dimethylhexadecahydro-1H-cyclopenta [α] phenanthren-1'7-yl) pentanoic acid (10.0 g, 25.5 mmol, 1.0 equiv) was dissolved in MeOH (100 mL) at room temperature. Then PTSA (cat.) was added. After the addition was complete, the mixture was stirred at 80° C. for 14 h. The mixture was concentrated and basified with con.NaHCO₃ to pH>8, then extracted with EA, concentrated under reduced pressure to get target product (9.3 g) which was confirmed by NMR.

In a 100 mL, three-necked, round-bottom flask, PPh₃ (2.6 g, 10.0 mmol, 2.0 equiv) was dissolved in anhydrous THF (100 mL) at −15° C., then DIAD (2.02 g, 10 mmol, 2.0 equiv) was added under Ar dropwise. After 10 min, methyl (4R)-4-((3R,7S,9S,10S,13R,14S,17R)-3,7-dihydroxy-10,13-dimethylhexadecahydro-1H-cyclopenta [α] phenanthren-17-yl) pentanoate (2.0 g, 5.0 mmol, 1.0 equiv) dissolved in THF (10 mL) was added dropwise. The mixture was stirred at room temperature for 30 min. Then methanesulfonic acid (960 mg, 10.0 mmol, 2.0 equiv) was added. After the addition was complete, the mixture was stirred at room temperature for 14 h. The mixture was quenched by the addition of con.NaHCO₃ to pH>8 and extracted with EA, concentrated under reduced pressure and purified by silica column chromatography (PE:EA=1:1) to get target product (0.6 g) which was confirmed by NMR.

In a 25 mL, one-necked, round-bottom flask, methyl (4R)-4-((3S,7S,9S,10S,13R,14S,17R)-7-hydroxy-10,13-dimethyl-3-((methylsulfonyl)oxy)hexadecahydro-1H-cyclopenta [α] phenanthren-17-yl) pentanoate (1.2 g, 2.5 mmol, 1.0 equiv) was dissolved in DMF (10 mL) at room temperature. Then NaN$_3$ (325 mg, 5.0 mmol, 2.0 equiv) was added. After the addition was complete, the mixture was stirred at 80° C. for 1.5 h. The mixture was washed with water and extracted with EA, concentrated and used directly.

The crude product was dissolved in MeOH (10 mL) at room temperature. Then Pd/C (0.5 g) was added and bubbled with a balloon full of H$_2$. After the addition was complete, the mixture was stirred at room temperature for 14 h under H$_2$. The mixture was concentrated and purified by chromatography column (DCM:MeOH=5:1) to get target product as a yellow solid (700 mg), which was confirmed by NMR.

In a 10 mL, one-necked, round-bottom flask, methyl (4R)-4-((3R,7S,9S,10S,13R,14S,17R)-3-amino-7-hydroxy-10,13-dimethylhexadecahydro-1H-cyclopenta [α] phenanthren-17-yl) pentanoate (120.0 mg, 0.3 mmol, 1.0 equiv) was dissolved in DMF (2.0 mL) at room temperature. Then 2-glutaric acid (39.6 mg, 0.3 mmol, 1.0 equiv), DIEA (116.0 mg, 0.9 mmol, 3.0 equiv), DMAP (36 mg, 0.3 mmol, 1.0 equiv) and EDC (173 mg, 0.9 mmol, 3.0 equiv) was added. After the addition was complete, the mixture was stirred at room temperature for 24 h. The mixture was confirmed by UPLC, concentrated and purified by chromatography column (DCM:MeOH=20:1) to get target product (52 mg).

In a 10 mL, one-necked, round-bottom flask, methyl (4R)-4-((3S,7R,10S,13R,17R)-7-hydroxy-3-(5-(((3R,7S, 10S,13R,17R)-7-hydroxy-17-((R)-5-methoxy-5-oxopentan-2-yl)-10,13-dimethylhexadecahydro-1H-cyclopenta [α] phenanthren-3-yl)amino)-5-oxopentanamido)-10,13-dimethylhexadecahydro-1H-cyclopenta [α] phenanthren-17-yl) pentanoate (45.0 mg, 0.05 mmol, 1.0 equiv) was dissolved in THF (1.0 mL)/MeOH (0.2 mL)/H$_2$O (1.0 mL) at room temperature. Then LiOH (7.2 mg, 0.17 mmol, 3.0 equiv) was added and stirred at room temperature for 4 h. The mixture was acidified with 1N HCl to pH<3 and extracted with EA, concentrated and used directly.

The crude product was dissolved in DMF (1.5 mL) at room temperature. Then ethane-1,2-diol (2.2 mg, 0.035 mmol, 0.7 equiv), DIEA (25.8 mg, 0.2 mmol, 4.0 equiv), DMAP (6 mg, 0.05 mmol, 1.0 equiv) and DCC (31.0 mg, 0.15 mmol, 3.0 equiv) was added. After the addition was complete, the mixture was stirred at room temperature for 14 h. The mixture was concentrated and purified by pre-HPLC to get target product as a white solid (3.4 mg), which was confirmed by NMR.

The examples of Table T were obtained in analogy to Table S

Examples

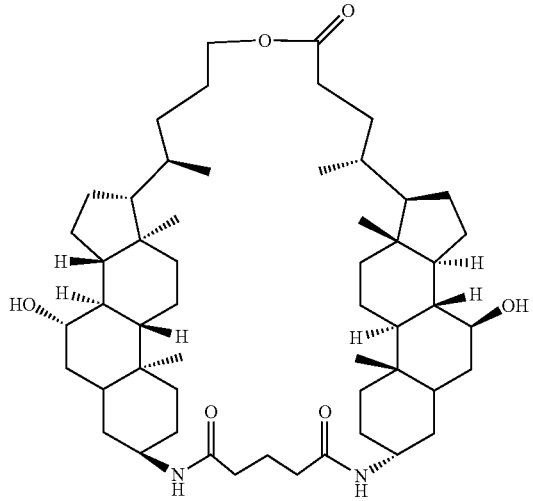 [SMILES: C[C@@H]1CCCOC(=O)CC[C@@H](C)[C@H]2CC[C@H]3[C@@H]4[C@@H](O)CC5C[C@@H](CC[C@]5(C)[C@H]4CC[C@]23C)NC(=O)CCCC(=O)N[C@@H]2CC[C@@]3(C)C(C2)C[C@H](O)[C@H]2[C@@H]4CC[C@H]1[C@@]4(C)CC[C@@H]23]

NQL-058

C$_{53}$H$_{86}$N$_2$O$_6$ MW: 847

[M + H]$^+$: 848

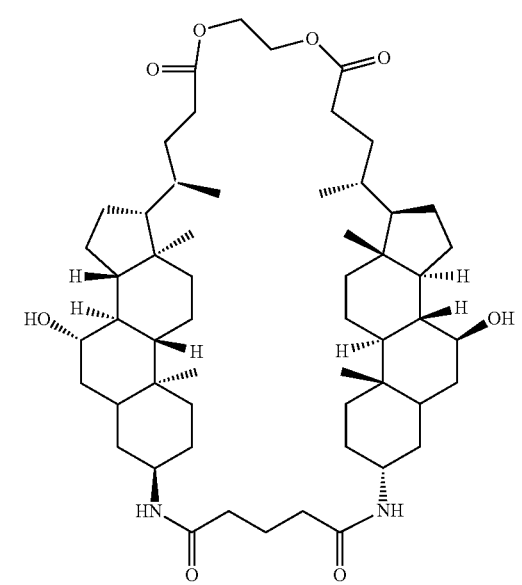

NQL-059

C$_{55}$H$_{88}$N$_2$O$_8$ MW: 905

[M + H]$^+$: 906

The invention claimed is:
1. A compound of the following Formula, a stereoisomer, or a salt thereof:

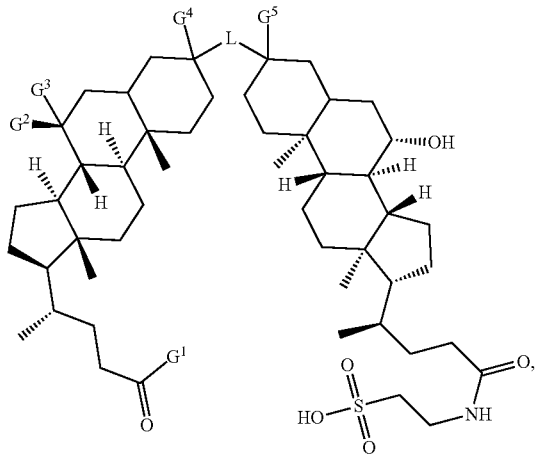

wherein:
G¹ is OH or

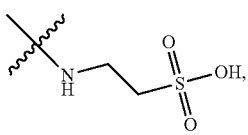 [SMILES: *NCCS(=O)(=O)O]

G² and G³ are independently OH or H, provided that they are not both OH, or G² and G³ together with the carbon they are both attached to form

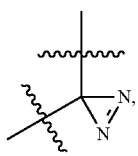 [SMILES: *C1(*)N=N1]

G⁴ and G⁵ are both hydrogen,
or when L is a bond, G⁴ and G⁵ are both OH, both hydrogen, or G⁴ and G⁵ form a bond,
L is

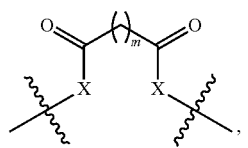

a bond,

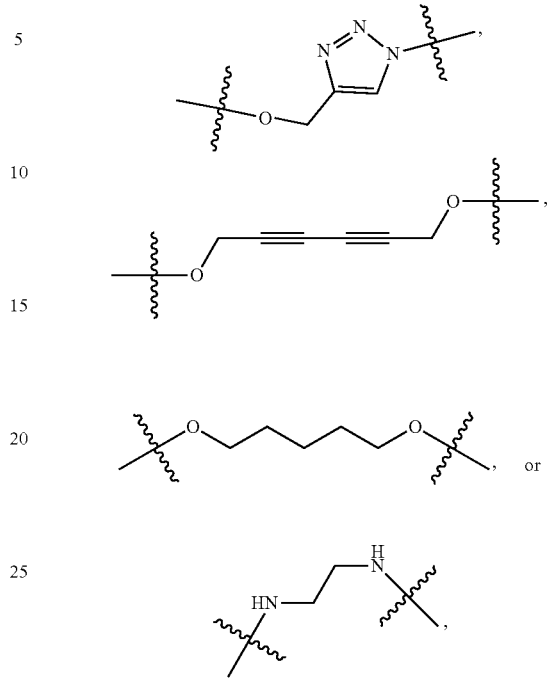

wherein: m is 1-7, X is O or NH.

2. The compound, stereoisomer, or salt of claim 1, wherein L is

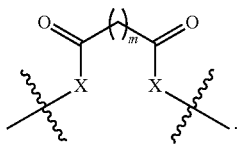

3. The compound, stereoisomer, or salt of claim 2, wherein X is O.
4. The compound, stereoisomer, or salt of claim 3, wherein m is 3.
5. The compound, stereoisomer, or salt of claim 2, wherein X is NH.
6. The compound, stereoisomer, or salt of claim 5, wherein m is 3.
7. The compound, stereoisomer, or salt of claim 2, wherein G¹ is

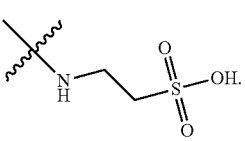

8. The compound, stereoisomer, or salt of claim 2, wherein G² is OH and G³ is H.
9. A compound, or a salt thereof, wherein the compound is selected from:

189 190
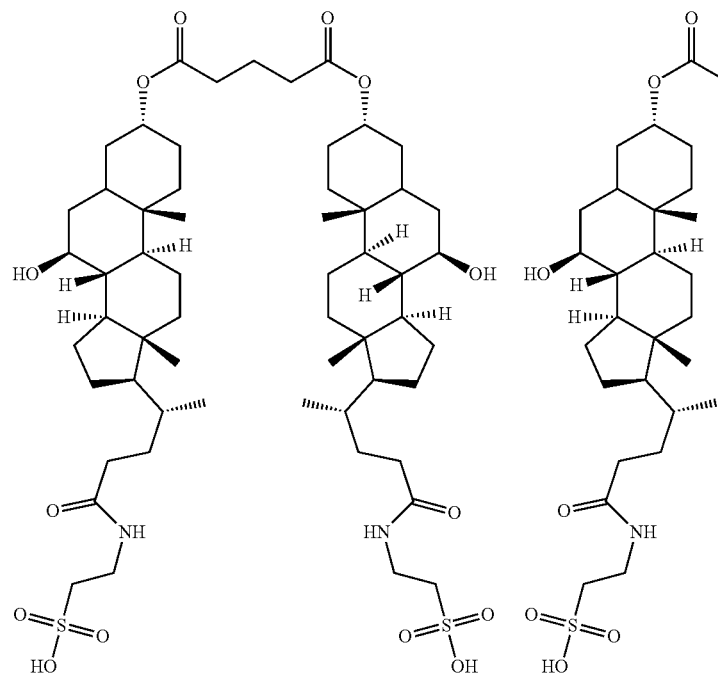
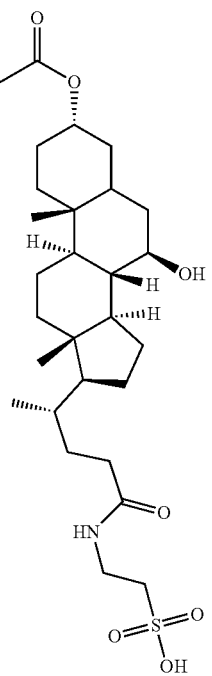
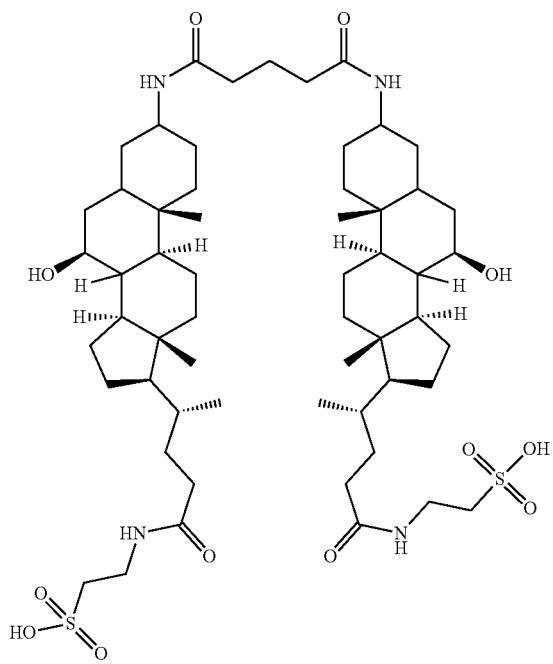

-continued
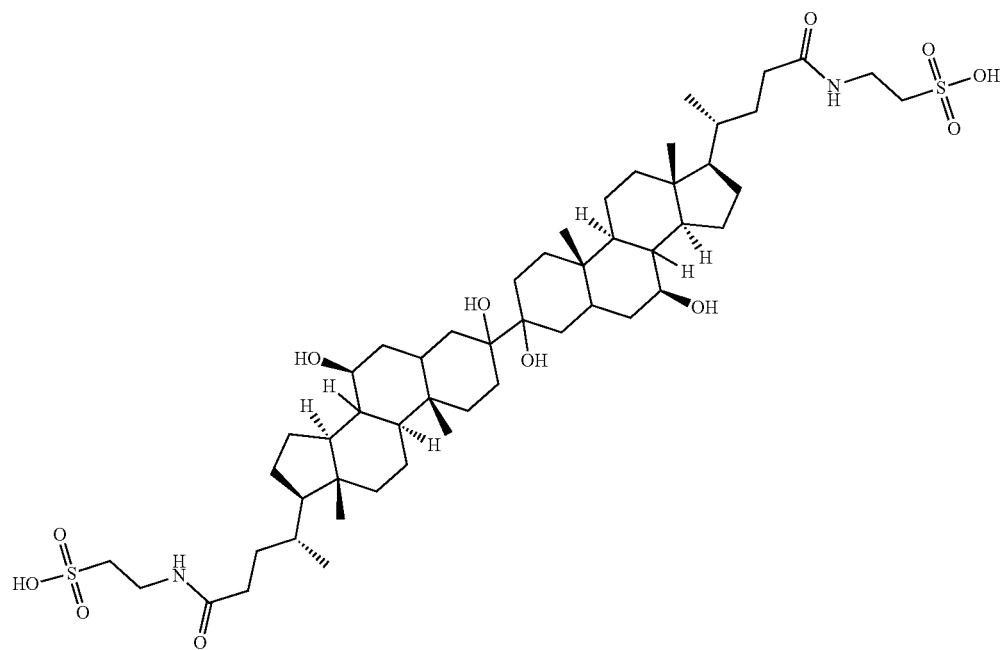
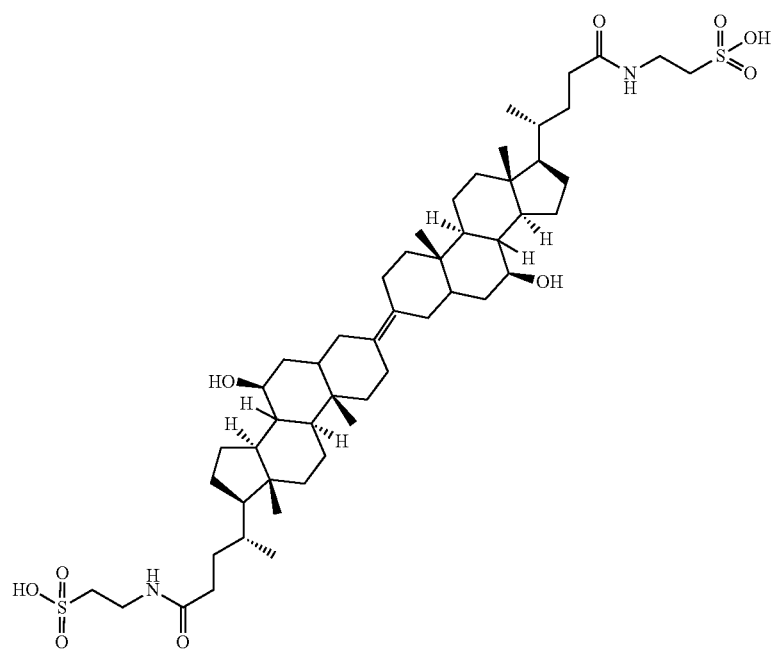

-continued
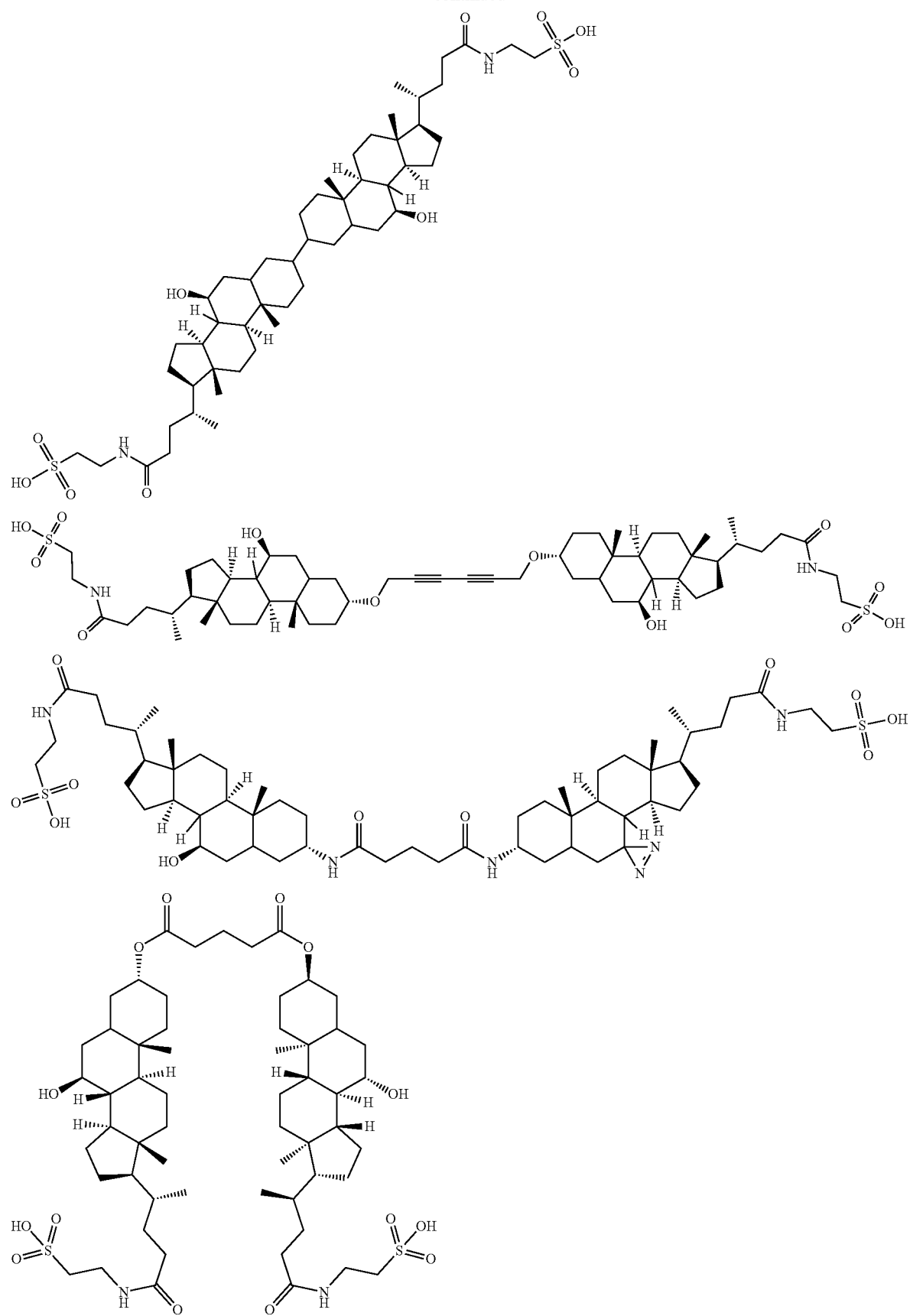

195
196
-continued
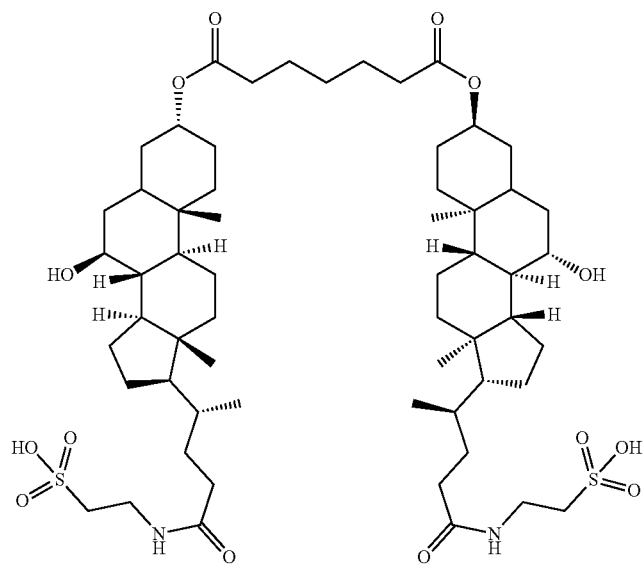
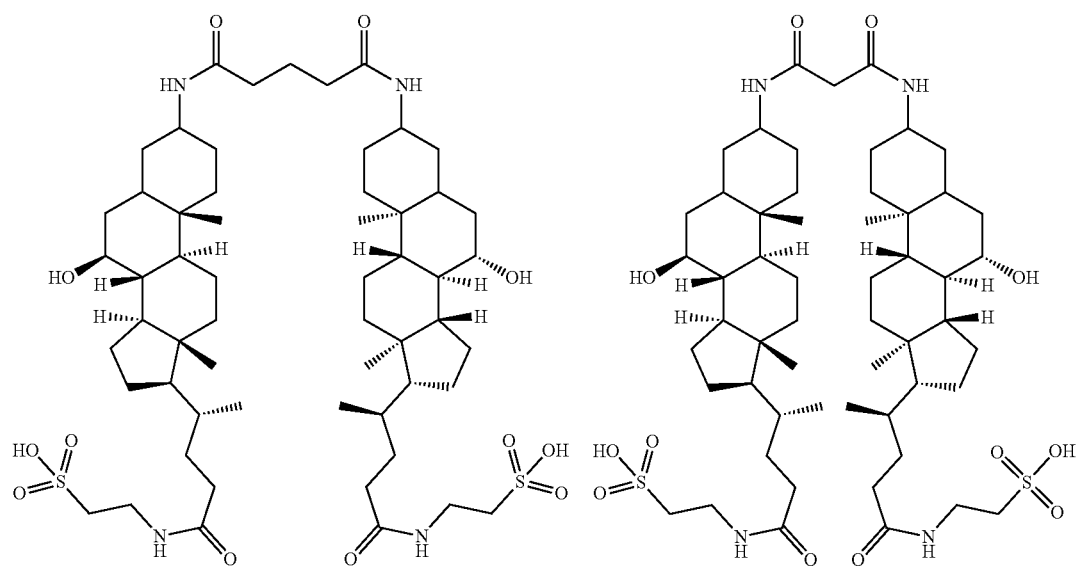

197                              -continued                              198
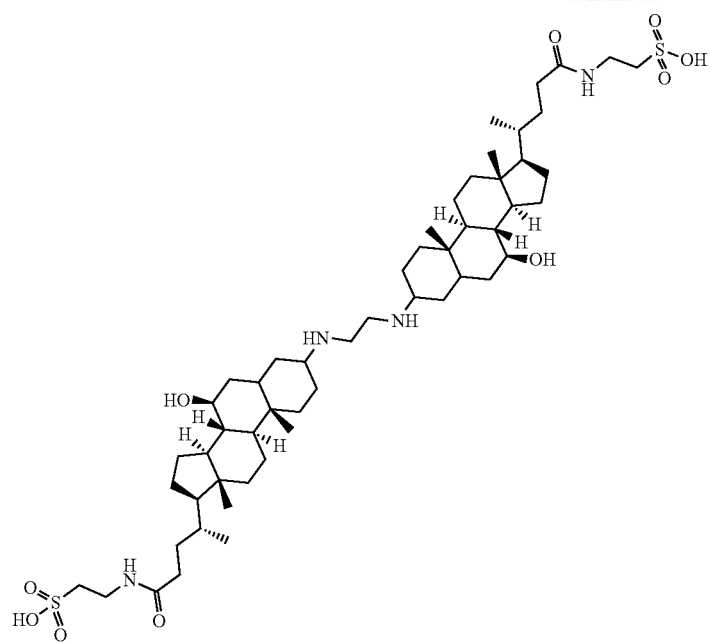
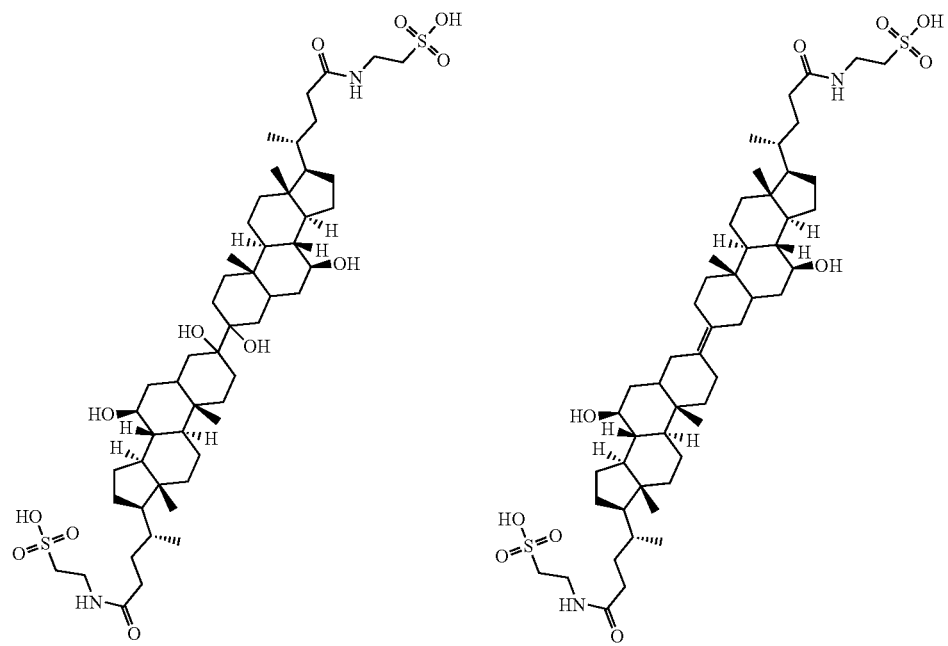

-continued
199
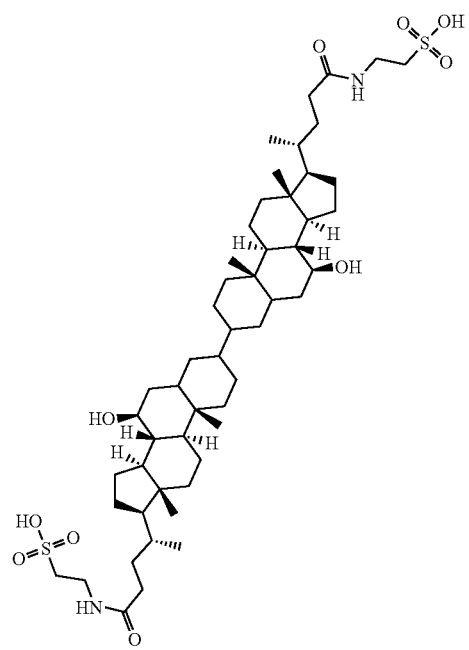
200
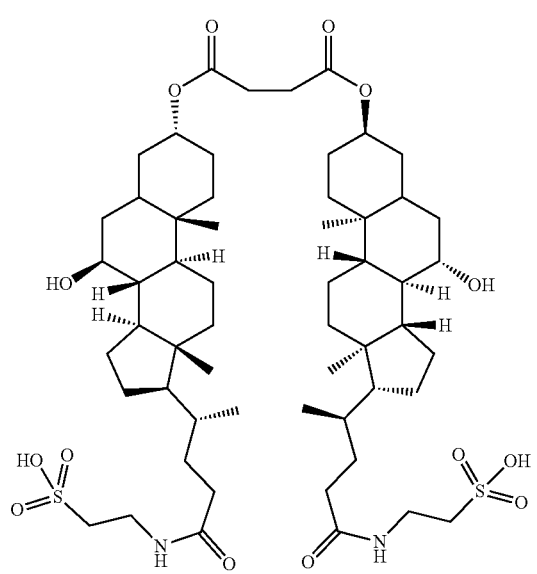
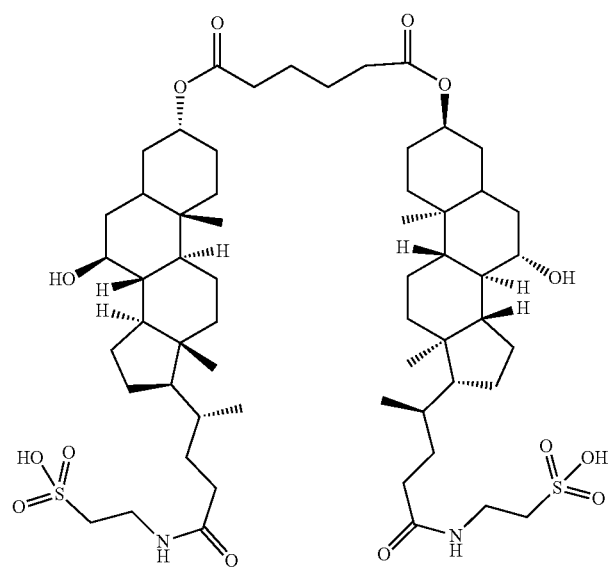

-continued
201  202
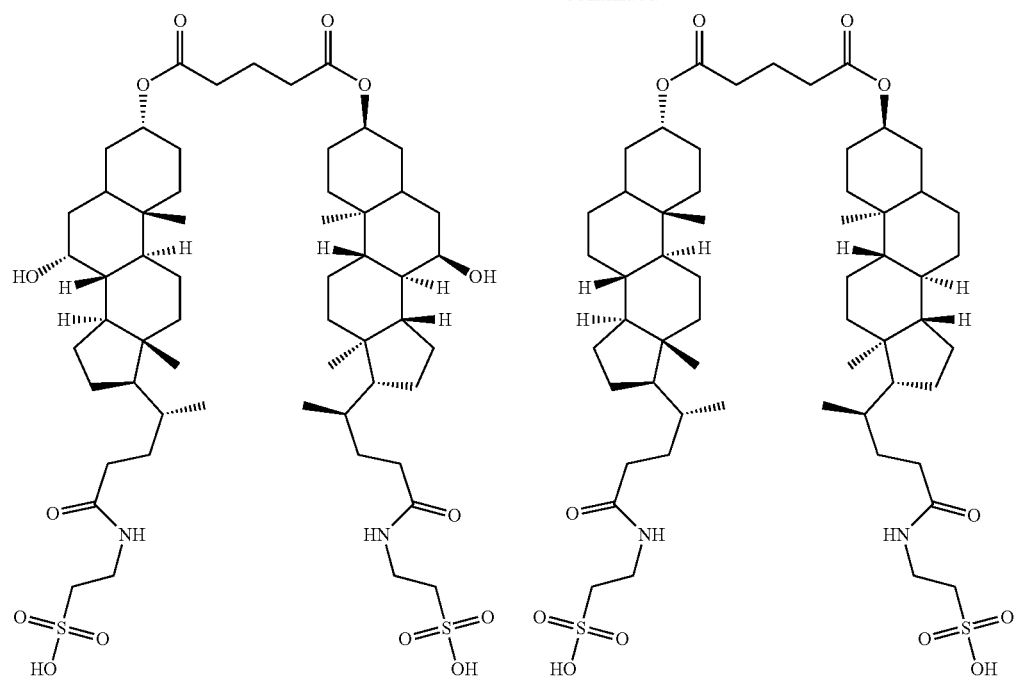
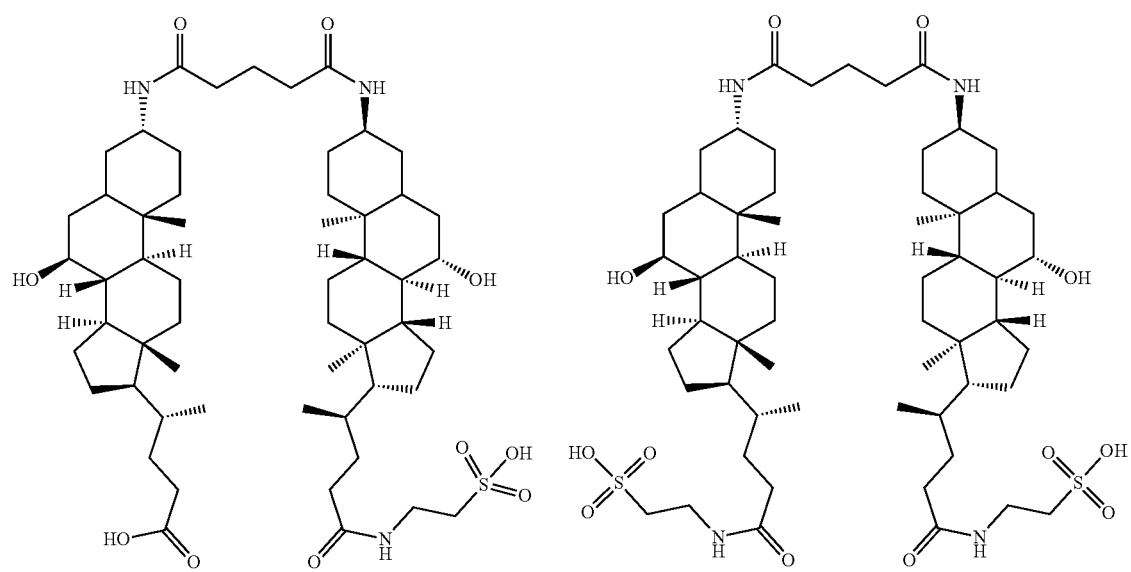

203
204
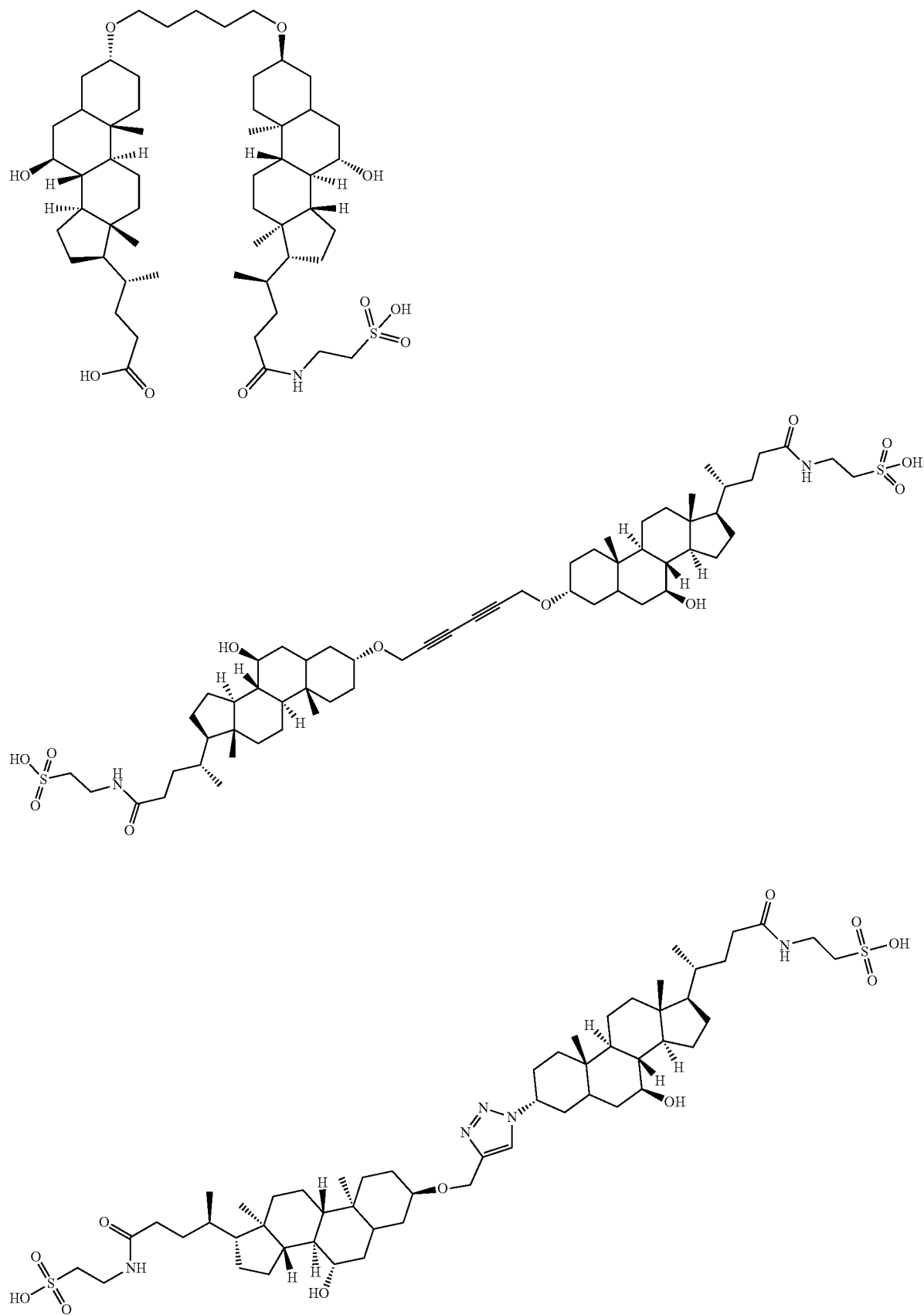

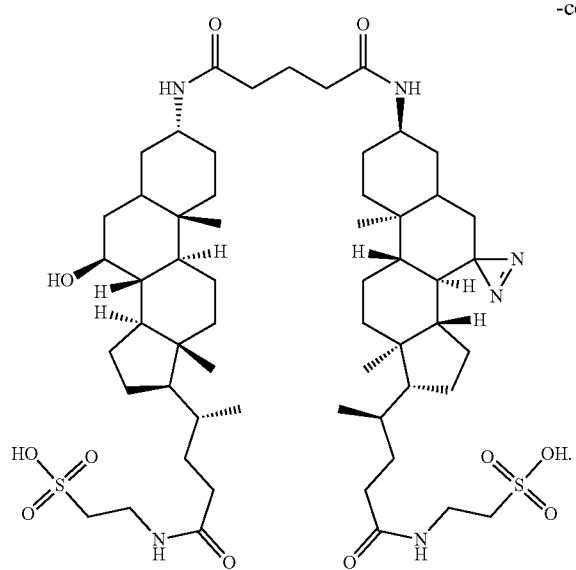
-continued
* * * * *